(12) United States Patent
Lyamichev et al.

(10) Patent No.: US 7,678,542 B2
(45) Date of Patent: *Mar. 16, 2010

(54) CHARGE TAGS AND THE SEPARATION OF NUCLEIC ACID MOLECULES

(75) Inventors: Victor Lyamichev, Madison, WI (US); Zbigniev Skrzypczynski, Verona, WI (US); Hatim T. Allawi, Madison, WI (US); Sarah R. Wayland, Madison, WI (US); Tsetska Y. Takova, Madison, WI (US); Bruce P. Neri, Carlsbad, CA (US); James R. Prudent, Madison, WI (US); Jeff G. Hall, Waunakee, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/132,198

(22) Filed: Jun. 3, 2008

(65) Prior Publication Data

US 2009/0078574 A1    Mar. 26, 2009

Related U.S. Application Data

(60) Division of application No. 10/875,094, filed on Jun. 23, 2004, now Pat. No. 7,384,746, which is a division of application No. 09/777,430, filed on Feb. 6, 2001, now Pat. No. 6,780,982, which is a continuation-in-part of application No. 09/333,145, filed on Jun. 14, 1999, now Pat. No. 6,706,471, which is a continuation of application No. 08/682,853, filed on Jul. 12, 1996, now Pat. No. 6,001,567.

(51) Int. Cl.
*C12Q 1/68* (2006.01)
*C07H 21/00* (2006.01)
*C07H 21/02* (2006.01)

(52) U.S. Cl. .................. 435/6; 536/23.1; 536/24.3; 536/25.3; 536/26.6

(58) Field of Classification Search .............. 435/6; 536/23.1, 24.3, 25.3, 26.6
See application file for complete search history.

(56) References Cited

U.S. PATENT DOCUMENTS 4,683,195 A    7/1987    Mullis et al. ............... 435/6

(Continued)

FOREIGN PATENT DOCUMENTS

WO    WO 96/27681    9/1996

(Continued)

OTHER PUBLICATIONS

Allawi, H.T. & SantaLucia, J., Jr. Thermodynamics and NMR of internal G.T mismatches in DNA. Biochemistry 36, 10581-94 (1997).

(Continued)

*Primary Examiner*—Jezia Riley
(74) *Attorney, Agent, or Firm*—Casimir Jones, S.C.

(57) ABSTRACT

The present invention relates to novel phosphoramidites, including positive and neutrally charged compounds. The present invention also provides charge tags for attachment to materials including solid supports and nucleic acids, wherein the charge tags increase or decrease the net charge of the material. The present invention further provides methods for separating and characterizing molecules based on the charge differentials between modified and unmodified materials.

21 Claims, 48 Drawing Sheets

U.S. PATENT DOCUMENTS

| | | | |
|---|---|---|---|
| 4,683,202 | A | 7/1987 | Mullis .................. 435/91 |
| 4,775,619 | A | 10/1988 | Urdea .................. 435/6 |
| 4,876,187 | A | 10/1989 | Duck et al. .................. 435/6 |
| 4,965,188 | A | 10/1990 | Mullis et al. .................. 435/6 |
| 5,011,769 | A | 4/1991 | Duck et al. .................. 435/6 |
| 5,118,605 | A | 6/1992 | Urdea .................. 435/6 |
| 5,210,015 | A | 5/1993 | Gelfand et al. .................. 435/6 |
| 5,403,711 | A | 4/1995 | Walder et al. .................. 435/6 |
| 5,427,930 | A | 6/1995 | Birkenmeyer et al. .... 435/91.52 |
| 5,470,705 | A | 11/1995 | Grossman et al. .................. 435/6 |
| 5,494,810 | A | 2/1996 | Barany et al. ............ 435/91.52 |
| 5,514,543 | A | 5/1996 | Grossman et al. .................. 435/6 |
| 5,703,222 | A | 12/1997 | Grossman et al. .......... 536/24.3 |
| 5,777,096 | A | 7/1998 | Grossman et al. .......... 536/24.3 |
| 5,807,682 | A | 9/1998 | Grossman et al. .................. 435/6 |
| 5,846,717 | A | 12/1998 | Brow et al. .................. 435/6 |
| 5,882,867 | A | 3/1999 | Ullman et al. .................. 435/6 |
| 5,916,426 | A | 6/1999 | Madabhushi et al. ........ 204/451 |
| 5,952,174 | A | 9/1999 | Nikiforov et al. .................. 435/6 |
| 5,985,557 | A | 11/1999 | Prudent et al. .................. 435/6 |
| 5,994,069 | A | 11/1999 | Hall et al. .................. 435/6 |
| 6,001,567 | A | 12/1999 | Brow et al. .................. 435/6 |
| 6,090,543 | A | 7/2000 | Prudent et al. .................. 435/6 |
| 6,090,606 | A | 7/2000 | Kaiser et al. .................. 435/6 |
| 6,110,677 | A | 8/2000 | Western et al. .................. 435/6 |
| 6,121,001 | A | 9/2000 | Western et al. .................. 435/6 |
| 6,706,471 | B1 * | 3/2004 | Brow et al. .................. 435/6 |
| 7,384,746 | B2 * | 6/2008 | Lyamichev et al. ............ 435/6 |

FOREIGN PATENT DOCUMENTS

| | | |
|---|---|---|
| WO | WO 97/27214 | 7/1997 |
| WO | WO 98/23774 | 6/1998 |
| WO | WO 98/42873 | 10/1998 |
| WO | WO 01/76451 | 10/2001 |

OTHER PUBLICATIONS

Beaucage and Iyer (Tetrahedron 49:1925 [1993].
Baker (1995) Capillary Electrophoresis, Wiley-Interscience, New York, New York, Weinberger (2000).
Weinberger (2000) Capillary Electrophoresis, Second Edition, Academic Press, San Deigo, California.
Atamna et al., J. Liq. Chromatogr., 13:2517 (1990).
Nishi et al., Anal. Chem., 61:2434 (1989).
Terabe et al., Anal. Chem., 56:111 (1984).
Bousse et al., Annu. Rev. Biophys. Biomol. Struct., 29:155 (2000).
Reynaldo et al., J. Mol. Biol. 97:511 [2000]).
B.C. Froehler, Methods in Molecular Biology, 20:33, S. Agrawal, Ed. Humana Press; Totowa, New Jersey[1993].
Froehler,Tetrahedron Lett. 27:5575[1986].
Froehler et al., Nucl.Acids Res. 16:4831 [1988].
Letsinger et al., J.Am. Chem.Soc., 110:4470 [1988].
Agrawal et al., Nucl. Acid Res. 18:5419 [1990].
Handong et al., Bioconjugate Chem. 8:49 [1997].
Vinogradov et al., Bioconjugate Chem. 7:3 [1995].
Schultz et al., Tetrachedron Lett. 36:8407 [1995].
Siebert et al., Nucleic Acids Res. 1995a. 23(6)1087-1088.
Lyamichev et al., Biochemistry 39:9523 [2000].
Andrews, Electrophoresis, 2nd Edition, Oxford University Press (1986), pp. 153-154.
Engelke et al., Anal. Biochem., 191:396 [1990].
Marmur and Lane, Proc. Natl. Acad. Sci. USA 46-453 (1960).
Doty et al., Proc. Natl. Acad. Sci USA 46-461 (1960).
Anderson and Young, Quantitative Filter Hybridization, in Nucleic Acid Hybridization (1985).

* cited by examiner 1  2  3  4  5  6

70 (C10 amino T's)
74 (C6 amino T's)

75

$Y^{(+)}$ = organic group capable to introduce positive charge

V-(Hex)  Z = C_6H_{12}
V-(dT)   Z = dT
V-(dC)   Z = dC
V-(dA)   Z = dA
V-(dG)   Z = dG chiral phosphoramidate phosphorus atom

A.        $\overset{(0)\phantom{xx}(+1)}{\text{3'-DNA - (DP) - (PCP)}}$

B.        $\overset{(0)\phantom{xx}(0)\phantom{xx}(+1)}{\text{3'-DNA - (DP) - (NP)}_n\text{ - (PCP)}}$ C.        $\overset{(0)\phantom{xx}(-1)\phantom{xx}(+1)}{\text{3'-DNA - (DP) - (PBB)}_n\text{ - (PCP)}_{(n+1)}}$ D.        $\overset{(0)\phantom{xx}(-1)\phantom{xx}(+1)\phantom{xxxx}(0)}{\text{3'-DNA - (DP) - (PBB)}_n\text{ - (PCP)}_{(n+1)}\text{ - (NP)}_m}$ Neutral Phosphoramidite Net Charge : 0

Positively Charged Phosphoramidite

Net Charge : +1

A.

```
                          5'-HP1⁺  ↓
                              Cy3 CTTCGGAGTTTGGG-NH₂-3'
5'-GGGTTGTGGAGTGAGTGTTCAAGTA-3'
3'-CCCAACACCUCACUCACAAGUUCAGAAGCCUCAAACCCAAACGAA-5'
```

B.

V(dN)

804-41

V(HEX)

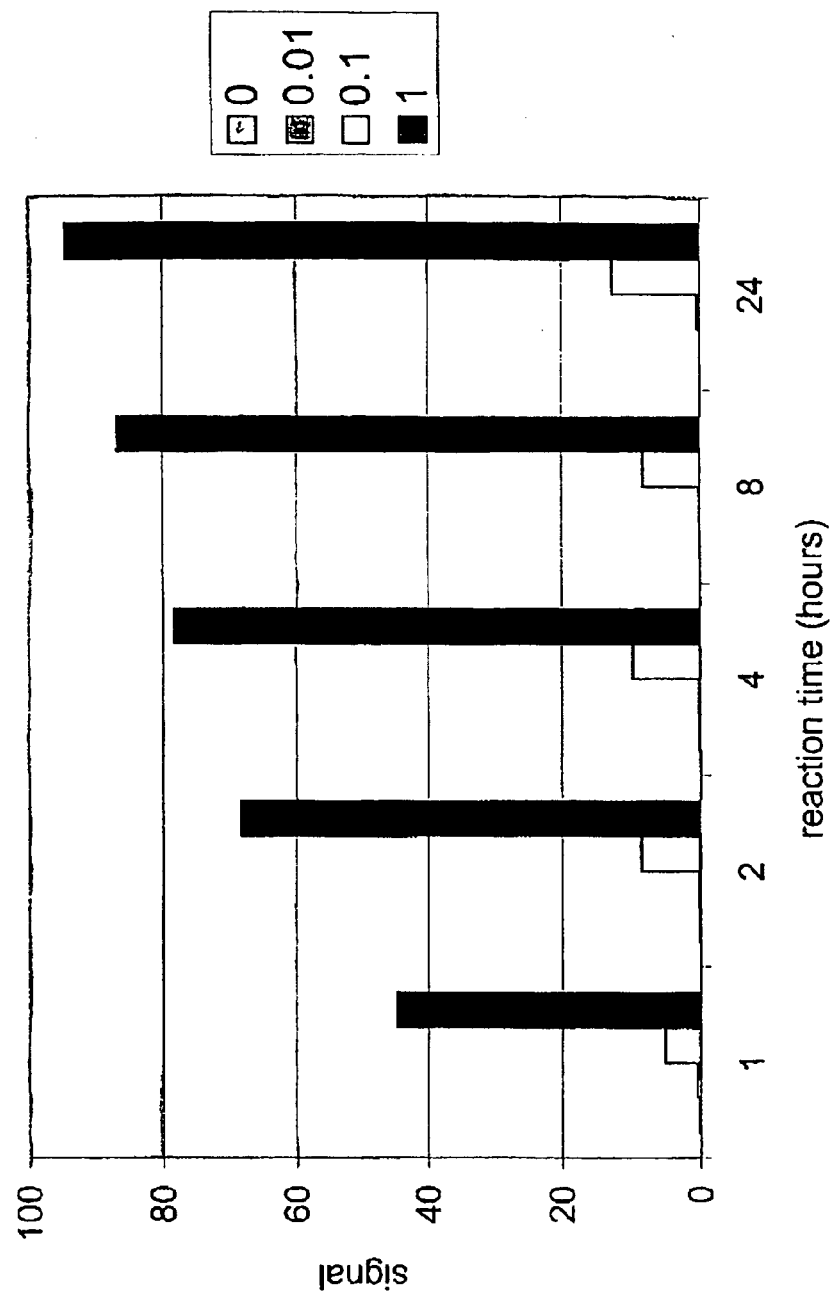

Primary reaction

Human MCP-1 mRNA

5'-CCGTCACGCCTCCTTCGGAGTTTGGG-NH$_2$-3'

3'-NH$_2$-GTGCGGAGGAAGCCTCAAACCCAA-5'

Secondary reaction

Primary reaction

5'-CCTTCCTTATCCTGGATCTTGGCA-3'
3'-GGAAGGAATAGGACCTAGAACCGGAAATGTAAAAGATAGCATAGGC-5'

Human Ubiquitin mRNA

5'-AACGAGGCGCACCTTTACATTTTCTATCGT-NH$_2$-3'

3'-NH$_2$-CGCGTGGAAATGTAAAAGATAGCA-5'

Secondary reaction

5' AACGAGGCGCACC
3'-NH$_2$-AAUUGCTCCGCGTGGTGAACGAAG$\underline{A}$AGGC-5'

SEQUENCE LISTING

```
<160> NUMBER OF SEQ ID NOS: 85

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer bearing a Cy3 group.
<220> FEATURE:
<221> NAME/KEY: misc_feature
<222> LOCATION: (1)..(2)
<223> OTHER INFORMATION: The residues at these positions are
      amino-modified bases.

<400> SEQUENCE: 1
tcttttcacc agcgagacgg g                                              21

<210> SEQ ID NO 2
<211> LENGTH: 23
<212> TYPE: DNA
<213> ORGANISM: Artificial Sequence
<220> FEATURE:
<223> OTHER INFORMATION: Synthetic
```

<400> SEQUENCE: 2
tattgggcgc agggtggtt ttt                                               23

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
cagggtgaag ggaagaagaa agcgaaaggt                                       30

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4 caggggaag ggaagaagaa agcgaaaggt                                        30

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
cacgaattcc gaggcgatgc ttccgctc                                         28

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
tcgacgtcga ctaacccttg gcggaaagcc                                       30

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
gcatcgcctc ggaattcatg gtc                                              23

<210> SEQ ID NO 8
<211> LENGTH: 836
<212> TYPE: PRT
<213> ORGANISM: Thermus thermophilus

<400> SEQUENCE: 8

Met Asn Ser Glu Ala Met Leu Pro Leu Phe Glu Pro Lys Gly Arg Val
1               5                   10                  15

Leu Leu Val Asp Gly His His Leu Ala Tyr Arg Thr Phe Phe Ala Leu
            20                  25                  30

-continued

```
Lys Gly Leu Thr Thr Ser Arg Gly Glu Pro Val Gln Ala Val Tyr Gly
         35                  40                  45

Phe Ala Lys Ser Leu Leu Lys Ala Leu Lys Glu Asp Gly Tyr Lys Ala
     50                  55                  60

Val Phe Val Val Phe Asp Ala Lys Ala Pro Ser Phe Arg His Glu Ala
 65                  70                  75                  80

Tyr Glu Ala Tyr Lys Ala Gly Arg Ala Pro Thr Pro Glu Asp Phe Pro
                 85                  90                  95

Arg Gln Leu Ala Leu Ile Lys Glu Leu Val Asp Leu Leu Gly Phe Thr
                100                 105                 110

Arg Leu Glu Val Pro Gly Tyr Glu Ala Asp Val Leu Ala Thr Leu
             115                 120                 125

Ala Lys Lys Ala Glu Lys Glu Gly Tyr Glu Val Arg Ile Leu Thr Ala
    130                 135                 140

Asp Arg Asp Leu Tyr Gln Leu Val Ser Asp Arg Val Ala Val Leu His
145                 150                 155                 160

Pro Glu Gly His Leu Ile Thr Pro Glu Trp Leu Trp Glu Lys Tyr Gly
                 165                 170                 175

Leu Arg Pro Glu Gln Trp Val Asp Phe Arg Ala Leu Val Gly Asp Pro
                180                 185                 190

Ser Asp Asn Leu Pro Gly Val Lys Gly Ile Gly Glu Lys Thr Ala Leu
            195                 200                 205

Lys Leu Leu Lys Glu Trp Gly Ser Leu Glu Asn Leu Leu Lys Asn Leu
    210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270

Leu Arg Ala Phe Leu Glu Arg Leu Glu Phe Gly Ser Leu Leu His Glu
    275                 280                 285

Phe Gly Leu Leu Glu Ala Pro Ala Pro Leu Glu Glu Ala Pro Trp Pro
290                 295                 300

Pro Pro Glu Gly Ala Phe Val Gly Phe Val Leu Ser Arg Pro Glu Pro
305                 310                 315                 320

Met Trp Ala Glu Leu Lys Ala Leu Ala Ala Cys Arg Asp Gly Arg Val
                325                 330                 335

His Arg Ala Ala Asp Pro Leu Ala Gly Leu Lys Asp Leu Lys Glu Val
            340                 345                 350

Arg Gly Leu Leu Ala Lys Asp Leu Ala Val Leu Ala Ser Arg Glu Gly
    355                 360                 365

Leu Asp Leu Val Pro Gly Asp Asp Pro Met Leu Leu Ala Tyr Leu Leu
370                 375                 380

Asp Pro Ser Asn Thr Thr Pro Glu Gly Val Ala Arg Arg Tyr Gly Gly
385                 390                 395                 400

Glu Trp Thr Glu Asp Ala Ala His Arg Ala Leu Leu Ser Glu Arg Leu
                405                 410                 415

His Arg Asn Leu Leu Lys Arg Leu Glu Gly Glu Glu Lys Leu Leu Trp
            420                 425                 430

Leu Tyr His Glu Val Glu Lys Pro Leu Ser Arg Val Leu Ala His Met
    435                 440                 445

Glu Ala Thr Gly Val Arg Arg Asp Val Ala Tyr Leu Gln Ala Leu Ser
```

```
                 450                 455                 460
Leu Glu Leu Ala Glu Glu Ile Arg Arg Leu Glu Glu Val Phe Arg
465                 470                 475                 480

Leu Ala Gly His Pro Phe Asn Leu Asn Ser Arg Asp Gln Leu Glu Arg
                485                 490                 495

Val Leu Phe Asp Glu Leu Arg Leu Pro Ala Leu Gly Lys Thr Gln Lys
            500                 505                 510

Thr Gly Lys Arg Ser Thr Ser Ala Ala Val Leu Glu Ala Leu Arg Glu
        515                 520                 525

Ala His Pro Ile Val Glu Lys Ile Leu Gln His Arg Glu Leu Thr Lys
530                 535                 540

Leu Lys Asn Thr Tyr Val Asp Pro Leu Pro Ser Leu Val His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Val Ala Glu Ala Gly Trp
        595                 600                 605

Ala Leu Val Ala Leu Asp Tyr Ser Gln Ile Glu Leu Arg Val Leu Ala
    610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
                645                 650                 655

Ala Val Asp Pro Leu Met Arg Arg Ala Ala Lys Thr Val Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Val Ala Phe Ile Glu Arg Tyr Phe Gln Ser Phe
    690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Arg Tyr Val Pro Asp
                725                 730                 735

Leu Asn Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765

Met Val Lys Leu Phe Pro Arg Leu Arg Glu Met Gly Ala Arg Met Leu
    770                 775                 780

Leu Gln Val His Asp Glu Leu Leu Leu Glu Ala Pro Gln Ala Arg Ala
785                 790                 795                 800

Glu Glu Val Ala Ala Leu Ala Lys Glu Ala Met Glu Lys Ala Tyr Pro
                805                 810                 815

Leu Ala Val Pro Leu Glu Val Glu Val Gly Met Gly Glu Asp Trp Leu
            820                 825                 830

Ser Ala Lys Gly
        835

<210> SEQ ID NO 9
<211> LENGTH: 2511
<212> TYPE: DNA
<213> ORGANISM: Thermus thermophilus
```

<400> SEQUENCE: 9

```
atgaattccg aggcgatgct tccgctcttt gaacccaaag gccgggtcct cctggtggac      60
ggccaccacc tggcctaccg caccttcttc gccctgaagg gcctcaccac gagccggggc     120
gaaccggtgc aggcggtcta cggcttcgcc aagagcctcc tcaaggccct gaaggaggac     180
gggtacaagg ccgtcttcgt ggtctttgac gccaaggccc cctccttccg ccacgaggcc     240
tacgaggcct acaaggcggg gagggccccg accccgagg acttcccccg gcagctcgcc      300
ctcatcaagg agctggtgga cctcctgggg tttacccgcc tcgaggtccc cggctacgag     360
gcggacgacg ttctcgccac cctggccaag aaggcggaaa aggaggggta cgaggtgcgc     420
atcctcaccg ccgaccgcga cctctaccaa ctcgtctccg accgcgtcgc cgtcctccac     480
cccgagggcc acctcatcac cccggagtgg ctttgggaga agtacggcct caggccggag     540
cagtgggtgg acttccgcgc cctcgtgggg gaccccctcg acaacctccc cggggtcaag     600
ggcatcgggg agaagaccgc cctcaagctc tcaaggagt ggggaagcct ggaaaacctc      660
ctcaagaacc tggaccgggt aaagccagaa acgtccggg agaagatcaa ggcccacctg      720
gaagacctca ggctctcctt ggagctctcc cgggtgcgca ccgacctccc cctggaggtg     780
gacctcgccc aggggcggga gcccgaccgg gaggggctta ggccttcct ggagaggctg      840
gagttcggca gcctcctcca cgagttcggc ctcctggagg ccccgcccc cctggaggag      900
gcccctggc cccgccgga aggggccttc gtgggcttcg tcctctcccg ccccgagccc       960
atgtgggcgg agcttaaagc cctggccgcc tgcaggacg ccgggtgca ccgggcagca     1020
gacccccttgg cggggctaaa ggacctcaag gaggtccggg gcctcctcgc caaggacctc    1080
gccgtcttgg cctcgaggga ggggctagac ctcgtgcccg ggacgacccc catgctcctc    1140
gcctacctcc tggacccctc caacaccacc cccgaggggg tggcgcggcg ctacggggg      1200
gagtggacgg aggacgccgc ccaccgggcc ctcctctcgg agaggctcca tcggaacctc    1260
cttaagcgcc tcgaggggga ggagaagctc ctttggctct accacgaggt ggaaaagccc    1320
ctctccccggg tcctggccca catggaggcc accggggtac ggcgggacgt ggcctacctt    1380
caggcccttt ccctggagct tgcggaggag atccgccgcc tcgaggagga ggtcttccgc    1440
ttggcgggcc acccttcaa cctcaactcc cgggaccagc tggaaagggt gctctttgac    1500
gagcttaggc ttcccgcctt ggggaagacg caaaagacag gcaagcgctc caccagcgcc    1560
gcggtgctgg aggccctacg ggaggcccac cccatcgtgg agaagatcct ccagcaccgg    1620
gagctcacca agctcaagaa cacctacgtg gaccccctcc caagcctcgt ccacccgagg    1680
acgggccgcc tccacacccg cttcaaccag acggccacgg ccacggggag gcttagtagc    1740
tccgacccca acctgcagaa catccccgtc cgcacccct gggccagag gatccgccgg      1800
gccttcgtgg ccgaggcggg ttgggcgttg gtgccctgg actatagcca gatagagctc    1860
cgcgtcctcg cccacctctc cggggacgaa aacctgatca gggtcttcca ggagggaag    1920
gacatccaca cccagaccgc aagctggatg ttcggcgtcc cccggaggc cgtgaccccc    1980
ctgatgcgcc gggcggccaa gacggtgaac ttcgcgtcc tctacggcat gtccgcccat    2040
aggctctccc aggagcttgc catccctac gaggaggcgg tggcctttat agagcgctac    2100
ttccaaagct cccccaaggt gcgggcctgg atagaaaaga ccctggagga ggggaggaag    2160
cggggctacg tggaaaccct cttcggaaga aggcgctacg tgcccgacct caacgcccgg    2220
gtgaagagcg tcagggaggc cgcggagcgc atggccttca acatgccgt ccagggcacc    2280
```

```
gccgccgacc tcatgaagct cgccatggtg aagctcttcc cccgcctccg ggagatgggg      2340
gcccgcatgc tcctccaggt ccacgacgag ctcctcctgg aggcccccca agcgcgggcc      2400
gaggaggtgg cggctttggc caaggaggcc atggagaagg cctatcccct cgccgtgccc      2460
ctggaggtgg aggtggggat ggggggaggac tggctttccg ccaagggtta g              2511
```

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10

```
caggaggagc tcgttgtgga cctgga                                            26
```

<210> SEQ ID NO 11
<211> LENGTH: 836
<212> TYPE: PRT
<213> ORGANISM: Thermus thermophilus

<400> SEQUENCE: 11

```
Met Asn Ser Glu Ala Met Leu Pro Leu Phe Glu Pro Lys Gly Arg Val
1               5                   10                  15

Leu Leu Val Asp Gly His His Leu Ala Tyr Arg Thr Phe Phe Ala Leu
            20                  25                  30

Lys Gly Leu Thr Thr Ser Arg Gly Glu Pro Val Gln Ala Val Tyr Gly
        35                  40                  45

Phe Ala Lys Ser Leu Leu Lys Ala Leu Lys Glu Asp Gly Tyr Lys Ala
    50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
            100                 105                 110

Arg Leu Glu Val Pro Gly Tyr Glu Ala Asp Asp Val Leu Ala Thr Leu
        115                 120                 125

Ala Lys Lys Ala Glu Lys Glu Gly Tyr Glu Val Arg Ile Leu Thr Ala
    130                 135                 140

Asp Arg Asp Leu Tyr Gln Leu Val Ser Asp Arg Val Ala Val Leu His
145                 150                 155                 160

Pro Glu Gly His Leu Ile Thr Pro Glu Trp Leu Trp Glu Lys Tyr Gly
                165                 170                 175

Leu Arg Pro Glu Gln Trp Val Asp Phe Arg Ala Leu Val Gly Asp Pro
            180                 185                 190

Ser Asp Asn Leu Pro Gly Val Lys Gly Ile Gly Glu Lys Thr Ala Leu
        195                 200                 205

Lys Leu Leu Lys Glu Trp Gly Ser Leu Glu Asn Leu Leu Lys Asn Leu
    210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270
```

```
Leu Arg Ala Phe Leu Glu Arg Leu Glu Phe Gly Ser Leu Leu His Glu
        275                 280                 285
Phe Gly Leu Leu Glu Ala Pro Ala Pro Leu Glu Glu Ala Pro Trp Pro
        290                 295                 300
Pro Pro Glu Gly Ala Phe Val Gly Phe Val Leu Ser Arg Pro Glu Pro
305                 310                 315                 320
Met Trp Ala Glu Leu Lys Ala Leu Ala Ala Cys Arg Asp Gly Arg Val
                    325                 330                 335
His Arg Ala Ala Asp Pro Leu Ala Gly Leu Lys Asp Leu Lys Glu Val
                340                 345                 350
Arg Gly Leu Leu Ala Lys Asp Leu Ala Val Leu Ala Ser Arg Glu Gly
            355                 360                 365
Leu Asp Leu Val Pro Gly Asp Pro Met Leu Leu Ala Tyr Leu Leu
        370                 375                 380
Asp Pro Ser Asn Thr Thr Pro Glu Gly Val Ala Arg Arg Tyr Gly Gly
385                 390                 395                 400
Glu Trp Thr Glu Asp Ala Ala His Arg Ala Leu Leu Ser Glu Arg Leu
                    405                 410                 415
His Arg Asn Leu Leu Lys Arg Leu Glu Gly Glu Glu Lys Leu Leu Trp
                420                 425                 430
Leu Tyr His Glu Val Glu Lys Pro Leu Ser Arg Val Leu Ala His Met
            435                 440                 445
Glu Ala Thr Gly Val Arg Arg Asp Val Ala Tyr Leu Gln Ala Leu Ser
        450                 455                 460
Leu Glu Leu Ala Glu Glu Ile Arg Arg Leu Glu Glu Val Phe Arg
465                 470                 475                 480
Leu Ala Gly His Pro Phe Asn Leu Asn Ser Arg Asp Gln Leu Glu Arg
                    485                 490                 495
Val Leu Phe Asp Glu Leu Arg Leu Pro Ala Leu Gly Lys Thr Gln Lys
                500                 505                 510
Thr Gly Lys Arg Ser Thr Ser Ala Ala Val Leu Glu Ala Leu Arg Glu
            515                 520                 525
Ala His Pro Ile Val Glu Lys Ile Leu Gln His Arg Glu Leu Thr Lys
        530                 535                 540
Leu Lys Asn Thr Tyr Val Asp Pro Leu Pro Ser Leu Val His Pro Arg
545                 550                 555                 560
Thr Gly Arg Leu His Thr Arg Phe Asn Gln Thr Ala Thr Ala Thr Gly
                    565                 570                 575
Arg Leu Ser Ser Ser Asp Pro Asn Leu Gln Asn Ile Pro Val Arg Thr
                580                 585                 590
Pro Leu Gly Gln Arg Ile Arg Arg Ala Phe Val Ala Glu Ala Gly Trp
            595                 600                 605
Ala Leu Val Ala Leu Asp Tyr Ser Gln Ile Glu Leu Arg Val Leu Ala
        610                 615                 620
His Leu Ser Gly Asp Glu Asn Leu Ile Arg Val Phe Gln Glu Gly Lys
625                 630                 635                 640
Asp Ile His Thr Gln Thr Ala Ser Trp Met Phe Gly Val Pro Pro Glu
                    645                 650                 655
Ala Val Asp Pro Leu Met Arg Arg Ala Ala Lys Thr Val Asn Phe Gly
                660                 665                 670
Val Leu Tyr Gly Met Ser Ala His Arg Leu Ser Gln Glu Leu Ala Ile
            675                 680                 685
Pro Tyr Glu Glu Ala Val Ala Phe Ile Glu Arg Tyr Phe Gln Ser Phe
```

-continued

```
               690                 695                 700
Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Tyr Val Pro Asp
                725                 730                 735

Leu Asn Ala Arg Val Lys Ser Val Arg Glu Ala Ala Glu Arg Met Ala
                740                 745                 750

Phe Asn Met Pro Val Gln Gly Thr Ala Ala Asp Leu Met Lys Leu Ala
                755                 760                 765

Met Val Lys Leu Phe Pro Arg Leu Arg Glu Met Gly Ala Arg Met Leu
770                 775                 780

Leu Gln Val His Asn Glu Leu Leu Leu Glu Ala Pro Gln Ala Arg Ala
785                 790                 795                 800

Glu Glu Val Ala Ala Leu Ala Lys Glu Ala Met Glu Lys Ala Tyr Pro
                805                 810                 815

Leu Ala Val Pro Leu Glu Val Glu Val Gly Met Gly Glu Asp Trp Leu
                820                 825                 830

Ser Ala Lys Gly
        835

<210> SEQ ID NO 12
<211> LENGTH: 2511
<212> TYPE: DNA
<213> ORGANISM: Thermus thermophilus

<400> SEQUENCE: 12
atgaattccg aggcgatgct tccgctcttt gaacccaaag gccgggtcct cctggtggac      60
ggccaccacc tggcctaccg caccttcttc gccctgaagg cctcaccac gagccggggc     120 gaaccggtgc aggcggtcta cggcttcgcc aagagcctcc tcaaggccct gaaggaggac     180
gggtacaagg ccgtcttcgt ggtctttgac gccaaggccc cctccttccg ccacgaggcc     240
tacgaggcct acaaggcggg gagggccccg accccgagg acttccccg gcagctcgcc     300 ctcatcaagg agctggtgga cctcctgggg tttacccgcc tcgaggtccc cggctacgag     360
gcggacgacg ttctcgccac cctggccaag aaggcggaaa aggagggta cgaggtgcgc     420 atcctcaccg ccgaccgcga cctctaccaa ctcgtctccg accgcgtcgc cgtcctccac     480
cccgagggcc acctcatcac cccggagtgg ctttgggaga agtacggcct caggccggag     540
cagtgggtgg acttccgcgc cctcgtgggg gaccctccg acaacctccc cggggtcaag     600
ggcatcgggg agaagaccgc cctcaagctc tcaaggagt ggggaagcct ggaaaacctc     660
ctcaagaacc tggaccgggt aaagccagaa aacgtccggg agaagatcaa ggcccacctg     720
gaagacctca ggctctcctt ggagctctcc cgggtgcgca ccgacctccc cctggaggtg     780
gacctcgccc aggggcggga gcccgaccgg aggggctta gggccttcct ggagaggctg     840
gagttcggca gcctcctcca cgagttcggc ctcctggagg ccccgccc cctggaggag     900 gccccctggc cccgccgga agggccttc gtgggcttcg tcctctcccg ccccgagccc     960
atgtgggcgg agcttaaagc cctggccgcc tgcagggacg gccgggtgca ccgggcagca    1020
gaccccttgg cggggctaaa ggacctcaag gaggtccggg gcctcctcgc caaggacctc    1080
gccgtcttgg cctcgaggga ggggctagac ctcgtgcccg ggacgacccc catgctcctc    1140
gcctacctcc tggaccccctc caacaccacc cccgaggggg tggcgcggcg ctacgggggg    1200
gagtggacgg aggacgccgc ccaccgggcc ctcctctcgg agaggctcca tcggaaccte    1260
```

-continued

```
cttaagcgcc tcgaggggga ggagaagctc ctttggctct accacgaggt ggaaaagccc     1320
ctctcccggg tcctggccca catggaggcc accgggtac  ggcgggacgt ggcctacctt     1380
caggcccttt ccctggagct tgcggaggag atccgccgcc tcgaggagga ggtcttccgc     1440
ttggcgggca accccttcaa cctcaactcc cgggaccagc tggaaagggt gctctttgac     1500
gagcttaggc ttcccgcctt ggggaagacg caaaagacag gcaagcgctc caccagcgcc     1560
gcggtgctgg aggccctacg ggaggccac  cccatcgtgg agaagatcct ccagcaccgg     1620
gagctcacca agctcaagaa cacctacgtg gaccccctcc caagcctcgt ccacccgagg     1680
acgggccgcc tccacacccg cttcaaccag acggccacgg ccacggggag gcttagtagc     1740 tccgaccccca acctgcagaa catccccgtc cgcaccccct gggccagag  gatccgccgg     1800 gccttcgtgg ccgaggcggg ttgggcgttg gtggccctgg actatagcca gatagagctc     1860
cgcgtcctcg cccacctctc cggggacgaa aacctgatca gggtcttcca ggaggggaag     1920
gacatccaca cccagaccgc aagctggatg ttcggcgtcc ccccggaggc cgtggacccc     1980
ctgatgcgcc gggcggccaa gacggtgaac ttcgcgtcc  tctacggcat gtccgcccat     2040
aggctctccc aggagcttgc catcccctac gaggaggcgg tggcctttat agagcgctac     2100
ttccaaagct tccccaaggt gcgggcctgg atagaaaaga ccctggagga ggggaggaag     2160
cggggctacg tggaaaccct cttcggaaga aggcgctacg tgcccgacct caacgcccgg     2220
gtgaagagcg tcagggaggc cgcggagcgc atggccttca acatgcccgt ccagggcacc     2280
gccgccgacc tcatgaagct cgccatggtg aagctcttcc cccgcctccg ggagatgggg     2340
gcccgcatgc tcctccaggt ccacaacgag ctcctcctgg aggcccccca agcgcgggcc     2400
gaggaggtgg cggctttggc caaggaggcc atggagaagg cctatcccct cgccgtgccc     2460
ctggaggtgg aggtgggga  tggggaggac tggctttccg ccaagggtta g              2511
```

```
<210> SEQ ID NO 13
<211> LENGTH: 58
<212> TYPE: DNA
<213> ORGANISM: Artificial Sequence
<220> FEATURE:
<223> OTHER INFORMATION: Synthetic

<400> SEQUENCE: 13
tgcctgcagg tcgacgctag ctagtggtgg tggtggtggt gaccccttggc ggaaagcc        58

<210> SEQ ID NO 14
<211> LENGTH: 2526
<212> TYPE: DNA
<213> ORGANISM: Thermus thermophilus

<400> SEQUENCE: 14
atgaattccg aggcgatgct tccgctcttt gaacccaaag gccgggtcct cctggtggac       60
ggccaccacc tggcctaccg caccttcttc gccctgaagg cctcaccac  gagccggggc      120 gaaccggtgc aggcggtcta cggcttcgcc aagagcctcc tcaaggccct gaaggaggac      180
gggtacaagg ccgtcttcgt ggtctttgac gccaaggccc cctccttccg ccacgaggcc      240
tacgaggcct acaaggcggg gagggccccg accccgagg  acttcccccg gcagctcgcc      300
ctcatcaagg agctggtgga cctcctgggg tttacccgcc tcgaggtccc cggctacgag      360
gcggacgacg ttctcgccac cctggccaag aaggcggaaa aggagggta  cgaggtgcgc      420 atcctcaccg ccgaccgcga cctctaccaa ctcgtctccg accgcgtcgc cgtcctccac      480
cccgagggcc acctcatcac ccccggagtgg ctttgggaga agtacggcct caggccggag      540
```

```
cagtgggtgg acttccgcgc cctcgtgggg gacccctccg acaacctccc cggggtcaag    600
ggcatcgggg agaagaccgc cctcaagctc ctcaaggagt ggggaagcct ggaaaacctc    660
ctcaagaacc tggaccgggt aaagccagaa aacgtccggg agaagatcaa ggcccacctg    720
gaagacctca ggctctcctt ggagctctcc cgggtgcgca ccgacctccc cctggaggtg    780
gacctcgccc aggggcggga gcccgaccgg gaggggctta gggccttcct ggagaggctg    840
gagttcggca gcctcctcca cgagttcggc ctcctggagg cccccgcccc cctggaggag    900 gcccctggc ccccgccgga aggggccttc gtgggcttcg tcctctcccg ccccgagccc     960
atgtgggcgg agcttaaagc cctggccgcc tgcagggacg gccgggtgca ccgggcagca   1020
gaccccttgg cggggctaaa ggacctcaag gaggtccggg cctcctcgc caaggacctc    1080 gccgtcttgg cctcgaggga ggggctagac ctcgtgcccg gggacgaccc catgctcctc   1140
gcctacctcc tggacccctc caacaccacc cccgaggggg tggcgcggcg ctacggggg    1200 gagtggacgg aggacgccgc ccaccgggcc ctcctctcgg agaggctcca tcggaacctc   1260
cttaagcgcc tcgaggggga ggagaagctc ctttggctct accacgaggt ggaaaagccc   1320
ctctcccggg tcctggccca catggaggcc accggggtac ggcgggacgt ggcctacctt   1380
caggcccttt ccctggagct tgcggaggag atccgccgcc tcgaggagga ggtcttccgc   1440
ttggcgggcc accccttcaa cctcaactcc cgggaccagc tggaaagggt gctctttgac   1500
gagcttaggc ttcccgcctt ggggaagacg caaaagacag gcaagcgctc caccagcgcc   1560
gcggtgctgg aggcctacg ggaggccac cccatcgtgg agaagatcct ccagcaccgg    1620
gagctcacca gctcaagaa cacctacgtg gacccctcc caagcctcgt ccacccgagg    1680
acgggccgcc tccacacccg cttcaaccag acggccacgg ccacggggag gcttagtagc   1740
tccgacccca acctgcagaa catccccgtc cgcaccccct gggccagag atccgccgg    1800 gccttcgtgg ccgaggcggg ttgggcgttg gtggccctgg actatagcca gatagagctc   1860
cgcgtcctcg cccacctctc cggggacgaa aacctgatca gggtcttcca ggaggggaag   1920
gacatccaca cccagaccgc aagctggatg ttcggcgtcc ccccggaggc cgtggacccc   1980
ctgatgcgcc gggcggccaa gacggtgaac ttcggcgtcc tctacggcat gtccgcccat   2040
aggctctccc caggagcttgc catcccctac gaggaggcgg tggcctttat agagcgctac   2100
ttccaaagct tccccaaggt gcgggcctgg atagaaaaga ccctggagga ggggaggaag   2160
cggggctacg tggaaaccct cttcggaaga aggcgctacg tgcccgacct caacgcccgg   2220
gtgaagagcg tcagggaggc cgcggagcgc atggccttca acatgcccgt ccagggcacc   2280
gccgccgacc tcatgaagct cgccatggtg aagctcttcc cccgcctccg ggagatgggg   2340
gcccgcatgc tcctccaggt ccacaacgag ctcctcctgg aggcccccca agcgcgggcc   2400
gaggaggtgg cggctttggc caaggaggcc atggagaagg cctatccct cgccgtgccc   2460 ctggaggtgg aggtggggat gggggaggac tggctttccg ccaagggtca ccaccaccac   2520
caccac                                                               2526

<210> SEQ ID NO 15
<211> LENGTH: 842
<212> TYPE: PRT
<213> ORGANISM: Thermus thermophilus

<400> SEQUENCE: 15

Met Asn Ser Glu Ala Met Leu Pro Leu Phe Glu Pro Lys Gly Arg Val
1               5                   10                  15
```

```
Leu Leu Val Asp Gly His His Leu Ala Tyr Arg Thr Phe Phe Ala Leu
            20                  25                  30

Lys Gly Leu Thr Thr Ser Arg Gly Glu Pro Val Gln Ala Val Tyr Gly
            35                  40                  45

Phe Ala Lys Ser Leu Leu Lys Ala Leu Lys Glu Asp Gly Tyr Lys Ala
            50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
            100                 105                 110

Arg Leu Glu Val Pro Gly Tyr Glu Ala Asp Asp Val Leu Ala Thr Leu
            115                 120                 125

Ala Lys Lys Ala Glu Lys Glu Gly Tyr Glu Val Arg Ile Leu Thr Ala
            130                 135                 140

Asp Arg Asp Leu Tyr Gln Leu Val Ser Asp Arg Val Ala Val Leu His
145                 150                 155                 160

Pro Glu Gly His Leu Ile Thr Pro Glu Trp Leu Trp Glu Lys Tyr Gly
                165                 170                 175

Leu Arg Pro Glu Gln Trp Val Asp Phe Arg Ala Leu Val Gly Asp Pro
            180                 185                 190

Ser Asp Asn Leu Pro Gly Val Lys Gly Ile Gly Glu Lys Thr Ala Leu
            195                 200                 205

Lys Leu Leu Lys Glu Trp Gly Ser Leu Glu Asn Leu Leu Lys Asn Leu
            210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270

Leu Arg Ala Phe Leu Glu Arg Leu Glu Phe Gly Ser Leu Leu His Glu
            275                 280                 285

Phe Gly Leu Leu Glu Ala Pro Ala Pro Leu Glu Glu Ala Pro Trp Pro
            290                 295                 300

Pro Pro Glu Gly Ala Phe Val Gly Phe Val Leu Ser Arg Pro Glu Pro
305                 310                 315                 320

Met Trp Ala Glu Leu Lys Ala Leu Ala Ala Cys Arg Asp Gly Arg Val
                325                 330                 335

His Arg Ala Ala Asp Pro Leu Ala Gly Leu Lys Asp Leu Lys Glu Val
            340                 345                 350

Arg Gly Leu Leu Ala Lys Asp Leu Ala Val Leu Ala Ser Arg Glu Gly
            355                 360                 365

Leu Asp Leu Val Pro Gly Asp Asp Pro Met Leu Leu Ala Tyr Leu Leu
            370                 375                 380

Asp Pro Ser Asn Thr Thr Pro Glu Gly Val Ala Arg Arg Tyr Gly Gly
385                 390                 395                 400

Glu Trp Thr Glu Asp Ala Ala His Arg Ala Leu Leu Ser Glu Arg Leu
                405                 410                 415

His Arg Asn Leu Leu Lys Arg Leu Glu Gly Glu Glu Lys Leu Leu Trp
            420                 425                 430
```

```
Leu Tyr His Glu Val Glu Lys Pro Leu Ser Arg Val Leu Ala His Met
        435                 440                 445
Glu Ala Thr Gly Val Arg Arg Asp Val Ala Tyr Leu Gln Ala Leu Ser
        450                 455                 460
Leu Glu Leu Ala Glu Ile Arg Arg Leu Glu Glu Val Phe Arg
465                 470                 475                 480
Leu Ala Gly His Pro Phe Asn Leu Asn Ser Arg Asp Gln Leu Glu Arg
                485                 490                 495
Val Leu Phe Asp Glu Leu Arg Leu Pro Ala Leu Gly Lys Thr Gln Lys
            500                 505                 510
Thr Gly Lys Arg Ser Thr Ser Ala Ala Val Leu Glu Ala Leu Arg Glu
        515                 520                 525
Ala His Pro Ile Val Glu Lys Ile Leu Gln His Arg Glu Leu Thr Lys
        530                 535                 540
Leu Lys Asn Thr Tyr Val Asp Pro Leu Pro Ser Leu Val His Pro Arg
545                 550                 555                 560
Thr Gly Arg Leu His Thr Arg Phe Asn Gln Thr Ala Thr Ala Thr Gly
                565                 570                 575
Arg Leu Ser Ser Ser Asp Pro Asn Leu Gln Asn Ile Pro Val Arg Thr
            580                 585                 590
Pro Leu Gly Gln Arg Ile Arg Arg Ala Phe Val Ala Glu Ala Gly Trp
        595                 600                 605
Ala Leu Val Ala Leu Asp Tyr Ser Gln Ile Glu Leu Arg Val Leu Ala
        610                 615                 620
His Leu Ser Gly Asp Glu Asn Leu Ile Arg Val Phe Gln Glu Gly Lys
625                 630                 635                 640
Asp Ile His Thr Gln Thr Ala Ser Trp Met Phe Gly Val Pro Pro Glu
                645                 650                 655
Ala Val Asp Pro Leu Met Arg Arg Ala Ala Lys Thr Val Asn Phe Gly
            660                 665                 670
Val Leu Tyr Gly Met Ser Ala His Arg Leu Ser Gln Glu Leu Ala Ile
        675                 680                 685
Pro Tyr Glu Glu Ala Val Ala Phe Ile Glu Arg Tyr Phe Gln Ser Phe
        690                 695                 700
Pro Lys Val Arg Ala Trp Ile Glu Lys Thr Leu Glu Glu Gly Arg Lys
705                 710                 715                 720
Arg Gly Tyr Val Glu Thr Leu Phe Gly Arg Arg Arg Tyr Val Pro Asp
                725                 730                 735
Leu Asn Ala Arg Val Lys Ser Val Arg Glu Ala Ala Glu Arg Met Ala
            740                 745                 750
Phe Asn Met Pro Val Gln Gly Thr Ala Ala Asp Leu Met Lys Leu Ala
        755                 760                 765
Met Val Lys Leu Phe Pro Arg Leu Arg Glu Met Gly Ala Arg Met Leu
        770                 775                 780
Leu Gln Val His Asn Glu Leu Leu Glu Ala Pro Gln Ala Arg Ala
785                 790                 795                 800
Glu Glu Val Ala Ala Leu Ala Lys Glu Ala Met Glu Lys Ala Tyr Pro
                805                 810                 815
Leu Ala Val Pro Leu Glu Val Glu Val Gly Met Gly Glu Asp Trp Leu
            820                 825                 830
Ser Ala Lys Gly His His His His His His
        835                 840
```

<210> SEQ ID NO 16
<211> LENGTH: 31
<212> TYPE: DNA
<213> ORGANISM: Artificial Sequence
<220> FEATURE:
<223> OTHER INFORMATION: Synthetic

<400> SEQUENCE: 16
gcctgcaggg gcggccgcgt gcaccggggc a                                    31

<210> SEQ ID NO 17
<211> LENGTH: 26
<212> TYPE: DNA
<213> ORGANISM: Artificial Sequence
<220> FEATURE:
<223> OTHER INFORMATION: Synthetic

<400> SEQUENCE: 17
ctcctggacc cttcgaacac cacccc                                          26

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
gtcctggccc atatggaggc cac                                             23

<210> SEQ ID NO 19
<211> LENGTH: 2526
<212> TYPE: DNA
<213> ORGANISM: Thermus thermophilus

<400> SEQUENCE: 19
atgaattccg aggcgatgct tccgctcttt gaacccaaag gccgggtcct cctggtggac      60
ggccaccacc tggcctaccg caccttcttc gccctgaagg gcctcaccac gagccggggc     120
gaaccggtgc aggcggtcta cggcttcgcc aagagcctcc tcaaggccct gaaggaggac     180
gggtacaagg ccgtcttcgt ggtctttgac gccaaggccc cctccttccg ccacgaggcc     240
tacgaggcct acaaggcggg gagggccccg accccgagg acttcccccg gcagctcgcc     300
ctcatcaagg agctggtgga cctcctgggg tttacccgcc tcgaggtccc cggctacgag     360
gcggacgacg ttctcgccac cctggccaag aaggcggaaa aggagggggta cgaggtgcgc     420
atcctcaccg ccgaccgcga cctctaccaa ctcgtctccg accgcgtcgc cgtcctccac     480
cccgagggcc acctcatcac cccggagtgg ctttgggaga agtacggcct caggccggag     540
cagtgggtgg acttccgcgc cctcgtgggg gaccccctccg acaacctccc cggggtcaag     600
ggcatcgggg agaagaccgc cctcaagctc ctcaaggagt ggggaagcct ggaaaacctc     660
ctcaagaacc tggaccgggt aaagccagaa acgtccggg agaagatcaa ggcccacctg     720
gaagacctca ggctctcctt ggagctctcc cgggtgcgca ccgacctccc cctggaggtg     780
gacctcgccc aggggcggga gcccgaccgg aggggcttag ggccttcct ggagaggctg     840
gagttcggca gcctcctcca cgagttcggc ctcctggagg ccccgccccc cctggaggag     900
gcccctggc cccgccgga aggggccttc gtgggcttcg tcctctcccg ccccgagccc     960
atgtgggcgg agcttaaagc cctggccgcc tgcaggggcg gccgcgtgca ccggggcagca    1020
gacccccttgg cggggctaaa ggacctcaag gaggtccggg gcctcctcgc caaggacctc    1080

-continued

```
gccgtcttgg cctcgaggga ggggctagac ctcgtgcccg gggacgaccc catgctcctc    1140
gcctacctcc tggacccttc gaacaccacc cccgaggggg tggcgcggcg ctacgggggg    1200
gagtggacgg aggacgccgc ccaccgggcc ctcctctcgg agaggctcca tcggaacctc    1260
cttaagcgcc tcgaggggga ggagaagctc ctttggctct accacgaggt ggaaaagccc    1320
ctctcccggg tcctggccca tatggaggcc accggggtac ggcgggacgt ggcctacctt    1380
caggcccttt cctggagct gcgaggag atccgccgcc tcgaggagga ggtcttccgc        1440
ttggcgggcc accccttcaa cctcaactcc cgggaccagc tggaaagggt gctctttgac    1500
gagcttaggc ttcccgcctt ggggaagacg caaaagacag gcaagcgctc caccagcgcc    1560
gcggtgctgg aggccctacg ggaggcccac cccatcgtgg agaagatcct ccagcaccgg    1620
gagctcacca agctcaagaa cacctacgtg dacccctcc caagcctcgt ccacccgagg    1680
acgggccgcc tccacacccg cttcaaccag acggccacgg ccacggggag cttagtagc    1740 tccgaccccca acctgcagaa catccccgtc cgcacccct tgggccagag gatccgccgg    1800
gccttcgtgg ccgaggcggg ttgggcgttg gtggccctgg actatagcca gatagagctc    1860
cgcgtcctcg cccacctctc cggggacgaa aacctgatca gggtcttcca ggaggggaag    1920
gacatccaca cccagaccgc aagctggatg ttcggcgtcc cccggaggc cgtggacccc    1980 ctgatgcgcc gggcggccaa gacggtgaac ttcggcgtcc tctacggcat gtccgcccat    2040
aggctctccc aggagcttgc catcccctac gaggaggcgg tggcctttat agagcgctac    2100
ttccaaagct tccccaaggt gcgggcctgg atagaaaaga ccctggagga ggggaggaag    2160
cggggctacg tggaaaccct cttcggaaga aggcgctacg tgcccgacct caacgcccgg    2220
gtgaagagcg tcagggaggc cgcggagcgc atggccttca acatgcccgt ccagggcacc    2280
gccgccgacc tcatgaagct cgccatggtg aagctcttcc cccgcctccg ggagatgggg    2340
gcccgcatgc tcctccaggt ccacaacgag ctcctcctgg aggcccccca agcgcgggcc    2400
gaggaggtgg cggctttggc caaggaggcc atggagaagg cctatcccct cgccgtgccc    2460
ctggaggtgg aggtgggat gggggaggac tggctttccg ccaagggtca ccaccaccac    2520
caccac                                                              2526
```

<210> SEQ ID NO 20
<211> LENGTH: 842
<212> TYPE: PRT
<213> ORGANISM: Thermus thermophilus

<400> SEQUENCE: 20

```
Met Asn Ser Glu Ala Met Leu Pro Leu Phe Glu Pro Lys Gly Arg Val
1               5                   10                  15

Leu Leu Val Asp Gly His His Leu Ala Tyr Arg Thr Phe Phe Ala Leu
                20                  25                  30

Lys Gly Leu Thr Thr Ser Arg Gly Glu Pro Val Gln Ala Val Tyr Gly
            35                  40                  45

Phe Ala Lys Ser Leu Leu Lys Ala Leu Lys Glu Asp Gly Tyr Lys Ala
        50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
            100                 105                 110
```

-continued

```
Arg Leu Glu Val Pro Gly Tyr Glu Ala Asp Val Leu Ala Thr Leu
        115                 120                 125

Ala Lys Lys Ala Glu Lys Glu Gly Tyr Glu Val Arg Ile Leu Thr Ala
130                 135                 140

Asp Arg Asp Leu Tyr Gln Leu Val Ser Asp Arg Val Ala Val Leu His
        145                 150                 155             160

Pro Glu Gly His Leu Ile Thr Pro Glu Trp Leu Trp Glu Lys Tyr Gly
                    165                 170                 175

Leu Arg Pro Glu Gln Trp Val Asp Phe Arg Ala Leu Val Gly Asp Pro
            180                 185                 190

Ser Asp Asn Leu Pro Gly Val Lys Gly Ile Gly Glu Lys Thr Ala Leu
        195                 200                 205

Lys Leu Leu Lys Glu Trp Gly Ser Leu Glu Asn Leu Leu Lys Asn Leu
    210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270

Leu Arg Ala Phe Leu Glu Arg Leu Glu Phe Gly Ser Leu Leu His Glu
        275                 280                 285

Phe Gly Leu Leu Glu Ala Pro Ala Pro Leu Glu Glu Ala Pro Trp Pro
    290                 295                 300

Pro Pro Glu Gly Ala Phe Val Gly Phe Val Leu Ser Arg Pro Glu Pro
305                 310                 315                 320

Met Trp Ala Glu Leu Lys Ala Leu Ala Ala Cys Arg Gly Gly Arg Val
                325                 330                 335

His Arg Ala Ala Asp Pro Leu Ala Gly Leu Lys Asp Leu Lys Glu Val
            340                 345                 350

Arg Gly Leu Leu Ala Lys Asp Leu Ala Val Leu Ala Ser Arg Glu Gly
        355                 360                 365

Leu Asp Leu Val Pro Gly Asp Asp Pro Met Leu Leu Ala Tyr Leu Leu
    370                 375                 380

Asp Pro Ser Asn Thr Thr Pro Glu Gly Val Ala Arg Arg Tyr Gly Gly
385                 390                 395                 400

Glu Trp Thr Glu Asp Ala Ala His Arg Ala Leu Leu Ser Glu Arg Leu
                405                 410                 415

His Arg Asn Leu Leu Lys Arg Leu Glu Gly Glu Lys Leu Leu Trp
            420                 425                 430

Leu Tyr His Glu Val Glu Lys Pro Leu Ser Arg Val Leu Ala His Met
    435                 440                 445

Glu Ala Thr Gly Val Arg Arg Asp Val Ala Tyr Leu Gln Ala Leu Ser
450                 455                 460

Leu Glu Leu Ala Glu Glu Ile Arg Arg Leu Glu Glu Glu Val Phe Arg
465                 470                 475                 480

Leu Ala Gly His Pro Phe Asn Leu Asn Ser Arg Asp Gln Leu Glu Arg
                485                 490                 495

Val Leu Phe Asp Glu Leu Arg Leu Pro Ala Leu Gly Lys Thr Gln Lys
            500                 505                 510

Thr Gly Lys Arg Ser Thr Ser Ala Ala Val Leu Glu Ala Leu Arg Glu
        515                 520                 525

Ala His Pro Ile Val Glu Lys Ile Leu Gln His Arg Glu Leu Thr Lys
```

```
            530                 535                 540
Leu Lys Asn Thr Tyr Val Asp Pro Leu Pro Ser Leu Val His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
                580                 585                 590

Pro Leu Gly Gln Arg Ile Arg Arg Ala Phe Val Ala Glu Ala Gly Trp
                595                 600                 605

Ala Leu Val Ala Leu Asp Tyr Ser Gln Ile Glu Leu Arg Val Leu Ala
                610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
                645                 650                 655

Ala Val Asp Pro Leu Met Arg Arg Ala Ala Lys Thr Val Asn Phe Gly
                660                 665                 670

Val Leu Tyr Gly Met Ser Ala His Arg Leu Ser Gln Glu Leu Ala Ile
                675                 680                 685

Pro Tyr Glu Glu Ala Val Ala Phe Ile Glu Arg Tyr Phe Gln Ser Phe
                690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Tyr Val Pro Asp
                725                 730                 735

Leu Asn Ala Arg Val Lys Ser Val Arg Glu Ala Ala Glu Arg Met Ala
                740                 745                 750

Phe Asn Met Pro Val Gln Gly Thr Ala Ala Asp Leu Met Lys Leu Ala
                755                 760                 765

Met Val Lys Leu Phe Pro Arg Leu Arg Glu Met Gly Ala Arg Met Leu
                770                 775                 780

Leu Gln Val His Asn Glu Leu Leu Leu Glu Ala Pro Gln Ala Arg Ala
785                 790                 795                 800

Glu Glu Val Ala Ala Leu Ala Lys Glu Ala Met Glu Lys Ala Tyr Pro
                805                 810                 815

Leu Ala Val Pro Leu Glu Val Glu Val Gly Met Gly Glu Asp Trp Leu
                820                 825                 830

Ser Ala Lys Gly His His His His
                835                 840

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
caggaggagc tcgttggcga cctggaggag                                    30

<210> SEQ ID NO 22
<211> LENGTH: 2526
<212> TYPE: DNA
<213> ORGANISM: Thermus thermophilus

<400> SEQUENCE: 22
```

```
atgaattccg aggcgatgct tccgctctt gaacccaaag gccgggtcct cctggtggac    60
ggccaccacc tggcctaccg caccttcttc gccctgaagg gcctcaccac gagccggggc   120
gaaccggtgc aggcggtcta cggcttcgcc aagagcctcc tcaaggccct gaaggaggac   180
gggtacaagg ccgtcttcgt ggtctttgac gccaaggccc cctccttccg ccacgaggcc   240
tacgaggcct acaaggcggg gagggccccg acccccgagg acttccccg gcagctcgcc    300
ctcatcaagg agctggtgga cctcctgggg tttacccgcc tcgaggtccc cggctacgag   360
gcggacgacg ttctcgccac cctggccaag aaggcggaaa aggaggggta cgaggtgcgc   420
atcctcaccc ccgaccgcga cctctaccaa ctcgtctccg accgcgtcgc cgtcctccac   480
cccgagggcc acctcatcac cccggagtgg cttgggaga agtacggcct caggccggag   540
cagtgggtgg acttccgcgc cctcgtgggg gacccctccg caacctccc cggggtcaag   600
ggcatcgggg agaagaccgc cctcaagctc tcaaggagt ggggaagcct ggaaaacctc    660
ctcaagaacc tggaccgggt aaagccagaa acgtccggg agaagatcaa ggcccacctg    720
gaagacctca ggctctcctt ggagctctcc cgggtgcgca ccgacctccc cctggaggtg   780
gacctcgccc aggggcggga gcccgaccgg gagggcttta ggccttcct ggagaggctg    840
gagttcggca gcctcctcca cgagttcggc ctcctggagg cccccgcccc cctggaggag   900
gcccctggc cccgccgga aggggccttc gtgggcttcg tcctctcccg ccccgagccc     960
atgtgggcgg agcttaaagc cctggccgcc tgcaggggcg gccgcgtgca ccgggcagca  1020
gaccccttgg cgggctaaa ggacctcaag gaggtccggg gcctcctcgc caaggacctc   1080
gccgtcttgg cctcgaggga ggggctagac ctcgtgcccg gggacgaccc catgctcctc  1140
gcctacctcc tggacccttc gaacaccacc cccgaggggg tggcgcggcg ctacggggg   1200
gagtggacgg aggacgccgc ccaccgggcc ctcctctcgg agaggctcca tcggaacctc  1260
cttaagcgcc tcgaggggga ggagaagctc ctttggctct accacgaggt ggaaaagccc  1320
ctctcccggg tcctggccca tatggaggcc accgggtac ggcgggacgt ggcctacctt   1380
caggcccttt ccctggagct tgcggaggag atccgccgcc tcgaggagga ggtcttccgc  1440
ttggcgggcc accccttcaa cctcaactcc cgggaccagc tggaaagggt gctctttgac  1500
gagcttaggc ttcccgcctt ggggaagacg caaaagacag gcaagcgctc caccagcgcc  1560
gcggtgctgg aggccctacg ggaggcccac cccatcgtgg agaagatcct ccagcaccgg  1620
gagctcacca agctcaagaa cacctacgtg gaccccctcc caagcctcgt ccacccgagg  1680
acgggccgcc tccacacccg cttcaaccag acggccacgg ccacggggag gcttagtagc  1740
tccgacccca acctgcagaa catccccgtc cgcacccct ggggccagag gatccgccgg   1800
gccttcgtgg ccgaggcggg ttggcgttg gtggccctgg actatagcca gatagagctc   1860
cgcgtcctcg cccacctctc cggggacgaa aacctgatca gggtcttcca ggaggggaag  1920
gacatccaca cccagaccgc aagctggatg ttcggcgtcc ccccggaggc cgtggacccc  1980
ctgatgcgcc gggcggccaa gacggtgaac ttcggcgtcc tctacggcat gtccgcccat  2040
aggctctccc caggagcttgc catccctac gaggaggcg tggcctttat agagcgctac   2100
ttccaaagct cccccaaggt gcgggcctgg ataagaaaga ccctggagga ggggaggaag  2160
cggggctacg tggaaaccct cttcggaaga aggcgctacg tgcccgacct caacgcccgg  2220
gtgaagagcg tcagggaggc cgcggagcgc atggccttca acatgcccgt ccagggcacc  2280
gccgccgacc tcatgaagct cgccatggtg aagctcttcc ccgcctccg ggagatgggg  2340
gcccgcatgc tcctccaggt cgccaacgag ctcctcctgg aggcccccca agcgcgggcc  2400
```

-continued

```
gaggaggtgg cggctttggc caaggaggcc atggagaagg cctatcccct cgccgtgccc    2460
ctggaggtgg aggtggggat ggggaggac tggctttccg ccaagggtca ccaccaccac    2520
caccac                                                              2526
```

<210> SEQ ID NO 23
<211> LENGTH: 842
<212> TYPE: PRT
<213> ORGANISM: Thermus thermophilus

<400> SEQUENCE: 23

```
Met Asn Ser Glu Ala Met Leu Pro Leu Phe Glu Pro Lys Gly Arg Val
1               5                   10                  15

Leu Leu Val Asp Gly His His Leu Ala Tyr Arg Thr Phe Phe Ala Leu
            20                  25                  30

Lys Gly Leu Thr Thr Ser Arg Gly Glu Pro Val Gln Ala Val Tyr Gly
        35                  40                  45

Phe Ala Lys Ser Leu Leu Lys Ala Leu Lys Glu Asp Gly Tyr Lys Ala
    50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
            100                 105                 110

Arg Leu Glu Val Pro Gly Tyr Glu Ala Asp Asp Val Leu Ala Thr Leu
        115                 120                 125

Ala Lys Lys Ala Glu Lys Glu Gly Tyr Glu Val Arg Ile Leu Thr Ala
    130                 135                 140

Asp Arg Asp Leu Tyr Gln Leu Val Ser Asp Arg Val Ala Val Leu His
145                 150                 155                 160

Pro Glu Gly His Leu Ile Thr Pro Glu Trp Leu Trp Glu Lys Tyr Gly
                165                 170                 175

Leu Arg Pro Glu Gln Trp Val Asp Phe Arg Ala Leu Val Gly Asp Pro
            180                 185                 190

Ser Asp Asn Leu Pro Gly Val Lys Gly Ile Gly Glu Lys Thr Ala Leu
        195                 200                 205

Lys Leu Leu Lys Glu Trp Gly Ser Leu Glu Asn Leu Leu Lys Asn Leu
    210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270

Leu Arg Ala Phe Leu Glu Arg Leu Glu Phe Gly Ser Leu Leu His Glu
        275                 280                 285

Phe Gly Leu Leu Glu Ala Pro Ala Pro Leu Glu Glu Ala Pro Trp Pro
    290                 295                 300

Pro Pro Glu Gly Ala Phe Val Gly Phe Val Leu Ser Arg Pro Glu Pro
305                 310                 315                 320

Met Trp Ala Glu Leu Lys Ala Leu Ala Ala Cys Arg Gly Gly Arg Val
                325                 330                 335

His Arg Ala Ala Asp Pro Leu Ala Gly Leu Lys Asp Leu Lys Glu Val
```

-continued

```
                340                 345                 350
Arg Gly Leu Leu Ala Lys Asp Leu Ala Val Leu Ala Ser Arg Glu Gly
            355                 360                 365

Leu Asp Leu Val Pro Gly Asp Pro Met Leu Leu Ala Tyr Leu Leu
        370                 375                 380

Asp Pro Ser Asn Thr Thr Pro Glu Gly Val Ala Arg Arg Tyr Gly Gly
385                 390                 395                 400

Glu Trp Thr Glu Asp Ala Ala His Arg Ala Leu Leu Ser Glu Arg Leu
                405                 410                 415

His Arg Asn Leu Leu Lys Arg Leu Glu Gly Glu Glu Lys Leu Leu Trp
            420                 425                 430

Leu Tyr His Glu Val Glu Lys Pro Leu Ser Arg Val Leu Ala His Met
        435                 440                 445

Glu Ala Thr Gly Val Arg Arg Asp Val Ala Tyr Leu Gln Ala Leu Ser
    450                 455                 460

Leu Glu Leu Ala Glu Glu Ile Arg Arg Leu Glu Glu Val Phe Arg
465                 470                 475                 480

Leu Ala Gly His Pro Phe Asn Leu Asn Ser Arg Asp Gln Leu Glu Arg
                485                 490                 495

Val Leu Phe Asp Glu Leu Arg Leu Pro Ala Leu Gly Lys Thr Gln Lys
            500                 505                 510

Thr Gly Lys Arg Ser Thr Ser Ala Ala Val Leu Glu Ala Leu Arg Glu
        515                 520                 525

Ala His Pro Ile Val Glu Lys Ile Leu Gln His Arg Glu Leu Thr Lys
    530                 535                 540

Leu Lys Asn Thr Tyr Val Asp Pro Leu Pro Ser Leu Val His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Val Ala Glu Ala Gly Trp
        595                 600                 605

Ala Leu Val Ala Leu Asp Tyr Ser Gln Ile Glu Leu Arg Val Leu Ala
    610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
                645                 650                 655

Ala Val Asp Pro Leu Met Arg Arg Ala Ala Lys Thr Val Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Val Ala Phe Ile Glu Arg Tyr Phe Gln Ser Phe
    690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Arg Tyr Val Pro Asp
                725                 730                 735

Leu Asn Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765
```

```
Met Val Lys Leu Phe Pro Arg Leu Arg Glu Met Gly Ala Arg Met Leu
        770                 775                 780
Leu Gln Val Ala Asn Glu Leu Leu Glu Ala Pro Gln Ala Arg Ala
785                 790                 795                 800
Glu Glu Val Ala Ala Leu Ala Lys Glu Ala Met Glu Lys Ala Tyr Pro
                805                 810                 815
Leu Ala Val Pro Leu Glu Val Glu Val Gly Met Gly Glu Asp Trp Leu
            820                 825                 830
Ser Ala Lys Gly His His His His His
        835                 840
```

<210> SEQ ID NO 24
<211> LENGTH: 45
<212> TYPE: DNA
<213> ORGANISM: Artificial Sequence
<220> FEATURE:
<223> OTHER INFORMATION: Synthetic

<400> SEQUENCE: 24
ggagcgcttg cctgtcttct tcgtcttctt caaggcggga ggcct          45

<210> SEQ ID NO 25
<211> LENGTH: 2526
<212> TYPE: DNA
<213> ORGANISM: Thermus thermophilus

<400> SEQUENCE: 25
atgaattccg aggcgatgct tccgctcttt gaacccaaag gccgggtcct cctggtggac    60
ggccaccacc tggcctaccg caccttcttc gccctgaagg cctcaccac gagccggggc   120
gaaccggtgc aggcggtcta cggcttcgcc aagagcctcc tcaaggccct gaaggaggac   180
gggtacaagg ccgtcttcgt ggtctttgac gccaaggccc cctccttccg ccacgaggcc   240
tacgaggcct acaaggcggg gagggccccg accccgagg acttccccg gcagctcgcc    300
ctcatcaagg agctggtgga cctcctgggg tttacccgcc tcgaggtccc cggctacgag   360
gcggacgacg ttctcgccac cctggccaag aaggcggaaa aggaggggta cgaggtgcgc   420
atcctcaccg ccgaccgcga cctctaccaa ctcgtctccg accgcgtcgc cgtcctccac   480
cccgagggcc acctcatcac cccggagtgg cttggggaga agtacggcct caggccggag   540
cagtgggtgg acttccgcgc cctcgtgggg gaccccctccg acaacctccc cggggtcaag   600
ggcatcgggg agaagaccgc cctcaagctc ctcaaggagt ggggaagcct ggaaaacctc   660
ctcaagaacc tggaccgggt aaagccagaa aacgtccggg agaagatcaa ggcccacctg   720
gaagacctca ggctctcctt ggagctctcc cgggtgcgca ccgacctccc cctggaggtg   780
gacctcgccc aggggcggga gcccgaccgg gaggggctta ggccttcct ggagaggctg   840
gagttcggca gcctcctcca cgagttcggc ctcctgaggg ccccgccc cctggaggag   900
gccccctggc cccgccgga aggggccttc gtgggcttcg tcctctcccg ccccgagccc   960
atgtgggcg agcttaaagc cctggccgcc tgcaggggcg gcgcgtgca ccgggcagca  1020
gaccccttgg cggggctaaa ggacctcaag gaggtccggg gcctcctcgc caaggacctc  1080
gccgtcttgg cctcgaggga ggggctagac ctcgtgcccg ggacgaccc catgctcctc  1140
gcctacctcc tggacccttc gaacaccacc cccgaggggg tggcgcggcg ctacgggggg  1200
gagtggacgg aggacgccgc ccaccggggcc ctcctctcgg agaggctcca tcggaacctc  1260
cttaagcgcc tcgaggggga ggagaagctc ctttggctct accacgaggt ggaaaagccc  1320
```

-continued

```
ctctcccggg tcctggccca tatggaggcc accggggtac ggcgggacgt ggcctacctt    1380
caggcccttt ccctggagct tgcggaggag atccgccgcc tcgaggagga ggtcttccgc    1440
ttggcgggcc accccttcaa cctcaactcc cgggaccagc tggaaagggt gctcttgac     1500 gagcttaggc ttcccgcctt gaagaagacg aagaagacag gcaagcgctc caccagcgcc    1560
gcggtgctgg aggccctacg ggaggccac cccatcgtgg agaagatcct ccagcaccgg     1620
gagctcacca agctcaagaa cacctacgtg gacccctcc caagcctcgt ccacccgagg     1680
acgggccgcc tccacacccg cttcaaccag acggccacgg ccacggggag cttagtagc     1740 tccgaccca acctgcagaa catccccgtc cgcaccccct gggccagag gatccgccgg      1800 gccttcgtgg ccgaggcggg ttgggcgttg gtggccctgg actatagcca gatagagctc    1860
cgcgtcctcg cccacctctc cggggacgaa aacctgatca gggtcttcca ggaggggaag    1920
gacatccaca cccagaccgc aagctggatg ttcggcgtcc ccccggaggc cgtggacccc    1980
ctgatgcgcc gggcggccaa gacggtgaac ttcggcgtcc tctacggcat gtccgcccat    2040
aggctctccc aggagcttgc catccctac gaggaggcgg tggcctttat agagcgctac      2100
ttccaaagct tccccaaggt gcgggcctgg atagaaaaga ccctggagga ggggaggaag    2160
cggggctacg tggaaaccct cttcggaaga aggcgctacg tgcccgacct caacgcccgg    2220
gtgaagagcg tcagggaggc cgcggagcgc atggccttca acatgcccgt ccagggcacc    2280
gccgccgacc tcatgaagct cgccatggtg aagctcttcc cccgcctccg ggagatgggg    2340
gcccgcatgc tcctccaggt cgccaacgag ctcctcctgg aggcccccca agcgcgggcc    2400
gaggaggtgg cggctttggc caaggaggcc atggagaagg cctatcccct cgccgtgccc    2460
ctggaggtgg aggtggggat ggggaggac tggctttccg ccaagggtca ccaccaccac    2520
caccac                                                               2526
```

<210> SEQ ID NO 26
<211> LENGTH: 842
<212> TYPE: PRT
<213> ORGANISM: Thermus thermophilus

<400> SEQUENCE: 26

```
Met Asn Ser Glu Ala Met Leu Pro Leu Phe Glu Pro Lys Gly Arg Val
1               5                   10                  15

Leu Leu Val Asp Gly His His Leu Ala Tyr Arg Thr Phe Phe Ala Leu
            20                  25                  30

Lys Gly Leu Thr Thr Ser Arg Gly Glu Pro Val Gln Ala Val Tyr Gly
        35                  40                  45

Phe Ala Lys Ser Leu Leu Lys Ala Leu Lys Glu Asp Gly Tyr Lys Ala
    50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
            100                 105                 110

Arg Leu Glu Val Pro Gly Tyr Glu Ala Asp Asp Val Leu Ala Thr Leu
        115                 120                 125

Ala Lys Lys Ala Glu Lys Glu Gly Tyr Glu Val Arg Ile Leu Thr Ala
    130                 135                 140

Asp Arg Asp Leu Tyr Gln Leu Val Ser Asp Arg Val Ala Val Leu His
```

-continued

```
            145                 150                 155                 160
        Pro Glu Gly His Leu Ile Thr Pro Glu Trp Leu Trp Glu Lys Tyr Gly
                        165                 170                 175
        Leu Arg Pro Glu Gln Trp Val Asp Phe Arg Ala Leu Val Gly Asp Pro
                        180                 185                 190
        Ser Asp Asn Leu Pro Gly Val Lys Gly Ile Gly Glu Lys Thr Ala Leu
                        195                 200                 205
        Lys Leu Leu Lys Glu Trp Gly Ser Leu Glu Asn Leu Leu Lys Asn Leu
                        210                 215                 220
        Asp Arg Val Lys Pro Glu Asn Val Arg Glu Lys Ile Lys Ala His Leu
        225                 230                 235                 240
        Glu Asp Leu Arg Leu Ser Leu Glu Leu Ser Arg Val Arg Thr Asp Leu
                        245                 250                 255
        Pro Leu Glu Val Asp Leu Ala Gln Gly Arg Glu Pro Asp Arg Glu Gly
                        260                 265                 270
        Leu Arg Ala Phe Leu Glu Arg Leu Glu Phe Gly Ser Leu Leu His Glu
                        275                 280                 285
        Phe Gly Leu Leu Glu Ala Pro Ala Pro Leu Glu Glu Ala Pro Trp Pro
                        290                 295                 300
        Pro Pro Glu Gly Ala Phe Val Gly Phe Val Leu Ser Arg Pro Glu Pro
        305                 310                 315                 320
        Met Trp Ala Glu Leu Lys Ala Leu Ala Ala Cys Arg Gly Gly Arg Val
                        325                 330                 335
        His Arg Ala Ala Asp Pro Leu Ala Gly Leu Lys Asp Leu Lys Glu Val
                        340                 345                 350
        Arg Gly Leu Leu Ala Lys Asp Leu Ala Val Leu Ala Ser Arg Glu Gly
                        355                 360                 365
        Leu Asp Leu Val Pro Gly Asp Asp Pro Met Leu Leu Ala Tyr Leu Leu
                        370                 375                 380
        Asp Pro Ser Asn Thr Thr Pro Glu Gly Val Ala Arg Arg Tyr Gly Gly
        385                 390                 395                 400
        Glu Trp Thr Glu Asp Ala Ala His Arg Ala Leu Leu Ser Glu Arg Leu
                        405                 410                 415
        His Arg Asn Leu Leu Lys Arg Leu Glu Gly Glu Glu Lys Leu Leu Trp
                        420                 425                 430
        Leu Tyr His Glu Val Glu Lys Pro Leu Ser Arg Val Leu Ala His Met
                        435                 440                 445
        Glu Ala Thr Gly Val Arg Arg Asp Val Ala Tyr Leu Gln Ala Leu Ser
                        450                 455                 460
        Leu Glu Leu Ala Glu Glu Ile Arg Arg Leu Glu Glu Glu Val Phe Arg
        465                 470                 475                 480
        Leu Ala Gly His Pro Phe Asn Leu Asn Ser Arg Asp Gln Leu Glu Arg
                        485                 490                 495
        Val Leu Phe Asp Glu Leu Arg Leu Pro Ala Leu Lys Lys Thr Lys Lys
                        500                 505                 510
        Thr Gly Lys Arg Ser Thr Ser Ala Ala Val Leu Glu Ala Leu Arg Glu
                        515                 520                 525
        Ala His Pro Ile Val Glu Lys Ile Leu Gln His Arg Glu Leu Thr Lys
                        530                 535                 540
        Leu Lys Asn Thr Tyr Val Asp Pro Leu Pro Ser Leu Val His Pro Arg
        545                 550                 555                 560
        Thr Gly Arg Leu His Thr Arg Phe Asn Gln Thr Ala Thr Ala Thr Gly
                        565                 570                 575
```

-continued

Arg Leu Ser Ser Ser Asp Pro Asn Leu Gln Asn Ile Pro Val Arg Thr
            580                 585                 590

Pro Leu Gly Gln Arg Ile Arg Arg Ala Phe Val Ala Glu Ala Gly Trp
        595                 600                 605

Ala Leu Val Ala Leu Asp Tyr Ser Gln Ile Glu Leu Arg Val Leu Ala
610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
                645                 650                 655

Ala Val Asp Pro Leu Met Arg Arg Ala Ala Lys Thr Val Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Val Ala Phe Ile Glu Arg Tyr Phe Gln Ser Phe
    690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Arg Tyr Val Pro Asp
                725                 730                 735

Leu Asn Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765

Met Val Lys Leu Phe Pro Arg Leu Arg Glu Met Gly Ala Arg Met Leu
770                 775                 780

Leu Gln Val Ala Asn Glu Leu Leu Leu Glu Ala Pro Gln Ala Arg Ala
785                 790                 795                 800

Glu Glu Val Ala Ala Leu Ala Lys Glu Ala Met Glu Lys Ala Tyr Pro
                805                 810                 815

Leu Ala Val Pro Leu Glu Val Glu Val Gly Met Gly Glu Asp Trp Leu
            820                 825                 830

Ser Ala Lys Gly His His His His His His
        835                 840

<210> SEQ ID NO 27
<211> LENGTH: 340
<212> TYPE: PRT
<213> ORGANISM: Pyrococcus furiosus

<400> SEQUENCE: 27

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Lys Asp Gly Thr Pro Leu Met
        35                  40                  45

Asp Ser Lys Gly Arg Ile Thr Ser His Leu Ser Gly Leu Phe Tyr Arg
    50                  55                  60

Thr Ile Asn Leu Met Glu Ala Gly Ile Lys Pro Val Tyr Val Phe Asp
65                  70                  75                  80

Gly Glu Pro Pro Glu Phe Lys Lys Lys Glu Leu Glu Lys Arg Arg Glu
                85                  90                  95

Ala Arg Glu Glu Ala Glu Glu Lys Trp Arg Glu Ala Leu Glu Lys Gly

-continued

```
            100                 105                 110
Glu Ile Glu Glu Ala Arg Lys Tyr Ala Gln Arg Ala Thr Arg Val Asn
            115                 120                 125
Glu Met Leu Ile Glu Asp Ala Lys Lys Leu Leu Glu Leu Met Gly Ile
        130                 135                 140
Pro Ile Val Gln Ala Pro Ser Glu Gly Glu Ala Gln Ala Ala Tyr Met
145                 150                 155                 160
Ala Ala Lys Gly Ser Val Tyr Ala Ser Ala Ser Gln Asp Tyr Asp Ser
                165                 170                 175
Leu Leu Phe Gly Ala Pro Arg Leu Val Arg Asn Leu Thr Ile Thr Gly
            180                 185                 190
Lys Arg Lys Leu Pro Gly Lys Asn Val Tyr Val Glu Ile Lys Pro Glu
        195                 200                 205
Leu Ile Ile Leu Glu Glu Val Leu Lys Glu Leu Lys Leu Thr Arg Glu
210                 215                 220
Lys Leu Ile Glu Leu Ala Ile Leu Val Gly Thr Asp Tyr Asn Pro Gly
225                 230                 235                 240
Gly Ile Lys Gly Ile Gly Leu Lys Lys Ala Leu Glu Ile Val Arg His
                245                 250                 255
Ser Lys Asp Pro Leu Ala Lys Phe Gln Lys Gln Ser Asp Val Asp Leu
            260                 265                 270
Tyr Ala Ile Lys Glu Phe Phe Leu Asn Pro Pro Val Thr Asp Asn Tyr
        275                 280                 285
Asn Leu Val Trp Arg Asp Pro Asp Glu Glu Gly Ile Leu Lys Phe Leu
290                 295                 300
Cys Asp Glu His Asp Phe Ser Glu Glu Arg Val Lys Asn Gly Leu Glu
305                 310                 315                 320
Arg Leu Lys Lys Ala Ile Lys Ser Gly Lys Gln Ser Thr Leu Glu Ser
                325                 330                 335
Trp Phe Lys Arg
            340

<210> SEQ ID NO 28
<211> LENGTH: 326
<212> TYPE: PRT
<213> ORGANISM: Methanococcus jannaschii

<400> SEQUENCE: 28

Met Gly Val Gln Phe Gly Asp Phe Ile Pro Lys Asn Ile Ile Ser Phe
1               5                   10                  15
Glu Asp Leu Lys Gly Lys Lys Val Ala Ile Asp Gly Met Asn Ala Leu
            20                  25                  30
Tyr Gln Phe Leu Thr Ser Ile Arg Leu Arg Asp Gly Ser Pro Leu Arg
        35                  40                  45
Asn Arg Lys Gly Glu Ile Thr Ser Ala Tyr Asn Gly Val Phe Tyr Lys
    50                  55                  60
Thr Ile His Leu Leu Glu Asn Asp Ile Thr Pro Ile Trp Val Phe Asp
65                  70                  75                  80
Gly Glu Pro Pro Lys Leu Lys Glu Lys Thr Arg Lys Val Arg Arg Glu
                85                  90                  95
Met Lys Glu Lys Ala Glu Leu Lys Met Lys Glu Ala Ile Lys Lys Glu
            100                 105                 110
Asp Phe Glu Glu Ala Ala Lys Tyr Ala Lys Arg Val Ser Tyr Leu Thr
        115                 120                 125
```

```
Pro Lys Met Val Glu Asn Cys Lys Tyr Leu Leu Ser Leu Met Gly Ile
    130                 135                 140

Pro Tyr Val Glu Ala Pro Ser Glu Gly Glu Ala Gln Ala Ser Tyr Met
145                 150                 155                 160

Ala Lys Lys Gly Asp Val Trp Ala Val Ser Gln Asp Tyr Asp Ala
                165                 170                 175

Leu Leu Tyr Gly Ala Pro Arg Val Val Arg Asn Leu Thr Thr Thr Lys
            180                 185                 190

Glu Met Pro Glu Leu Ile Glu Leu Asn Glu Val Leu Glu Asp Leu Arg
        195                 200                 205

Ile Ser Leu Asp Asp Leu Ile Asp Ile Ala Ile Phe Met Gly Thr Asp
    210                 215                 220

Tyr Asn Pro Gly Gly Val Lys Gly Ile Gly Phe Lys Arg Ala Tyr Glu
225                 230                 235                 240

Leu Val Arg Ser Gly Val Ala Lys Asp Val Leu Lys Lys Glu Val Glu
                245                 250                 255

Tyr Tyr Asp Glu Ile Lys Arg Ile Phe Lys Glu Pro Lys Val Thr Asp
            260                 265                 270

Asn Tyr Ser Leu Ser Leu Lys Leu Pro Asp Lys Glu Gly Ile Ile Lys
        275                 280                 285

Phe Leu Val Asp Glu Asn Asp Phe Asn Tyr Asp Arg Val Lys Lys His
    290                 295                 300

Val Asp Lys Leu Tyr Asn Leu Ile Ala Asn Lys Thr Lys Gln Lys Thr
305                 310                 315                 320

Leu Asp Ala Trp Phe Lys
                325

<210> SEQ ID NO 29
<211> LENGTH: 328
<212> TYPE: PRT
<213> ORGANISM: Methanobacterium thermoautotrophicum

<400> SEQUENCE: 29

Met Gly Val Lys Leu Arg Asp Val Val Ser Pro Arg Arg Ile Arg Leu
1               5                   10                  15

Glu Asp Leu Arg Gly Arg Thr Val Ala Val Asp Ala Ala Asn Thr Leu
            20                  25                  30

Tyr Gln Phe Leu Ser Ser Ile Arg Gln Arg Asp Gly Thr Pro Leu Met
        35                  40                  45

Asp Ser Arg Gly Arg Val Thr Ser His Leu Ser Gly Ile Leu Tyr Arg
    50                  55                  60

Thr Ala Ala Val Met Glu Arg Glu Ile Arg Val Ile Tyr Val Phe Asp
65                  70                  75                  80

Gly Arg Ser His His Leu Lys Gly Glu Thr Val Ser Arg Arg Ala Asp
                85                  90                  95

Ile Arg Lys Lys Ser Glu Val Glu Trp Lys Arg Ala Leu Glu Gly Gly
            100                 105                 110

Asp Ile Asp Arg Ala Arg Lys Tyr Ala Val Arg Ser Ser Arg Met Ser
        115                 120                 125

Ser Glu Ile Leu Glu Ser Ser Lys Arg Leu Leu Glu Leu Leu Gly Ile
    130                 135                 140

Pro Tyr Val Gln Ala Pro Gly Glu Gly Glu Ala Gln Ala Ser Tyr Met
145                 150                 155                 160

Val Lys Met Gly Asp Ala Trp Ala Val Ala Ser Gln Asp Tyr Asp Cys
                165                 170                 175
```

```
Leu Leu Phe Gly Ala Pro Arg Val Val Arg Lys Val Thr Leu Ser Gly
            180                 185                 190

Lys Leu Glu Asp Pro His Ile Ile Glu Leu Glu Ser Thr Leu Arg Ala
            195                 200                 205

Leu Ser Ile Ser His Thr Gln Leu Val Asp Met Ala Leu Leu Val Gly
            210                 215                 220

Thr Asp Phe Asn Glu Gly Val Lys Gly Tyr Gly Ala Arg Arg Gly Leu
225                 230                 235                 240

Lys Leu Ile Arg Glu Lys Gly Asp Ile Phe Lys Val Ile Arg Asp Leu
            245                 250                 255

Glu Ala Asp Ile Gly Gly Asp Pro Gln Val Leu Arg Arg Ile Phe Leu
            260                 265                 270

Glu Pro Glu Val Ser Glu Asp Tyr Glu Ile Arg Trp Arg Lys Pro Asp
            275                 280                 285

Val Glu Gly Val Ile Glu Phe Leu Cys Thr Glu His Gly Phe Ser Glu
            290                 295                 300

Asp Arg Val Arg Asp Ala Leu Lys Lys Phe Glu Gly Ala Ser Ser Thr
305                 310                 315                 320

Gln Lys Ser Leu Glu Asp Trp Phe
            325

<210> SEQ ID NO 30
<211> LENGTH: 336
<212> TYPE: PRT
<213> ORGANISM: Archaeoglobus fulgidus

<400> SEQUENCE: 30

Met Gly Ala Asp Ile Gly Asp Leu Phe Glu Arg Glu Val Glu Leu
1               5                   10                  15

Glu Tyr Phe Ser Gly Lys Lys Ile Ala Val Asp Ala Phe Asn Thr Leu
            20                  25                  30

Tyr Gln Phe Ile Ser Ile Ile Arg Gln Pro Asp Gly Thr Pro Leu Lys
            35                  40                  45

Asp Ser Gln Gly Arg Ile Thr Ser His Leu Ser Gly Ile Leu Tyr Arg
50                  55                  60

Val Ser Asn Met Val Glu Val Gly Ile Arg Pro Val Phe Val Phe Asp
65                  70                  75                  80

Gly Glu Pro Pro Glu Phe Lys Lys Ala Glu Ile Glu Glu Arg Lys Lys
            85                  90                  95

Arg Arg Ala Glu Ala Glu Glu Met Trp Ile Ala Ala Leu Gln Ala Gly
            100                 105                 110

Asp Lys Asp Ala Lys Lys Tyr Ala Gln Ala Ala Gly Arg Val Asp Glu
            115                 120                 125

Tyr Ile Val Asp Ser Ala Lys Thr Leu Leu Ser Tyr Met Gly Ile Pro
            130                 135                 140

Phe Val Asp Ala Pro Ser Glu Gly Glu Ala Gln Ala Ala Tyr Met Ala
145                 150                 155                 160

Ala Lys Gly Asp Val Glu Tyr Thr Gly Ser Gln Asp Tyr Asp Ser Leu
            165                 170                 175

Leu Phe Gly Ser Pro Arg Leu Ala Arg Asn Leu Ala Ile Thr Gly Lys
            180                 185                 190

Arg Lys Leu Pro Gly Lys Asn Val Tyr Val Asp Val Lys Pro Glu Ile
            195                 200                 205

Ile Ile Leu Glu Ser Asn Leu Lys Arg Leu Gly Leu Thr Arg Glu Gln
```

|     |     |     |     |     |     |     |     |     |     |     |     |
|---|---|---|---|---|---|---|---|---|---|---|---|
|     |     |     |     |     | 210 |     |     | 215 |     |     | 220 |
| Leu | Ile | Asp | Ile | Ala | Ile | Leu | Val | Gly | Thr | Asp | Tyr | Asn | Glu | Gly | Val |
| 225 |     |     |     |     | 230 |     |     |     |     | 235 |     |     |     |     | 240 |
| Lys | Gly | Val | Gly | Val | Lys | Lys | Ala | Leu | Asn | Tyr | Ile | Lys | Thr | Tyr | Gly |
|     |     |     |     | 245 |     |     |     |     | 250 |     |     |     |     | 255 |     |
| Asp | Ile | Phe | Arg | Ala | Leu | Lys | Ala | Leu | Lys | Val | Asn | Ile | Asp | His | Val |
|     |     |     |     | 260 |     |     |     |     | 265 |     |     |     |     | 270 |     |
| Glu | Glu | Ile | Arg | Asn | Phe | Phe | Leu | Asn | Pro | Pro | Val | Thr | Asp | Asp | Tyr |
|     |     |     | 275 |     |     |     |     | 280 |     |     |     |     | 285 |     |     |
| Arg | Ile | Glu | Phe | Arg | Glu | Pro | Asp | Phe | Glu | Lys | Ala | Ile | Glu | Phe | Leu |
|     |     | 290 |     |     |     |     | 295 |     |     |     |     | 300 |     |     |     |
| Cys | Glu | Glu | His | Asp | Phe | Ser | Arg | Glu | Arg | Val | Glu | Lys | Ala | Leu | Glu |
| 305 |     |     |     |     | 310 |     |     |     |     | 315 |     |     |     |     | 320 |
| Lys | Leu | Lys | Ala | Leu | Lys | Ser | Thr | Gln | Ala | Thr | Leu | Glu | Arg | Trp | Phe |
|     |     |     |     | 325 |     |     |     |     | 330 |     |     |     |     | 335 |     |

<210> SEQ ID NO 31
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: The n at this position can be a, c, t, or g.
<220> FEATURE:
<221> NAME/KEY: misc_feature
<222> LOCATION: (27)..(27)
<223> OTHER INFORMATION: The n at this position can be a, c, t, or g.

<400> SEQUENCE: 31
atctctagca ctgctgtntt ygayggn                                    27

<210> SEQ ID NO 32
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: The n at this position can be a, c, t, or g.
<220> FEATURE:
<221> NAME/KEY: misc_feature
<222> LOCATION: (28)..(28)
<223> OTHER INFORMATION: The n at this position can be a, c, t, or g.

<400> SEQUENCE: 32
gatctctagc actgctgarg gngargcnca r                               31

<210> SEQ ID NO 33
<211> LENGTH: 28
<212> TYPE: DNA
<213> ORGANISM: Artificial Sequence
<220> FEATURE:
<223> OTHER INFORMATION: Synthetic

<400> SEQUENCE: 33
gatctctagc actgctcarg aytaygay                                   28

<210> SEQ ID NO 34
<211> LENGTH: 31
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The n at this position can be a, c, t, or g.
<220> FEATURE:
<221> NAME/KEY: misc_feature
<222> LOCATION: (26)..(26)
<223> OTHER INFORMATION: The n at this position can be a, c, t, or g.

<400> SEQUENCE: 34
cttaaggtag gactacytgn gcytcnccyt c                                       31

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
ttaaggtagg actacytcrt aytcytgrct                                         30

<210> SEQ ID NO 36
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(28)
<223> OTHER INFORMATION: The n at this position can be a, c, t, or g.

<400> SEQUENCE: 36
ttaaggtagg actacytcrt aytcytgnga                                         30

<210> SEQ ID NO 37
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: The n at this position can be a, c, t, or g.
<220> FEATURE:
<221> NAME/KEY: misc_feature
<222> LOCATION: (28)..(28)
<223> OTHER INFORMATION: The n at this position can be a, c, t, or g.

<400> SEQUENCE: 37
ttaaggtagg actacrttrw artcngtncc                                         30

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
gatctctagc actgct                                                        16

<210> SEQ ID NO 39
<211> LENGTH: 17
```

```
<212> TYPE: DNA
<213> ORGANISM: Artificial Sequence
<220> FEATURE:
<223> OTHER INFORMATION: Synthetic

<400> SEQUENCE: 39
ccttaaggta ggactac                                                   17

<210> SEQ ID NO 40
<211> LENGTH: 27
<212> TYPE: DNA
<213> ORGANISM: Artificial Sequence
<220> FEATURE:
<223> OTHER INFORMATION: Synthetic

<400> SEQUENCE: 40
tatcgcagcg atccacttct cctctgc                                        27

<210> SEQ ID NO 41
<211> LENGTH: 27
<212> TYPE: DNA
<213> ORGANISM: Artificial Sequence
<220> FEATURE:
<223> OTHER INFORMATION: Synthetic

<400> SEQUENCE: 41
cttaaacggc aacctgagaa ggcttgg                                        27

<210> SEQ ID NO 42
<211> LENGTH: 28
<212> TYPE: DNA
<213> ORGANISM: Artificial Sequence
<220> FEATURE:
<223> OTHER INFORMATION: Synthetic

<400> SEQUENCE: 42
ctatctcctt ctgcttgaaa acaggagg                                       28

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
acaagggaac agctcgtcga tatcgcg                                        27

<210> SEQ ID NO 44
<211> LENGTH: 32
<212> TYPE: DNA
<213> ORGANISM: Artificial Sequence
<220> FEATURE:
<223> OTHER INFORMATION: Synthetic

<400> SEQUENCE: 44
taacgaattc ggtgcagaca taggcgaact ac                                  32

<210> SEQ ID NO 45
<211> LENGTH: 33
<212> TYPE: DNA
<213> ORGANISM: Artificial Sequence
<220> FEATURE:
<223> OTHER INFORMATION: Synthetic

<400> SEQUENCE: 45
```

```
cggtgtcgac tcaggaaaac cacctctcaa gcg                                    33
```

<210> SEQ ID NO 46
<211> LENGTH: 37
<212> TYPE: DNA
<213> ORGANISM: Artificial Sequence
<220> FEATURE:
<223> OTHER INFORMATION: Synthetic

<400> SEQUENCE: 46

```
cacaggaaac agaccatggg tgcagacata ggcgaac                                37
```

<210> SEQ ID NO 47
<211> LENGTH: 1017
<212> TYPE: DNA
<213> ORGANISM: Archaeoglobus veneficus

<400> SEQUENCE: 47

```
atgggtgcag acataggcga actactcgag agagaagaag ttgaacttga gtacttctcc      60
gggagaaaaa tagctattga tgcttttaac actctttacc agttcatatc tatcataagg     120
caacctgacg gcactccttt gaaggattct cagggtagaa tgacctcaca cctctccggc     180
atcctgtacc gcgtgtcaaa catgatcgag gttggaatga cccatttt cgttttcgat      240
ggtgagcctc ctgttttcaa gcagaaggag atagaggaac gaaaggaaag aagagctgaa     300
gcagaggaga agtggatcgc tgcgatagag agaggagaga agtacgcaaa gaagtacgct     360
caggcagcgg cgagggttga tgaatacatc gtcgagtcgt caagaagct gcttgagtat     420
atgggagttc catgggttca ggcgccgagt gagggagagg cacaggctgc atacatggca     480
gcgaagggcg atgtagattt tactggctcg caggattacg actcgcttct cttcggcagc     540
ccaaagcttg caagaaatct cgcgattact ggaaagagga agctgcccgg aaagaatgtt     600
tacgttgagg tcaaaccaga gataatagac ttaaacggca acctgagaag gcttggaata     660
acaagggaac agctcgtcga tatcgcgttg ctcgtgggaa cggactacaa cgaaggagtg     720
aagggcgttg gggtcaagaa ggcctacaag tacataaaaa cctacggaga tgttttcaaa     780
gctctcaagg ccttaaaggt agagcaggag aacatagagg agataagaaa cttcttcctg     840
aacccgcctg ttacgaacaa ctacagcctc cacttcggaa agccagacga tgagaagatt     900
atcgagttcc tgtgtgaaga gcacgacttt agcaaggata gggtagagaa ggccgttgag     960
aagctgaaag caggaatgca agcctcgcaa tcaacgcttg agaggtggtt ttcctga      1017
```

<210> SEQ ID NO 48
<211> LENGTH: 338
<212> TYPE: PRT
<213> ORGANISM: Archaeoglobus veneficus

<400> SEQUENCE: 48

```
Met Gly Ala Asp Ile Gly Glu Leu Leu Glu Arg Glu Glu Val Glu Leu
1               5                   10                  15

Glu Tyr Phe Ser Gly Arg Lys Ile Ala Ile Asp Ala Phe Asn Thr Leu
            20                  25                  30

Tyr Gln Phe Ile Ser Ile Ile Arg Gln Pro Asp Gly Thr Pro Leu Lys
        35                  40                  45

Asp Ser Gln Gly Arg Met Thr Ser His Leu Ser Gly Ile Leu Tyr Arg
    50                  55                  60

Val Ser Asn Met Ile Glu Val Gly Met Arg Pro Ile Phe Val Phe Asp
65                  70                  75                  80
```

```
Gly Glu Pro Pro Val Phe Lys Gln Lys Glu Ile Glu Arg Lys Glu
                 85                  90                  95

Arg Arg Ala Glu Ala Glu Lys Trp Ile Ala Ala Ile Glu Arg Gly
            100                 105                 110

Glu Lys Tyr Ala Lys Lys Tyr Ala Gln Ala Ala Ala Arg Val Asp Glu
        115                 120                 125

Tyr Ile Val Glu Ser Ser Lys Lys Leu Leu Glu Tyr Met Gly Val Pro
130                 135                 140

Trp Val Gln Ala Pro Ser Glu Gly Glu Ala Gln Ala Ala Tyr Met Ala
145                 150                 155                 160

Ala Lys Gly Asp Val Asp Phe Thr Gly Ser Gln Asp Tyr Asp Ser Leu
                165                 170                 175

Leu Phe Gly Ser Pro Lys Leu Ala Arg Asn Leu Ala Ile Thr Gly Lys
                180                 185                 190

Arg Lys Leu Pro Gly Lys Asn Val Tyr Val Glu Val Lys Pro Glu Ile
                195                 200                 205

Ile Asp Leu Asn Gly Asn Leu Arg Arg Leu Gly Ile Thr Arg Glu Gln
210                 215                 220

Leu Val Asp Ile Ala Leu Leu Val Gly Thr Asp Tyr Asn Glu Gly Val
225                 230                 235                 240

Lys Gly Val Gly Val Lys Lys Ala Tyr Lys Tyr Ile Lys Thr Tyr Gly
                245                 250                 255

Asp Val Phe Lys Ala Leu Lys Ala Leu Lys Val Glu Gln Glu Asn Ile
                260                 265                 270

Glu Glu Ile Arg Asn Phe Phe Leu Asn Pro Pro Val Thr Asn Asn Tyr
        275                 280                 285

Ser Leu His Phe Gly Lys Pro Asp Asp Glu Lys Ile Ile Glu Phe Leu
        290                 295                 300

Cys Glu Glu His Asp Phe Ser Lys Asp Arg Val Glu Lys Ala Val Glu
305                 310                 315                 320

Lys Leu Lys Ala Gly Met Gln Ala Ser Gln Ser Thr Leu Glu Arg Trp
                325                 330                 335

Phe Ser

<210> SEQ ID NO 49
<211> LENGTH: 53
<212> TYPE: DNA
<213> ORGANISM: Artificial Sequence
<220> FEATURE:
<223> OTHER INFORMATION: Synthetic

<400> SEQUENCE: 49
cccgtctcgc tggtgaaaag aaaaaccacc ctggcgccca atacgcaaac cgc       53

<210> SEQ ID NO 50
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing either a Cy3 or fluorescein group.
<220> FEATURE:
<221> NAME/KEY: misc_feature
<222> LOCATION: (1)..(2)
<223> OTHER INFORMATION: The T residues at these positions have
      amino-modifiers.
```

```
<220> FEATURE:
<221> NAME/KEY: misc_feature
<222> LOCATION: (22)..(22)
<223> OTHER INFORMATION: The residue at this position is linked to a
      spacer containing either a Cy3 or fluorescein group.

<400> SEQUENCE: 50
ttccagagcc taatttgcca gt                                                  22

<210> SEQ ID NO 51
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing either a Cy3 or fluorescein group.
<220> FEATURE:
<221> NAME/KEY: misc_feature
<222> LOCATION: (1)..(2)
<223> OTHER INFORMATION: The T residues at these positions have
      amino-modifiers.
<220> FEATURE:
<221> NAME/KEY: misc_feature
<222> LOCATION: (22)..(22)
<223> OTHER INFORMATION: The residue at this position is linked to a
      spacer containing either a Cy3 or fluorescein group.

<400> SEQUENCE: 51
ttccagagcc taatttgcca gt                                                  22

<210> SEQ ID NO 52
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing either a TET or fluorescein group.

<400> SEQUENCE: 52
ttccagagcc taatttgcca gta                                                 23

<210> SEQ ID NO 53
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing either a TET or fluorescein group.

<400> SEQUENCE: 53
ttccagagcc taatttgcca gta                                                 23

<210> SEQ ID NO 54
<211> LENGTH: 25
<212> TYPE: DNA
<213> ORGANISM: Artificial Sequence
<220> FEATURE:
<223> OTHER INFORMATION: Synthetic
```

<400> SEQUENCE: 54
cttaccaacg ctaacgagcg tcttg                                              25

<210> SEQ ID NO 55
<211> LENGTH: 14
<212> TYPE: DNA
<213> ORGANISM: Artificial Sequence
<220> FEATURE:
<223> OTHER INFORMATION: Synthetic

<400> SEQUENCE: 55
gctcccgcag acac                                                          14

<210> SEQ ID NO 56
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing a Cy3 group.
<220> FEATURE:
<221> NAME/KEY: misc_feature
<222> LOCATION: (1)..(2)
<223> OTHER INFORMATION: The residues at these positions have amino
      modifications.

<400> SEQUENCE: 56
ttacgccacc agct                                                          14

<210> SEQ ID NO 57
<211> LENGTH: 12
<212> TYPE: DNA
<213> ORGANISM: Artificial Sequence
<220> FEATURE:
<223> OTHER INFORMATION: Synthetic

<400> SEQUENCE: 57
cgctgtctcg ct                                                            12

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
gctcaaggca ctcttgccc                                                     19

<210> SEQ ID NO 59
<211> LENGTH: 63
<212> TYPE: DNA
<213> ORGANISM: Artificial Sequence
<220> FEATURE:
<223> OTHER INFORMATION: Synthetic

<400> SEQUENCE: 59
atgactgaat ataaacttgt ggtagttgga gctggtggcg taggcaagag tgccttgacg         60
ata                                                                      63

<210> SEQ ID NO 60
<211> LENGTH: 45

```
<212> TYPE: DNA
<213> ORGANISM: Artificial Sequence
<220> FEATURE:
<223> OTHER INFORMATION: Synthetic

<400> SEQUENCE: 60
ttttttttta attaggctct ggaaagacgc tcgtgaaacg agcgt                    45

<210> SEQ ID NO 61
<211> LENGTH: 14
<212> TYPE: DNA
<213> ORGANISM: Artificial Sequence
<220> FEATURE:
<223> OTHER INFORMATION: Synthetic

<400> SEQUENCE: 61
cttcggagtt tggg                                                      14

<210> SEQ ID NO 62
<211> LENGTH: 14
<212> TYPE: DNA
<213> ORGANISM: Artificial Sequence
<220> FEATURE:
<223> OTHER INFORMATION: Synthetic

<400> SEQUENCE: 62
cttcggagtt tggg                                                      14

<210> SEQ ID NO 63
<211> LENGTH: 14
<212> TYPE: DNA
<213> ORGANISM: Artificial Sequence
<220> FEATURE:
<223> OTHER INFORMATION: Synthetic

<400> SEQUENCE: 63
cttcggagtt tggg                                                      14

<210> SEQ ID NO 64
<211> LENGTH: 14
<212> TYPE: DNA
<213> ORGANISM: Artificial Sequence
<220> FEATURE:
<223> OTHER INFORMATION: Synthetic

<400> SEQUENCE: 64
cttcggagtt tggg                                                      14

<210> SEQ ID NO 65
<211> LENGTH: 14
<212> TYPE: DNA
<213> ORGANISM: Artificial Sequence
<220> FEATURE:
<223> OTHER INFORMATION: Synthetic

<400> SEQUENCE: 65
cttcggagtt tggg                                                      14

<210> SEQ ID NO 66
<211> LENGTH: 25
<212> TYPE: DNA
<213> ORGANISM: Artificial Sequence
<220> FEATURE:
<223> OTHER INFORMATION: Synthetic

<400> SEQUENCE: 66
```

```
gggttgtgga gtgagtgttc aagta                                          25
```

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67

```
ccatcctaat acgactcact atagggc                                        27
```

<210> SEQ ID NO 68
<211> LENGTH: 21
<212> TYPE: DNA
<213> ORGANISM: Artificial Sequence
<220> FEATURE:
<223> OTHER INFORMATION: Synthetic

<400> SEQUENCE: 68

```
ctcatacagt tacttgtctt c                                              21
```

<210> SEQ ID NO 69
<211> LENGTH: 489
<212> TYPE: RNA
<213> ORGANISM: Homo sapiens

<400> SEQUENCE: 69

```
gaacucacua uagggcucga gcggccgccc gggcaggucc gccaccaaaa ugcagauuuu    60
cgugaaaacc cuuacgggga agaccaucac ccucgagguu gaacccucgg auacgauaga   120
aaauguaaag gccaagaucc aggauaagga aggaauuccu ccugaucagc agagacugau   180
cuuugcuggc aagcagcugg aagauggacg uacuuugucu gacuacaaua uucaaaagga   240
gucuacucuu caucuugugu ugagacuucg uggugugcu aagaaaagga agaagaaguc    300
uuacaccacu cccaagaaga auaagcacaa gagaaagaag guuaagcugg cuguccugaa   360
auauuauaag guggaugaga auggcaaaau uagucgccuu cgucgagagu gcccuucuga   420
ugaauguggu gcuggggugu uuauggcaag ucacuuugac agacauuauu guggcaaaug   480
uugucugac                                                          489
```

<210> SEQ ID NO 70
<211> LENGTH: 52
<212> TYPE: DNA
<213> ORGANISM: Artificial Sequence
<220> FEATURE:
<223> OTHER INFORMATION: Synthetic

<400> SEQUENCE: 70

```
ggaatacgac tcactatagg gaaagtctct gccgcccttc tgtgcctgct gc            52
```

<210> SEQ ID NO 71
<211> LENGTH: 31
<212> TYPE: DNA
<213> ORGANISM: Artificial Sequence
<220> FEATURE:
<223> OTHER INFORMATION: Synthetic

<400> SEQUENCE: 71

```
aatagttaca aaatattcat ttccacaata a                                   31
```

<210> SEQ ID NO 72
<211> LENGTH: 647

```
<212> TYPE: RNA
<213> ORGANISM: Artificial Sequence
<220> FEATURE:
<223> OTHER INFORMATION: Synthetic

<400> SEQUENCE: 72
gggaaagucu cugccgcccu ucugugccug cugcucauag cagccaccuu cauucccaa      60
gggcucgcuc agccagaugc aaucaaugcc ccagucaccu gcuguuauaa cuucaccaau    120
aggaagaucu cagugcagag gcucgcgagc uauagaagaa ucaccagcag caagugaccc    180
aaagaagcug ugaucuucaa gaccauugug gccaaggaga ucugcugaa ccccaagcag     240
aaguggguuc aggauuccau ggaccaccug acaagcaaa cccaaacucc gaagacuuga     300
acacucacuc cacaacccaa gaaucugcag cuaacuuauu uuccccuagc uuuccccaga    360
cacccuguuu uauuuuauua uaaugaauuu uguuuguuga ugugaaacau uaugccuuaa    420
guaauguuaa uucuuauuua aguuauugau guuuuaaguu uaucuuucau gguacuagug    480
uuuuuuagau acagagacuu ggggaaauug cuuuccucu ugaaccacag uucuaccccu     540
gggauguuuu gagggucuuu gcaagaauca uuaauacaaa gaauuuuuuu uaacauucca    600
augcauugcu aaaauauuau uguggaaaug aauauuugu aacuauu                   647

<210> SEQ ID NO 73
<211> LENGTH: 16
<212> TYPE: DNA
<213> ORGANISM: Artificial Sequence
<220> FEATURE:
<223> OTHER INFORMATION: Synthetic

<400> SEQUENCE: 73
ttcttcggag tttggg                                                     16

<210> SEQ ID NO 74
<211> LENGTH: 26
<212> TYPE: DNA
<213> ORGANISM: Artificial Sequence
<220> FEATURE:
<223> OTHER INFORMATION: Synthetic

<400> SEQUENCE: 74
ccgtcacgcc tccttcggag tttggg                                          26

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
aacccaaact ccgaaggagg cgtg                                            24

<210> SEQ ID NO 76
<211> LENGTH: 29
<212> TYPE: DNA
<213> ORGANISM: Artificial Sequence
<220> FEATURE:
<223> OTHER INFORMATION: Synthetic

<400> SEQUENCE: 76
gcgcagtgag aatgaggagg cgtgacggt                                       29

<210> SEQ ID NO 77
```

```
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing a Cy3 group.

<400> SEQUENCE: 77
ctcattctca gtgcg                                                       15

<210> SEQ ID NO 78
<211> LENGTH: 30
<212> TYPE: DNA
<213> ORGANISM: Artificial Sequence
<220> FEATURE:
<223> OTHER INFORMATION: Synthetic

<400> SEQUENCE: 78
aacgaggcgc acctttacat tttctatcgt                                       30

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
ccttccttat cctggatctt ggca                                             24

<210> SEQ ID NO 80
<211> LENGTH: 24
<212> TYPE: DNA
<213> ORGANISM: Artificial Sequence
<220> FEATURE:
<223> OTHER INFORMATION: Synthetic

<400> SEQUENCE: 80
acgatagaaa atgtaaaggt gcgc                                             24

<210> SEQ ID NO 81
<211> LENGTH: 29
<212> TYPE: DNA
<213> ORGANISM: Artificial Sequence
<220> FEATURE:
<223> OTHER INFORMATION: Synthetic

<400> SEQUENCE: 81
cggaagaagc aagtggtgcg cctcgttaa                                        29

<210> SEQ ID NO 82
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      spacer containing a Cy3 group.

<400> SEQUENCE: 82
cacttgcttc ctcc                                                        14
```

```
<210> SEQ ID NO 83
<211> LENGTH: 14
<212> TYPE: DNA
<213> ORGANISM: Artificial Sequence
<220> FEATURE:
<223> OTHER INFORMATION: Synthetic

<400> SEQUENCE: 83
gctcccgcag acac                                                        14

<210> SEQ ID NO 84
<211> LENGTH: 30
<212> TYPE: DNA
<213> ORGANISM: Artificial Sequence
<220> FEATURE:
<223> OTHER INFORMATION: Synthetic

<400> SEQUENCE: 84
caaagaaaag ctgcgtgatg atgaaatcgc                                       30

<210> SEQ ID NO 85
<211> LENGTH: 50
<212> TYPE: DNA
<213> ORGANISM: Artificial Sequence
<220> FEATURE:
<223> OTHER INFORMATION: Synthetic

<400> SEQUENCE: 85
gaaggtgtct gcgggagccg atttcatcat cacgcagctt ttctttgagg                 50
```

CHARGE TAGS AND THE SEPARATION OF NUCLEIC ACID MOLECULES

The present application is a divisional of co-pending U.S. patent application Ser. No. 10/875,094, filed Jun. 23, 2004, which is a divisional of U.S. patent application Ser. No. 09/777,430, filed Feb. 6, 2001, now issued as U.S. Pat. No. 6,780,982, which is a continuation-in-part of U.S. patent application Ser. No. 09/333,145, filed Jun. 14, 1999, now issued as U.S. Pat. No. 6,706,471, which is a continuation-in-part of U.S. patent application Ser. No. 08/682,853, filed Jul. 12, 1996, now U.S. Pat. No. 6,001,567, each of which is herein incorporated by reference in its entirety.

FIELD OF THE INVENTION

The present invention relates to novel phosphoramidites, including positive and neutrally charged compounds. The present invention also provides charge tags for attachment to materials including solid supports and nucleic acids, wherein the charge tags increase or decrease the net charge of the material. The present invention further provides methods for separating and characterizing molecules based on the charge differentials between modified and unmodified materials.

BACKGROUND OF THE INVENTION

Methods for the detection and characterization of specific nucleic acid sequences and sequence variations have been used to detect the presence of viral or bacterial nucleic acid sequences indicative of an infection and to detect the presence of variants or alleles of genes associated with disease and cancers. These methods also find application in the identification of sources of nucleic acids, as for forensic analysis or for paternity determinations. Various methods are known to the art that may be used to detect and characterize specific nucleic acid sequences and sequence variants. Nonetheless, with the completion of the nucleic acid sequencing of the human genome, as well as the genomes of numerous other organisms such as pathogenic organisms, the demand for fast, reliable, cost-effective and user-friendly tests for the detection of specific nucleic acid sequences continues to grow. Importantly, these tests must be able to create a detectable signal from samples that contain very few copies of the sequence of interest.

There are a number of techniques that have been developed for characterizing specific nucleic acid sequences. Examples of detection techniques include the "TaqMan" or nick-translation PCR assay described in U.S. Pat. No. 5,210,015 to Gelfand et al. (the disclosure of which is herein incorporated by reference), the assays described in U.S. Pat. Nos. 4,775,619 and 5,118,605 to Urdea (the disclosures of which are herein incorporated by reference), the catalytic hybridization amplification assay described in U.S. Pat. No. 5,403,711 to Walder and Walder (the disclosure of which is herein incorporated by reference), the cycling probe assay described in U.S. Pat. Nos. 4,876,187 and 5,011,769 to Duck et al., the target-catalyzed oligonucleotide modification assay described in U.S. Pat. Nos. 6,110,677 and 6,121,001 to Western et al. (the disclosures of which are herein incorporated by reference), the SNP detection methods of Orchid Bioscience in U.S. Pat. No. 5,952,174 (the disclosure of which is herein incorporated by reference), the methods of U.S. Pat. No. 5,882,867 to Ullman et al. (the disclosure of which is herein incorporated by reference) the polymerase chain reaction (PCR) described in U.S. Pat. Nos. 4,683,195, 4,683,202, and 4,965,188 to Mullis and Mullis et al. (the disclosures of which are herein incorporated by reference) and the ligase chain reaction (LCR) described in U.S. Pat. Nos. 5,427,930 and 5,494,810 to Birkenmeyer et al. and Barany et al. (the disclosures of which are herein incorporated by reference). The above examples are intended to be illustrative of nucleic acid-based detection assays and do not provide an exhaustive list. Each of these techniques requires a detection step for detecting a reaction product that is indicative of a desired target nucleic acid (e.g., detection of cleavage products, extension products, etc.). While a number of advances have been made in the assay methods and detection instrumentation to improve the sensitively, speed, and cost of detection methods the art is still in need of further improved methods, compositions, and systems to make the assays more sensitive and efficient.

SUMMARY OF THE INVENTION

The present invention relates to novel phosphoramidites, including positive and neutrally charged compounds. The present invention also provides charge tags for attachment to materials including solid supports and nucleic acids, wherein the charge tags increase or decrease the net charge of the material. The present invention further provides methods for separating and characterizing molecules based on the charge differentials between modified and unmodified materials.

For example, the present invention provides a composition comprising a charge tag attached to a nucleic acid molecule (e.g., to a terminal end of a nucleic acid molecule). In some embodiments, the charge tag comprises a phosphate group and a positively charged moiety. In some preferred embodiments, the charge tag further comprises a dye. The present invention is not limited by the position of the individual modular components of the charge tag. For example, in some embodiments, the dye is positioned between the nucleic acid and the positively charged moiety, while in other embodiments, the positively charged moiety is positioned between the nucleic acid and the dye. The present invention is also not limited by the number of each type of component in the charge tag (e.g., the number of dyes, positively charged moieties, etc.). For example, in some embodiments, the charge tag comprises first and second positively charged moieties.

In some embodiments of the present invention, the charge tag has a net positive charge. For example, in some embodiments, the charge tag has a net positive charge of 1, 2, 3, etc. In some embodiments, the charge tag possesses a positive charge only under certain reaction conditions (e.g., pH 6-10).

In some embodiments, the charge tag further comprises one or more nucleotides. In some embodiments, the nucleic acid molecule to which the charge tag is attached contains a sequence that is complementary to a target nucleic acid. In some such embodiments, the one or more nucleotides in the charge are not complementary to the target nucleic acid. In other such embodiments, the nucleic acid comprises a first portion complementary to a target nucleic acid and a second portion that is not complementary to said target nucleic acid, wherein the charge tag is attached to the second portion of the nucleic acid (e.g., to a terminal end of the nucleic acid that is located in the second portion).

In some embodiments of the present invention, the nucleic acid and the charge tag have a combined net neutral charge, wherein the charge tag, in isolation, has a net positive charge. In other embodiments, the nucleic acid and the charge tag have a combined net negative charge, wherein the charge tag has a net positive charge.

The present invention is not limited by the nature of the positively charged moiety of the charge tag. Positively charged moieties include, but are not limited to primary amines, secondary amines, tertiary amines, ammonium groups, positively charged metal groups (e.g., caged ions attached to the charge tag through a linking group), and the like.

In some embodiments, the charge tag further comprises a positively charged phosphoramidite or a neutral phosphoramidite. The present invention is not limited by the nature of the positively charged phosphoramidite or the neutral phosphoramidite. For example, in some embodiments, the charge tags comprise a novel phosphoramidite of the present invention.

For example, the present invention provides a composition comprising a positively charged phosphoramidite. In some embodiments, the positively charged phosphoramidite contains one or more positively charged moieties including, but not limited to, primary amine groups, secondary amine groups, tertiary amine groups, ammonium groups, charged metal ions, and the like. In some embodiments, the phosphoramidite has a net positive charge of one. In some particularly preferred embodiments, the phosphoramidite has the structure:

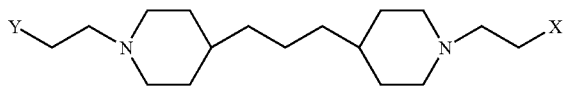

wherein, X is a reactive phosphate group (e.g., $PO_4$) and Y is a protecting group (e.g., dimethoxy trityl [DMT]) and/or a protected group (e.g., DMT-protected hydroxyl group).

The present invention further provides a composition comprising a nucleic acid molecule containing a positively or neutrally charged phosphoramidite. The present invention also provides a composition comprising a charge tag attached to a terminal end of a nucleic acid molecule, wherein the charge tag comprises a positively charged or neutrally charged phosphoramidite. In some preferred embodiments, the positively charged phosphoramide comprises an amine group, wherein the amine group is not further attached to another molecule (a molecule other than the phosphoramidite).

The present invention further provides a composition comprising a neutrally charged phosphoramidite. In some preferred embodiments, the neutrally charged phosphoramidite comprises a nitrogen-containing chemical group selected from the group comprising primary amine, secondary amine, tertiary amine, ammonium group, and charged metal ion. In some embodiments, the composition further comprises a nucleic acid molecule attached to the neutrally charged phosphoramidite. In some preferred embodiments, the nucleic acid molecule is attached to a charge tag comprising the neutrally charged phosphoramidite. The charge tag may further comprise, in any order, other components. For example, the charge tag may further comprise a positively charged phosphoramidite. In some embodiments of the present invention, the charge tag containing the neutrally charged phosphoramidite has a net positive charge. In some particularly preferred embodiments of the present invention, the neutrally charged phosphoramidite has the structure:

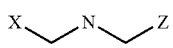

wherein X is a protecting group (e.g., dimethoxy trityl group [DMT]) and/or a protected group (e.g., DMT-protected hydroxyl group), Z is a reactive phosphate, and N comprises an amine group. In some preferred embodiments, the N group is $N-(CH_2)_nCH_3$, wherein n is 0 or a positive integer from 1 to 12.

The present invention also provides a composition comprising a solid support attached to a charge tag. For example, in some embodiments, the charge tag comprises a positively charged moiety and a reactive group configured to allow the charge tag to covalently attach to a nucleic acid molecule. Any of the charge tags described herein, may be attached to the solid support.

The present invention further provides a composition comprising a fluorescent dye directly bonded to a phosphate group, wherein the phosphate group is directly bonded to an amine group. In some embodiments, the composition comprises a charge tag, wherein the fluorescent dye is contained within the charge tag. The present invention is not limited by the nature of the fluorescent dye. However, in some preferred embodiments, the fluorescent dye comprises a Cy dye (e.g., Cy3).

The present invention also provides a mixture comprising a plurality of oligonucleotides attached to charge tags. In some embodiments, each oligonucleotide is attached to a different charge tag. In other embodiments, two or more different oligonucleotides have the same type of charge tag. In some preferred embodiments, each of the charge tags comprises a phosphate group and a positively charged moiety. While not limited by the number of oligonucleotides attached to different charge tags, in some embodiments, the plurality of oligonucleotides comprises four or more oligonucleotides (e.g., 5, 6, 7, . . . , 10, . . . , 50, . . . , 100, . . . ), each attached to a different charge tag. Any of the charge tags described herein are contemplated for use in the mixtures.

The present invention further provides a method of separating nucleic acid molecules, comprising the steps of: a) treating a charge-balanced oligonucleotide containing a charge tag under conditions such that a charge-unbalanced oligonucleotide containing the charge tag is produced, wherein the charge-unbalanced oligonucleotide is contained in a reaction mixture; and b) separating the charge-unbalanced oligonucleotide from the reaction mixture. While the present invention is not limited by the means by which a charge-unbalanced oligonucleotide is generated, in some preferred embodiments, the oligonucleotides are treated with a reactant (e.g., a nuclease). Any of the charge tags described herein are contemplated for use in the method. While the present invention is not limited by the nature of the separation step, contemplated separation steps include, but are not limited to, gel electrophoretic separation, capillary electrophoretic separation, capillary zone electrophoretic separation, and separation is a microchannel.

The present invention also provides a method of separating nucleic acid molecules, comprising the steps of: a) treating a plurality of charge-balanced oligonucleotides, each containing different charge tags, under conditions such that two or more charge-unbalanced oligonucleotides containing the charge tags are produced, wherein the charge-unbalanced oligonucleotides are contained in a reaction mixture; and b) separating the charge-unbalanced oligonucleotides from the reaction mixture. In some preferred embodiments, the separating comprises separating the charge-unbalanced oligonucleotides such that charge-unbalanced oligonucleotides containing different charge tags are separated from one another. Any of the charge tag, oligonucleotide mixtures, and separation methods described herein may be used with this method.

DEFINITIONS

To facilitate an understanding of the present invention, a number of terms and phrases are defined below:

The term "charge-balanced" molecule or oligonucleotide refers to a molecule or oligonucleotide (the input oligonucleotide in a reaction) that has been modified such that the modified molecule or oligonucleotide bears a charge, such that when the modified molecule or oligonucleotide is either reduced in size (e.g., cleaved, shortened, disassociated, unbound, or otherwise altered such that it is part of a complex or molecule having a lower aggregate molecular weight) or increased in sized (e.g., enlarged, elongated, associated, bound, or otherwise altered such that it is part of a complex or molecule having a higher aggregate molecular weight), a resulting product bears a net charge or charge to mass ratio different from the input molecule or oligonucleotide (the resulting molecule thus being a "charge-unbalanced" molecule or oligonucleotide) thereby permitting separation of the input and reacted molecules or oligonucleotides on the basis of charge. The term "charge-balanced" does not imply that the modified or balanced molecule or oligonucleotide has a net neutral charge (although this can be the case). Charge-balancing refers to the design and modification of a molecule or oligonucleotide such that a specific reaction product generated from this input molecule or oligonucleotide can be separated on the basis of charge from the input molecule or oligonucleotide.

For example, in an INVADER oligonucleotide-directed cleavage assay in which the probe oligonucleotide bears the sequence: 5' TTCTTTTCACCAGCGAGACGGG 3' (i.e., SEQ ID NO:1 without the modified bases) and cleavage of the probe occurs between the second and third residues, one possible charge-balanced version of this oligonucleotide would be: 5' Cy3-AminoT-Amino-TCTTTTCACCAGC-GAGAC GGG 3' (SEQ ID NO:1). This modified oligonucleotide bears a net negative charge. After cleavage, the following oligonucleotides are generated: 5' Cy3-AminoT-Amino-T 3' and 5' CTTTTCACCAGCGAGACGGG 3' (residues 3-22 of SEQ ID NO:1). 5' Cy3-AminoT-Amino-T 3' bears a detectable moiety (the positively charged Cy3 dye) and two amino-modified bases. The amino-modified bases and the Cy3 dye contribute positive charges in excess of the negative charges contributed by the phosphate groups and thus the 5' Cy3-AminoT-Amino-T 3' oligonucleotide has a net positive charge. The other, longer cleavage fragment, like the input probe, bears a net negative charge. Because the 5' Cy3-AminoT-Amino-T 3' fragment is separable on the basis of charge from the input probe (the charge-balanced oligonucleotide), it is referred to as a charge-unbalanced oligonucleotide. The longer cleavage products are not generally separated on the basis of charge from the input oligonucleotide as both oligonucleotides bear a net negative charge.

The term "net neutral charge" when used in reference to a molecule or oligonucleotide, including modified oligonucleotides, indicates that the sum of the charges present (e.g., R—NH3+ groups on thymidines, the N3 nitrogen of cytosine, presence or absence or phosphate groups, etc.) under the desired reaction or separation conditions is essentially zero. A molecule or oligonucleotide having a net neutral charge would not migrate in an electrical field.

The term "net positive charge" when used in reference to a molecule or oligonucleotide, including modified oligonucleotides, indicates that the sum of the charges present (e.g., R—NH3+ groups on thymidines, the N3 nitrogen of cytosine, presence or absence or phosphate groups, etc.) under the desired reaction conditions is +1 or greater. A molecule or oligonucleotide having a net positive charge would migrate toward the negative electrode in an electrical field.

The term "net negative charge" when used in reference to a molecule or oligonucleotide, including modified oligonucleotides, indicates that the sum of the charges present (e.g., R—NH3+ groups on thymidines, the N3 nitrogen of cytosine, presence or absence or phosphate groups, etc.) under the desired reaction conditions is −1 or lower. A molecule or oligonucleotide having a net negative charge would migrate toward the positive electrode in an electrical field.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% G+C)$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

The term "label" as used herein refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to cultures, blood, saliva, cerebral spinal fluid, pleural fluid, milk, lymph, sputum, semen, and animal or plant tissue.

As used herein, the term "charge tag" refers to a modular chemical complex that is attached to or to be attached to another molecule, wherein the charge tag has a net charge that differs from the net charge of the other molecule. For example, charge tags may be attached to nucleic acid molecules (e.g., to the terminal end of a nucleic acid molecule). Charge tags contain any number of desired components including, but not limited to, dyes, linker groups, nucleotides, phosphoramidites, phosphonates, phosphate groups, amine groups, fluorescent quencher groups and the like.

In a "mixture comprising a plurality of oligonucleotides with each oligonucleotide attached to a different charge tag," two or more oligonucleotides each possess a distinct charge tag, wherein the chemical makeup of the charge tags differ from one another. A mixture of oligonucleotides, each with a different charge tag, may also comprise additional oligonucleotides. For example, the mixture may contain a first set of oligonucleotides, each with identical first charge tags and a second set of oligonucleotides, each with an identical second charge tags.

As used herein, the term "positively charged moiety" refers to a chemical group or molecule that contains a net positive charge. Positively charged moieties may be attached to or associated with other molecules or materials. A composition containing a positively charged moiety may itself have a net positive charge (because of the positively charged moiety or otherwise), but need not. In some embodiments of the present invention, positively charged moieties include, but are not limited to, amines (e.g., primary, secondary, and tertiary amines). For example, in some embodiments of the present invention, phosphoramidites contain a positively charged moiety comprising an amine. Amine groups are often used as linking chemistries for attaching to or more molecules (e.g., attaching a phosphoramidite to another molecule). However, in some embodiments of the present invention, amine groups are not used as linking groups, but are provided to give a molecule a positive charge. Thus, in some embodiments, the amines are attached to a molecule of interest (e.g., a phosphoramidite), but are not further attached to another molecule (e.g., are not attached to a molecule other than the phosphoramidite).

As used herein, the term "dye" refers to a molecule, compound, or substance that can provide an optically detectable signal (e.g., fluorescent, luminescent, calorimetric, etc). For example, dyes include fluorescent molecules that can be associated with nucleic acid molecules (e.g., Cy3).

As used herein, the term "protecting group" refers to a molecule or chemical group that is covalently attached to a compound to prevent chemical modification of the compound or modification of specific chemical groups of the compound. For example, protecting groups may be attached to a reactive group of a compound to prevent the reactive group from participating in chemical reactions including, for example, intramolecular reactions. In some cases, a protecting group may act as a leaving group, such that when the molecule is added to another compound in a desired synthesis reaction, the protecting group is lost, allowing a reactive group to participate in covalent bonding to the compound. The phosphoramidites of the present invention typically contain one or more protective groups prior to their addition to nucleic acid molecules. For example, the reactive phosphate of the phosphoramidite (i.e., the phosphate group that is covalently attached to another molecule when the phosphoramidite is added to the other molecule) may contain one or more protecting groups. A detailed description of phosphoramidites and their addition to nucleic acid molecules is provided Beaucage and Tyer (Tetrahedron 49:1925 [1993]), herein incorporated by reference in its entirety.

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as nucleic acid molecules, charge tags, and proteins attached to solid supports. A biological material is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linking group." Such spacer molecules are molecules that have a first portion that attaches to the biological material and a second portion that attaches to the solid support. Thus, when attached to the solid support, the spacer molecule separates the solid support and the biological materials, but is attached to both.

As used herein, the term "directly bonded," in reference to two molecules refers to covalent bonding between the two molecules without any intervening linking group or spacer groups that are not part of parent molecules.

As used herein, the terms "linking group" and "linker group" refer to an atom or molecule that links or bonds two entities (e.g., solid supports, oligonucleotides, or other molecules), but that is not a part of either of the individual linked entities.

As used herein, the term "reactant," when referring to an agent that is used to generate charge-unbalanced molecules from charge-balanced molecules, refers to any agent (e.g., enzyme, chemical, physical device, etc.) that can alter a charge-balanced molecule such that a charge-unbalanced molecule is created.

As used herein, the methods of "capillary electrophoresis," "capillary zone electrophoresis," and "microfluids" refer to methods for use in the separation methods of the present invention. The methods of capillary electrophoresis, capillary zone electrophoresis, and microfluids are described in texts and journals including, but not limited to, Baker (1995) Capillary Electrophoresis, Wiley-Interscience, New York, N.Y., Weinberger (2000) Capillary Electrophoresis, Second Edition, Academic Press, San Deigo, Calif., Atamna et al., J. Liq. Chromatogr., 13:2517 (1990), Nishi et al., Anal. Chem., 61:2434 (1989), Terabe et al., Anal. Chem., 56:111 (1984), Bousse et al., Annu. Rev. Biophys. Biomol. Struct., 29:155 (2000), and U.S. Pat. Nos. 5,916,426, 5,807,682, 5,703,222, 5,470,705, 5,777,096, and 5,514,543, each of which is herein incorporated by reference in its entirety.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contain a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

DESCRIPTION OF THE DRAWINGS

FIG. 15 illustrates several possible combinations in the synthesis of a charge balanced probe, using one each of dye, building block, neutral and positively charged phosphoramidites.

FIG. 26A shows a graph comparing the rates of specific signal accumulation in reaction performed for different times, ranging from one to twenty four hours.

DESCRIPTION OF THE INVENTION

Figure 1:
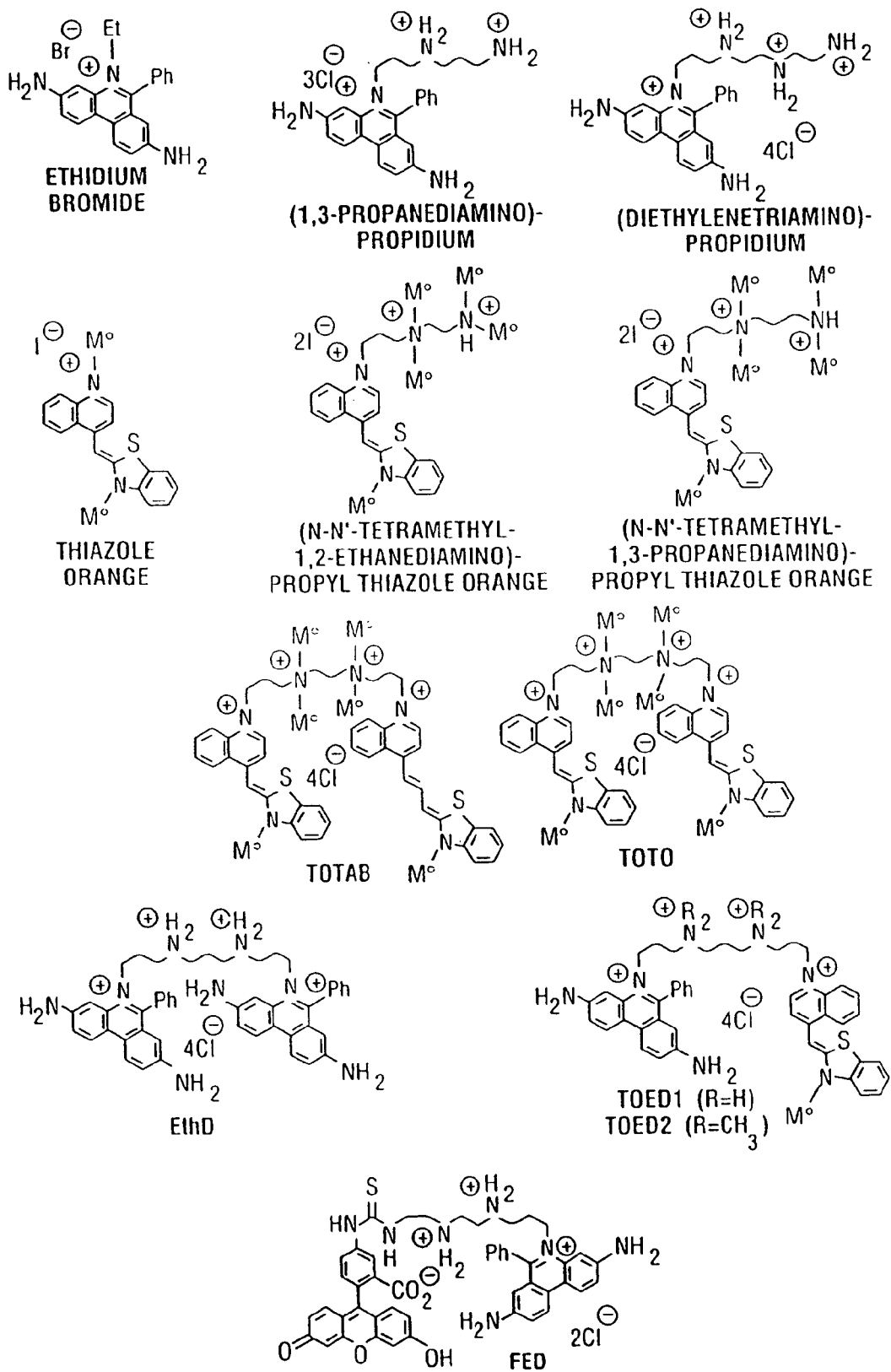
FIG. 1 shows the chemical structure of several positively charged heterodimeric DNA-binding dyes.

As described above, some nucleic acid-based detection assays involve the elongation and/or shortening of oligonucleotide probes. For example, as described herein, the primer-directed, primer-independent, and INVADER-directed cleavage assays, as well as the "nibbling" assay all involve the cleavage (i.e., shortening) of oligonucleotides as a means for detecting the presence of a target nucleic sequence. Examples of other detection assays that involve the shortening of an oligonucleotide probe include the "TaqMan" or nick-translation PCR assay, the assays described in U.S. Pat. Nos. 4,775,619 and 5,118,605 to Urdea, the catalytic hybridization amplification assay described in of Walder and Walder, the cycling probe assay of Duck et al., and the target-catalyzed oligonucleotide modification assay of Western. Examples of detection assays that involve the elongation of an oligonucleotide probe (or primer) include the SNP detection methods of Orchid Bioscience in U.S. Pat. No. 5,952,174, the methods of U.S. Pat. No. 5,882,867 to Ullman et al., the polymerase chain reaction (PCR), and the ligase chain reaction (LCR). The above examples are intended to be illustrative of nucleic acid-based detection assays that involve the elongation and/or shortening of oligonucleotide probes and do not provide an exhaustive list.

Typically, nucleic acid-based detection assays that involve the elongation and/or shortening of oligonucleotide probes require post-reaction analysis to detect the products of the reaction. It is common that the specific reaction product(s) must be separated from the other reaction components, including the input or unreacted oligonucleotide probe. One detection technique involves the electrophoretic separation of reacted and unreacted oligonucleotide probes. When the assay involves the cleavage or shortening of a probe, the unreacted product will be longer than the reacted or cleaved product. When the assay involves the elongation of a probe (or primer), the reaction products will be greater in length than the unreacted probes. Gel-based electrophoresis of a sample containing nucleic acid molecules of different lengths separates these fragments primarily on the basis of size. This is due to the fact that, in solutions having a neutral or alkaline pH, nucleic acids having widely different sizes (i.e., molecular weights) possess very similar charge-to-mass ratios and do not separate based solely on charge (Andrews, Electrophoresis, 2nd Edition, Oxford University Press (1986), pp. 153-154). The gel matrix acts as a molecular sieve and allows nucleic acids to be separated on the basis of size and shape (e.g., linear, relaxed circular or covalently closed supercoiled circles). Unmodified nucleic acids have a net negative charge due to the presence of negatively charged phosphate groups contained within the sugar-phosphate backbone of the nucleic acid. Typically, the sample is applied to gel near the negative pole and the nucleic acid fragments migrate into the gel toward the positive pole with the smallest fragments moving fastest through the gel. For gel electrophoresis to effectively resolve different fragments (i.e., to make them distinguishable from each other), the differences in size or shape must be great enough to cause perceptible differences in the rates of migration of the different fragments through the gel.

The present invention provides novel compositions and methods for characterizing molecules, including nucleic acid molecules, based on differences in charge between starting molecules and molecules that have undergone a modification to add or remove one or more chemical constituents. For example, the present invention provides novel methods and compositions for modifying nucleic acid molecules wherein a cleaved or elongated nucleic acid molecule contains a different charge than unmodified nucleic acids, allowing for the efficient separation and detection of the reacted molecules. While the charge-based separation methods of the present invention are applicable to any number of systems (e.g., separation and characterization of products and intermediates in chemical synthesis and drug design), and are not limited to the use of nucleic acids, the following description focuses on nucleic acid applications to illustrate certain preferred aspects of the present invention.

The detailed description of the invention is presented in the following sections:

I. Fractionation of Specific Nucleic Acids by Selective Charge Reversal
   a. Applications in Invader Assay Cleavage Reactions II. Positively Charged Moieties in the Synthesis of Charge-Balanced Molecules
   a. H-phosphonate Chemistry
   b. A New Class of Phosphoramidite Building Blocks I. Fractionation of Specific Nucleic Acids by Selective Charge Reversal The present invention provides a novel means for fractionating nucleic acid fragments on the basis of charge. This novel separation technique is related to the observation that positively charged adducts can affect the electrophoretic behavior of small oligonucleotides because the charge of the adduct is significant relative to charge of the whole complex. In addition to the use of positively charged adducts (e.g., Cy3 and Cy5 fluorescent dyes, the positively charged heterodimeric DNA-binding dyes shown in FIG. 1, etc.), the oligonucleotide may contain amino acids (particularly useful amino acids are the charged amino acids: lysine, arginine, aspartate, glutamate), polypeptides, modified bases, such as amino-modified bases, charged ions or metals, a phosphonate backbone (at all or a subset of the positions), or any other chemical or molecular constituent that adds to the net positive charge of the oligonucleotide. In other embodiments, as discussed further below, a neutral dye or detection moiety (e.g., biotin, streptavidin, etc.) may be employed in place of a positively charged adduct, in conjunction with the use of amino-modified bases and/or a complete or partial phosphonate backbone.

This observed effect is of particular utility in assays based on the cleavage of DNA molecules. Using the INVADER assays described herein as an example, when an oligonucleotide is shortened through the action of a CLEAVASE enzyme or other cleavage agent, the positive charge can be made to not only significantly reduce the net negative charge, but to actually override it, effectively "flipping" the net charge of the labeled entity. This reversal of charge allows the products of target-specific cleavage to be partitioned from uncleaved probe by extremely simple means. For example, the products of cleavage can be made to migrate towards a negative electrode placed at any point in a reaction vessel, for focused detection without gel-based electrophoresis. When a slab gel is used, sample wells can be positioned in the center of the gel, so that the cleaved and uncleaved probes can be observed to migrate in opposite directions. Alternatively, a traditional vertical gel can be used, but with the electrodes reversed relative to usual DNA gels (i.e., the positive electrode at the top and the negative electrode at the bottom) so that the cleaved molecules enter the gel, while the uncleaved disperse into the upper reservoir of electrophoresis buffer. Similarly, the electrodes of a capillary or microchannel device can be configured so that positively charged cleaved molecules preferentially enter the capillary or channel for separation.

An significant benefit of this type of readout is the absolute nature of the partition of products from substrates (i.e., the separation may be as high as 100%). This means that an abundance of uncleaved probe can be supplied to drive the hybridization step of a probe-based assay, yet the unconsumed (i.e., unreacted) probe can, in essence, be subtracted from the result to reduce background by virtue of the fact that the unreacted probe will not migrate toward the same pole as the specific reaction product.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which generally lack a 3' phosphate, and the products of thermal degradation, which generally retain a 3' phosphate (and thus two additional negative charges, FIG. 2). Examples 1 and 2 demonstrate the ability to separate positively charged reaction products from a net negatively charged substrate oligonucleotide. As discussed in these examples, oligonucleotides may be transformed from net negative to net positively charged compounds. In Example 2, the positively charged dye, Cy3 was incorporated at the 5' end of a 22-mer (SEQ ID NO:1) which also contained two amino-substituted residues at the 5' end of the oligonucleotide; this oligonucleotide probe carries a net negative charge. After cleavage, which occurred 2 nucleotides into the probe, the following labeled oligonucleotide was released: 5'-Cy3-AminoT-AminoT-3' (in addition to unlabeled fragment comprising the remaining 20 nucleotides of SEQ ID NO:1). This short fragment bears a net positive charge while the remainder of the cleaved oligonucleotide and the unreacted or input oligonucleotide bear net negative charges.

Figure 3:
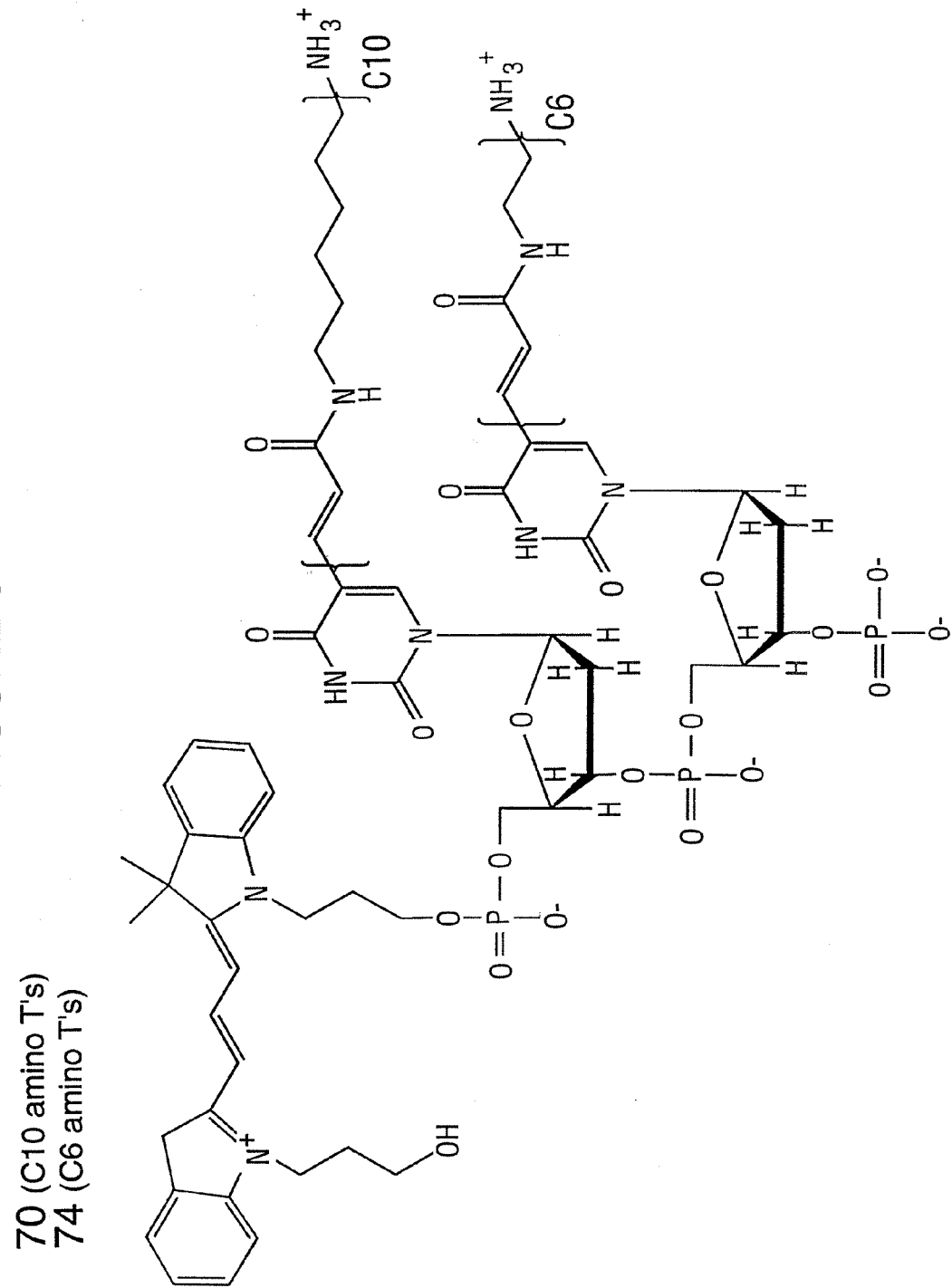
FIG. 3 depicts the structure of amino-modified oligonucleotides 70 and 74.
Figure 4A:
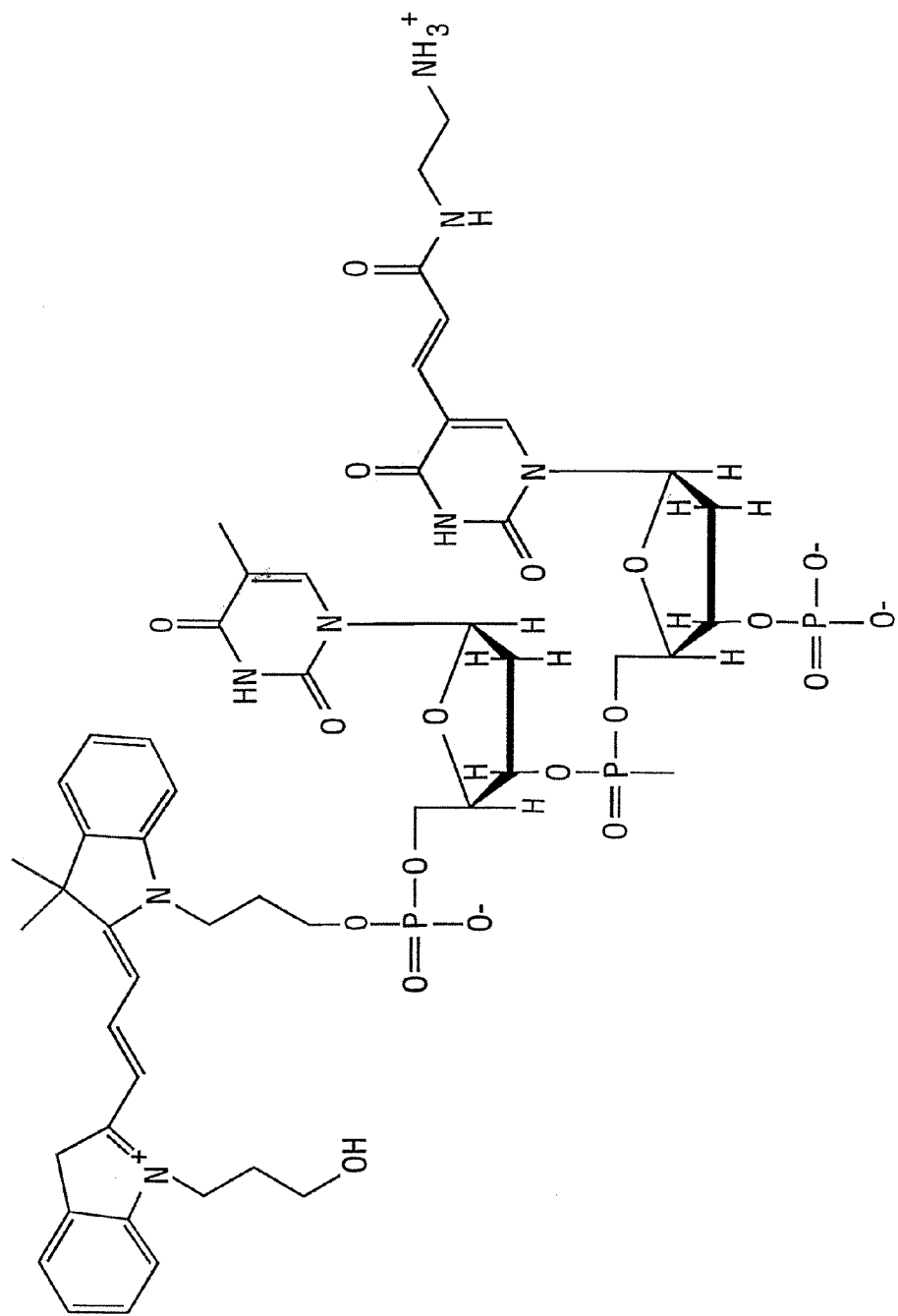
FIG. 4a depicts the structure of amino-modified oligonucleotide 75
Figure 4B:
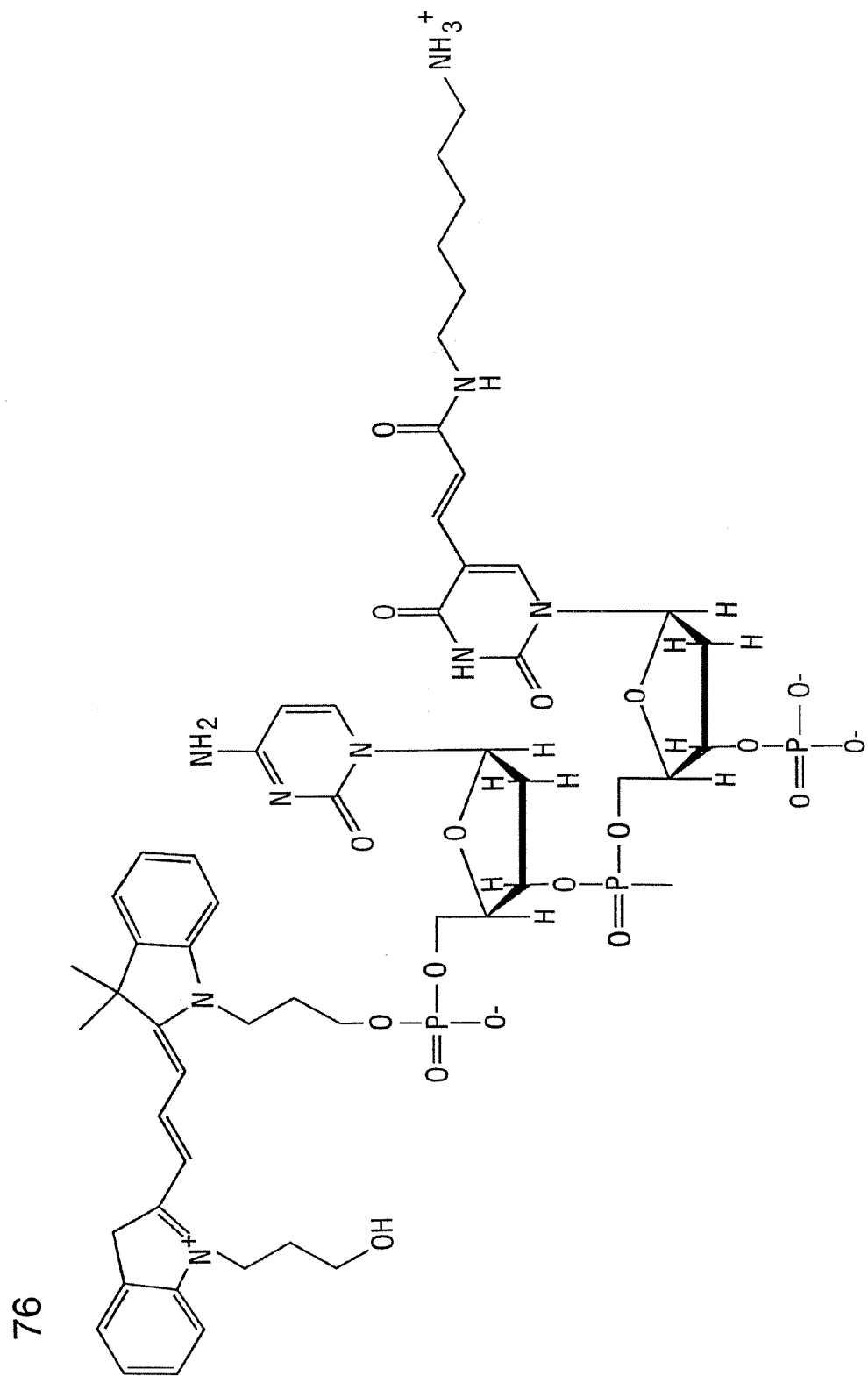
FIG. 4b depicts the structure of amino-modified oligonucleotide 76.

The present invention contemplates embodiments wherein the specific reaction product produced by any cleavage of any oligonucleotide or molecule can be designed to carry a net positive charge while the unreacted molecule is charge neutral or carries a net negative charge. The present invention also contemplates embodiments where the released product may be designed to carry a net negative charge while the input nucleic acid carries a net positive charge. Depending on the length of the released product to be detected, positively charged dyes may be incorporated at the one end of the probe and modified bases may be placed along the oligonucleotide such that upon cleavage, the released fragment containing the positively charged dye carries a net positive charge. Amino-modified bases may be used to balance the charge of the released fragment in cases where the presence of the positively charged adduct (e.g., dye) alone is not sufficient to impart a net positive charge on the released fragment. In addition, the phosphate backbone may be replaced with a phosphonate backbone at a level sufficient to impart a net positive charge (this is particularly useful when the sequence of the oligonucleotide is not amenable to the use of amino-substituted bases); FIGS. 3 and 4 show the structure of short oligonucleotides containing a phosphonate group on the second T residue). An oligonucleotide containing a fully phosphonate-substituted backbone would be charge neutral (absent the presence of modified charged residues bearing a charge or the presence of a charged adduct) due to the absence of the negatively charged phosphate groups. Phosphonate-containing nucleotides (e.g., methylphosphonate-containing nucleotides) are readily available and can be incorporated at any position of an oligonucleotide during synthesis using techniques that are well known in the art.

In essence, in these embodiments the invention contemplates the use of charge-based separation to permit the separation of specific reaction products from the input oligonucleotides in nucleic acid-based detection assays. The foundation of this novel separation technique is the design and use of oligonucleotide probes (typically termed "primers" in the case of PCR) that are "charge balanced" so that upon either cleavage or elongation of the probe it becomes "charge unbalanced," and the specific reaction products may be separated from the input reactants on the basis of the net charge.

In some embodiments, in the context of assays that involve the elongation of an oligonucleotide probe (i.e., a primer), such as is the case in PCR, the input primers are designed to carry a net positive charge. Elongation of the short oligonucleotide primer during polymerization will generate PCR products that now carry a net negative charge. The specific reaction products may then easily be separated and concentrated away from the input primers using the charge-based separation technique described herein.

a. Applications in INVADER Assay Cleavage Reactions i. Detection of Specific Nucleic Acid Sequences Using 5' Nucleases in an INVADER Directed Cleavage Assay The present invention finds application in the detection of cleavage products generated in the INVADER assay. The INVADER assay provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, and 6,090,543 and PCT Publications WO 97/27214 and WO 98/42873, herein incorporated by reference in their entireties.

The INVADER assay further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (Reynaldo et al., J. Mol. Biol. 97:511 [2000])), multiple probes can hybridize in turn to the same target, allowing multiple cleavages, and the generation of multiple cleavage products.

By the extent of its complementarity to a target nucleic acid strand, an oligonucleotide may be said to define a specific region of said target. In an invasive cleavage structure, the two oligonucleotides define and hybridize to regions of the target that are adjacent to one another (i.e., regions without any additional region of the target between them). Either or both oligonucleotides may comprise additional portions that are not complementary to the target strand. In addition to hybridizing adjacently, in order to form an invasive cleavage structure, the 3' end of the upstream oligonucleotide must comprise an additional moiety. When both oligonucleotides are hybridized to a target strand to form a structure and such a 3' moiety is present on the upstream oligonucleotide within the structure, the oligonucleotides may be said to overlap, and the structure may be described as an overlapping, or invasive cleavage structure.

In one embodiment, the 3' moiety of the invasive cleavage structure is a single nucleotide. In this embodiment the 3' moiety may be any nucleotide (i.e., it may be, but it need not be complementary to the target strand). In a preferred embodiment, the 3' moiety is a single nucleotide that is not complementary to the target strand. In another embodiment, the 3' moiety is a nucleotide-like compound (i.e., a moiety having chemical features similar to a nucleotide, such as a nucleotide analog or an organic ring compound; See e.g., U.S. Pat. No. 5,985,557). In yet another embodiment the 3' moiety is one or more nucleotides that duplicate in sequence one or more nucleotides present at the 5' end of the hybridized region of the downstream oligonucleotide. In a further embodiment, the duplicated sequence of nucleotides of the 3' moiety is followed by a single nucleotide that is not further duplicative of the downstream oligonucleotide sequence, and that may be any other nucleotide. In yet another embodiment, the duplicated sequence of nucleotides of the 3' moiety is followed by a nucleotide-like compound, as described above.

The downstream oligonucleotide may have additional moieties attached to either end of the region that hybridizes to the target nucleic acid strand. In a preferred embodiment, the additional moiety comprises a tag of the present invention. In a particularly preferred embodiment, the downstream oligonucleotide comprises a tag or other moiety at its 5' end (i.e., a 5' moiety).

When an overlapping cleavage structure is formed, it can be recognized and cleaved by a nuclease that is specific for this structure (i.e., a nuclease that will cleave one or more of the nucleic acids in the overlapping structure based on recognition of this structure, rather than on recognition of a nucleotide sequence of any of the nucleic acids forming the structure). Such a nuclease may be termed a "structure-specific nuclease." In some embodiments, the structure-specific nuclease is a 5' nuclease. In a preferred embodiment, the structure-specific nuclease is the 5' nuclease of a DNA polymerase. In another preferred embodiment, the DNA polymerase having the 5' nuclease is synthesis-deficient. In another preferred embodiment, the 5' nuclease is a FEN-1 endonuclease. In a particularly preferred embodiment, the 5' nuclease is thermostable.

In some embodiments, the structure-specific nuclease preferentially cleaves the downstream oligonucleotide. In a preferred embodiment, the downstream oligonucleotide is cleaved one nucleotide into the 5' end of the region that is hybridized to the target within the overlapping structure. Cleavage of the overlapping structure at any location by a structure-specific nuclease produces one or more released portions or fragments of nucleic acid, termed "cleavage products."

Detection of the cleavage products may be through release of a label. Such labels may include, but are not limited to one or more of any of dyes, radiolabels such as $^{32}P$ or $^{35}S$, binding moieties such as biotin, mass tags, such as metal ions or chemical groups, charge tags, such as polyamines or charged dyes, haptens such as digoxygenin, luminogenic, phosphorescent or fluorogenic moieties, and fluorescent dyes, either alone or in combination with moieties that can suppress or shift emission spectra, such as by fluorescence resonance energy transfer (FRET) or collisional fluorescence energy transfer.

Examples 1-3 and 9-18, below, demonstrate the use of charge balanced oligonucleotides in the INVADER assay. Cleavage results in the production of charge unbalanced products which are readily separated from the input molecules. The cleavage products are easily detected, providing an efficient and sensitive assay.

II. Positively Charged Moieties in the Synthesis of Charge-Balanced DNA Probes

The present invention provides novel positively charged moieties that may be attached to any number of molecules, including nucleic acid molecules. These positively charged moieties find use in the charge reversal separation methods ("CRE" methods) of the present invention. As used herein, the term "positively charged moiety" refers to a chemical structure that possesses a net positive charge under the reaction conditions of its intended use (e.g., when attached to a molecule of interest under the pH of the desired reaction conditions). Positively charged moieties need not always carry a positive charge. Indeed, in some preferred embodiments of the present invention, the positively charged moiety does not carry a positive charge until it is introduced to the appropriate reaction conditions. This can also be thought of as "pH-dependent" and "pH-independent" positive charges. pH-dependent charges are those that possess the charge only under certain pH conditions, while pH-independent charges are those that possess a charge regardless of the pH conditions.

The positively charged moieties, or "charge tags," when attached to another entity, can be represented by the formula:

where X is the entity (e.g., a solid support, a nucleic acid molecule, etc.) and Y is the charge tag. The charge tags can be attached to other entities through any suitable means (e.g., covalent bonds, ionic interactions, etc.) either directly or through an intermediate (e.g., through a linking group). In preferred embodiments, where X is a nucleic acid molecule, the charge tag is attached to either the 3' or 5' end of the nucleic acid molecule.

The charge tags may contain a variety of components. For example, the charge tag Y can be represented by the formula:

$$Y_1—Y_2$$

where $Y_1$ comprises a chemical component that provides the positive charge to the charge tag and where $Y_2$ is another desired component. $Y_2$ may be, for example, a dye, another chemical component that provides a positive charge to the charge tag, a functional group for attachment of other molecules to the charge tag, a nucleotide, etc. Where such a structure is attached to another entity, X, either $Y_1$ or $Y_2$ may be attached to X.

$$X—Y_1—Y_2 \text{ or } X—Y_2—Y_1.$$

The charge tags are not limited to two components. Charge tags may comprise any number of desired components. For example, the charge tag can be represented by the formula:

$$Y_1—Y_2—Y_3—Y_n (n=\text{any positive integer}).$$

where any of the Y groups comprises a chemical component that provides the positive charge to the charge tag and where the other Y groups are any other desired components. For example, in some embodiments, the present invention provides compositions of the structure:

$$X—Y_1—Y_2—Y_3—Y_4$$

where X is an entity attached to the charge tag (e.g., a solid support, a nucleic acid molecule, etc.) and where $Y_1$ is a dye, $Y_2$ is a chemical component that provides the positive charge to the charge, $Y_3$ is a component containing a functional group that allows the attachment of other molecules, and $Y_4$ is a second chemical component that provides a positive charge. The identity of each of $Y_1$-$Y_4$ can be interchanged (i.e., the present invention is not limited by the order of the components).

The present invention is not limited by the nature of the chemical components that provides the positive charge to the charge tag. Such chemical components include, but are not limited to, amines (primary, secondary, and tertiary amines), ammoniums, and phosphoniums. The chemical components may also comprise chemical complexes that entrap or are otherwise associated with one or more positively charged metal ions.

In preferred embodiments of the present invention, charge tags are attached to nucleic acid molecules (e.g., DNA molecules). The charge tags may be synthesized directly onto a nucleic molecule or may be synthesized, for example, on a solid support or in liquid phase and then attached to a nucleic acid molecule or any other desired molecule. In some preferred embodiments of the present invention, charge tags that are attached to nucleic acid molecules comprise one or more components synthesized by H-phosphonate chemistry (described in detail below), by incorporation of novel phosphoramidites (described in detail below), or a combination of both. For example, compositions of the present invention include structures such as:

$$[X]—[Y_1—Y_2—Y_3—Y_4]$$

where [X] is a nucleic acid molecule and [Y . . . ] is a charge tag. In some embodiments, $Y_1$ is a dye, $Y_2$ is synthesized using H-phosphonate chemistry and comprises a chemical component that provides a positive charge to the charge tag, $Y_3$ is a positively charged phosphoramidite, and $Y_4$ is a nucleotide or polynucleotide. Any of the Y components are interchangeable with one another.

Such compositions find use in the charge-separation assays of the present invention. For example, a probe molecule in the INVADER assay may have a charge tag attached to its 5' end. The probe may comprise a net negative charge because of the plurality of negatively charge phosphate groups in the oligonucleotide backbone. Cleavage of the probe releases the charge tag from the rest of the probe. The released cleavage fragment, containing the charge tag, carries a net positive charge, while the remaining probe oligonucleotide carries a net negative charge. The cleaved fragments can then be readily separated from the uncleaved probes and detected, indicating the presence of a specific target sequence in the experimental sample.

a. H-Phosphonate Chemistry.

As discussed above, one or more components of a charge tag can be synthesized using H-phosphonate chemistry. Production of charge tags using the methods described herein provides a convenient and flexible modular approach for the design of a wide variety of charge tags. Since its introduction, solid phase H-phosphonate chemistry (B. C. Froehler, Methods in Molecular Biology, 20:33, S. Agrawal, Ed. Humana Press; Totowa, N.J. [1993]) has been recognized as an efficient tool in the chemical synthesis of natural, modified and labeled oligonucleotides and DNA probes. Those skilled in the art know that this approach allows for the synthesis of the oligonucleotide fragments with a fully modified phosphodiester backbone (e.g., oligonucleotide phosphorothioates; Froechler [1993], supra) or the synthesis of oligonucleotide fragments in which only specific positions of the phosphodiester backbone are modified (Agrawal, et al., Proc. Natl. Acad. Sci USA, 85:7079 [1988], Froehler, Tetrahedron Lett. 27:5575[1986], Froehler, et al., Nucl. Acids Res. 16:4831 [1988]). The use of H-phosphonate chemistry allows for the introduction of different types of modifications into the oligonucleotide molecule (Agrawal, et al., Froehler[1986], supra, Letsinger, et al., J. Am. Chem. Soc., 110:4470 [1988], Agrawal and Zamecnik, Nucl. Acid Res. 18:5419 [1990], Handong, et al., Bioconjugate Chem. 8:49 [1997], Vinogradov, et al., Bioconjugate Chem. 7:3 [1995], Schultz, et al., Tetrahedron Lett. 36:8407 [1995]), however the replacement of the phosphodiester linkage by the phosphoramidate linkage is one of the most frequent changes due to its effectiveness and synthetic flexibility. Froehler and Letsinger were among first to use this approach in the synthesis of modified oligonucleotides in which phosphodiester linkages were fully or partially replaced by the phosphoramidate linkages bearing positively charged groups (e.g., tertiary amino groups; Froehler [1986], Froehler, et al., [1988], and Letsinger, et al., supra).

In some embodiments of the present invention, charge tags are generated using H-phosphonate chemistry. The charge tags may be assembled on the end of a nucleic acid molecule or may be synthesized separately and attached to a nucleic acid molecule. Any suitable phosphorylating agent may be used in the synthesis of the charge tag. For example, the component to be added may contain the structure:

$$A\text{-}B—P$$

where A is a protecting group, B is any desired functional group (e.g., a functional group that provides a positive charge to the charge tag), and P is a chemical group containing phosphorous. In preferred embodiments, B comprises a chemical group that is capable of providing a positive charge to the charge tag. However, in some embodiments B is a functional group that allows post-synthetic attachment of a positively charged group to the charge tag.

The process of the synthesis of the charge-balanced charge tag containing (CRE) probes using H-phosphonate chemistry can be divided into steps.

1. In the first step, the specific DNA sequence is synthesized using a standard automated phosphoramidite protocol (a reporter molecule (dye) may be introduced into the molecule at this stage using phosphoramidite or H-phosphonate chemistry, or it can be attached to the probe after the completion of other steps of the modification procedure using any of the standard post-synthetic labeling protocols).

2. In the second step, a modification procedure is performed using solid-phase H-phosphonate chemistry. The DNA probe, suspended on the solid support, is coupled to an appropriate H-phosphonate monomer in the presence of an appropriate activating reagent (e.g., pivaloyl chloride). This step leads to the formation of the reactive H-phosphonate intermediate (FIG. 5).

Figure 5:
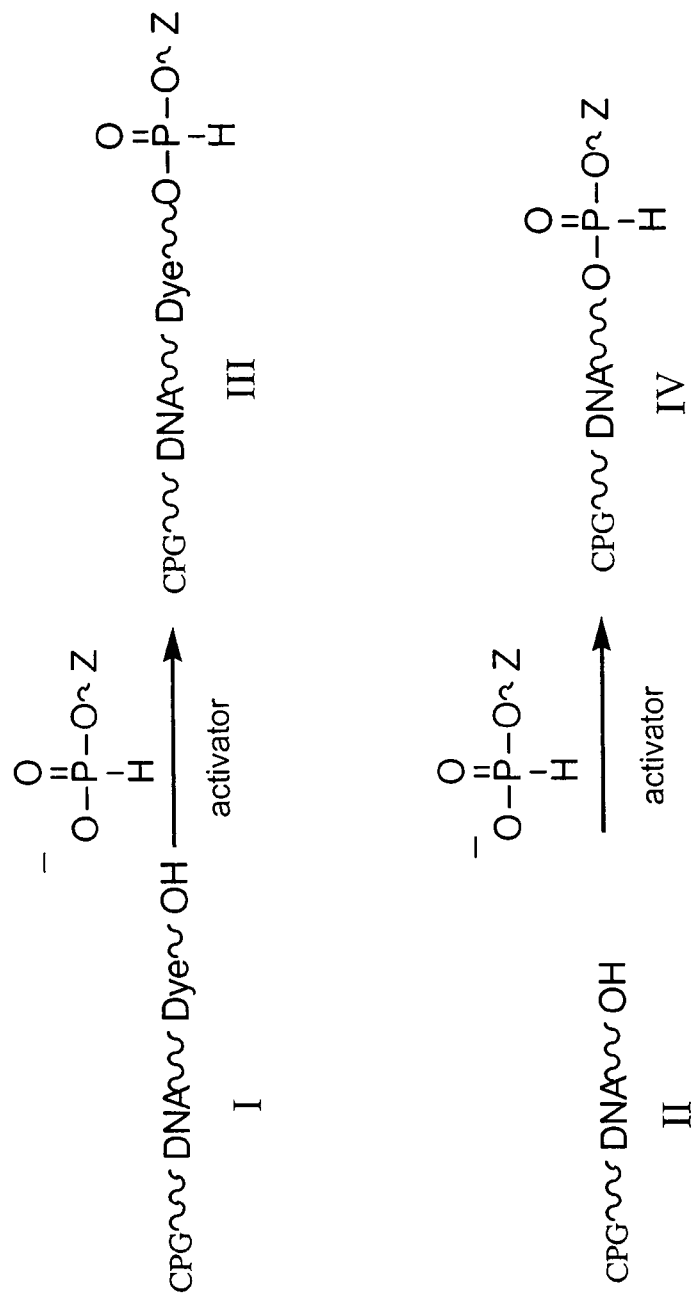
FIG. 5 diagrams the steps leading to the formation of a reactive H-phosphonate intermediate. The wavy lines shown linking the various constituents of these compositions in this and other drawings represent any organic group that can serve this linking purpose.

Group "Z" in FIG. 5 represents any organic group (with any other functional groups present protected as necessary for protocols of chemical synthesis of oligonucleotides). Group "Z" may optionally contain other DMT-protected hydroxyl groups (or other appropriately protected functional groups), to which additional monomeric units (e.g., H-phosphonate, phosphoramidite, etc.) can be attached, either covalently or noncovalently (e.g. thorough complex formation). Wavy lines in FIG. 5 and other figures in this patent disclosure, e.g., as shown linking controlled pore glass (CPG) and the DNA molecule (and which may link any two entities of these compositions), represent any kind of atom or organic group that can serve these purposes.

This step should be performed on a DNA synthesizer with H-phosphonate adaptation or should be performed manually according to a solid phase H-phosphonate coupling protocol.

Figure 6:
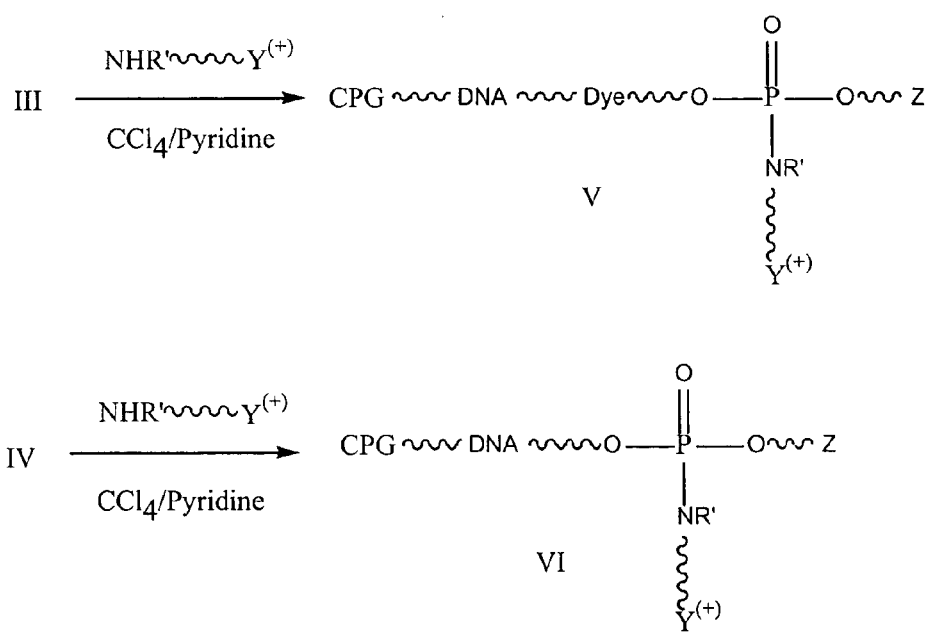
FIG. 6 diagrams the conversion step leading to the synthesis of V and VI compounds.
Figure 7:
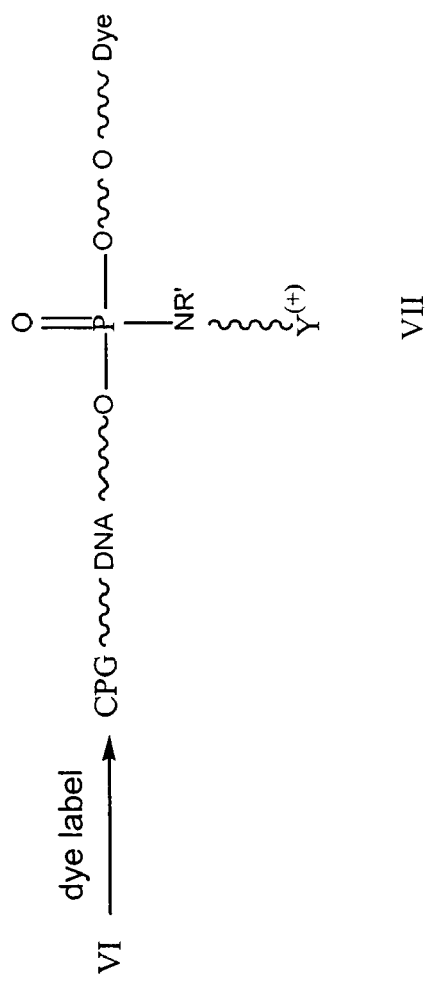
FIG. 7 illustrates the creation of an additional compound VII by altering the order of addition of the constituents (compared, e.g., with the order leading to the creation of compound VI, FIG. 6).

A subsequent step of the modification procedure involves the conversion of the intermediate H-phosphonate into the phosphoramidate-bearing group(s) that can introduce positive charges into the composition. Usually, this conversion is performed with the help of an Atherton-Tod reaction, in which the intermediate H-phosphonate III or IV is treated with a solution of an appropriate primary or secondary amine, carbon tetrachloride (or other reagent(s) leading to the same type of transformation in which phosphoramidate bond between the amine used in the reaction and phosphorus atom is formed) in anhydrous aprotic solvent(s), preferably pyridine, mixture of pyridine and acetonitrile, or pyridine and tetrahydrofuran. FIG. 6 shows the conversion leading to the synthesis of V and VI.

The structure of the monomeric H-phosphonate may optionally contain additional, appropriately protected functional groups (e.g., amino, hydroxyl, mercapto or carboxy groups) that can be used in other steps of the synthesis and modification of the probe containing the charge tag.

If the modification procedure involves multiple coupling steps performed using H-phosphonate chemistry or phosphoramidite chemistry, the H-phosphonate monomer(s) used in the modification procedure should contain selectively protected hydroxyl group, preferably with the DMT protecting group, while other functional groups should be protected with protecting groups compatible with the protocol of the chemical synthesis of oligonucleotides.

It is important to note that the possibility of the use of the intermediate materials I or II significantly increases the synthetic flexibility of the modification procedure (and helps to create a broad variety of charge-balanced probes). By altering the sequence of coupling of the H-phosphonate reagents and another reagents (e.g. reporter molecules) to the synthesized DNA sequence, different probes (CRE-VI) can be synthesized. The probes generate fragments of varying polarity and/or mobility upon cleavage in, for example, an INVADER assay. The synthetic flexibility of the H-phosphonate approach can be conveniently illustrated on the example of the synthesis of the multiple labeled CRE probe.

Introduction of multiple points of modification with moieties bearing positive charge(s) may be desired, in order to compensate negative charges introduced into the probe by another group (e.g., a dye bearing multiple negative charges or other groups).

Figure 8:
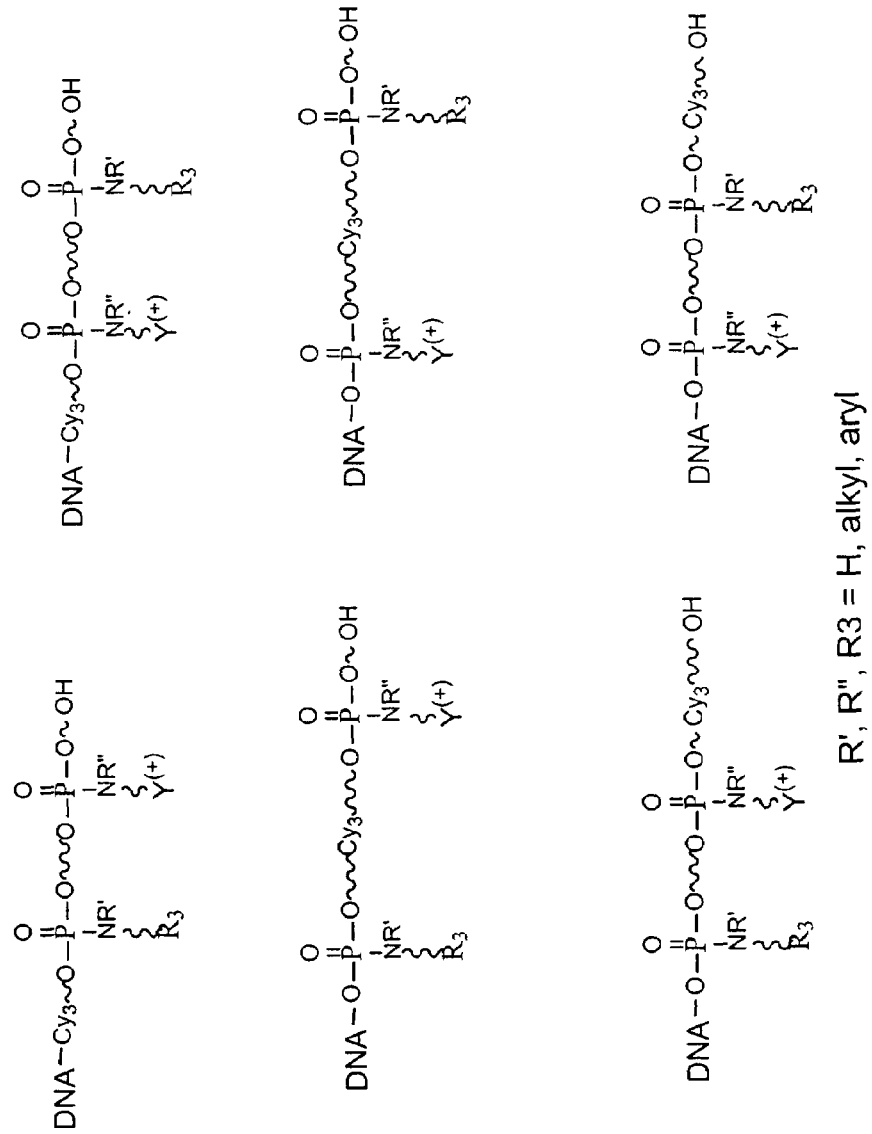
FIG. 8 illustrates several possible modification configurations for a probe containing two points of modification.

The synthesis of CRE probes containing only two points of modification, one introducing a positively charged moiety and one introducing a neutral group for structure modulation, and having only one dye that does not alter the net charge (e.g., Cy3 dye introduced using phosphoramidite chemistry), is illustrated in FIG. 8.

As it can be seen, the synthetic procedure in which only one reporter group, one type of H-phosphonate monomer and two different amines were used, can generate six different charge-balanced CRE probes. The number of possible structural variations of the synthesized charge-balanced CRE probes using a single reporter molecule (e.g., Cy3) can be significantly expanded if the synthesis is performed using one of two structurally different H-phosphonate monomers, one of two different amines for introducing positive charge, and one of two different amines for structure modulation. The use of those reagents will lead to the creation of four different modifications introducing positive charge and four different structure modulating modifications.

In the discussed example, the structure of a charge-balanced CRE probe should contain one position occupied by a reporter molecule (e.g. Cy3), one position occupied by a modification introducing positive charge and (optionally) one position occupied by a structure-modulating modification. A total 96 different charge-balanced CRE probes can be synthesized using the above mentioned reagents.

Figure 9:
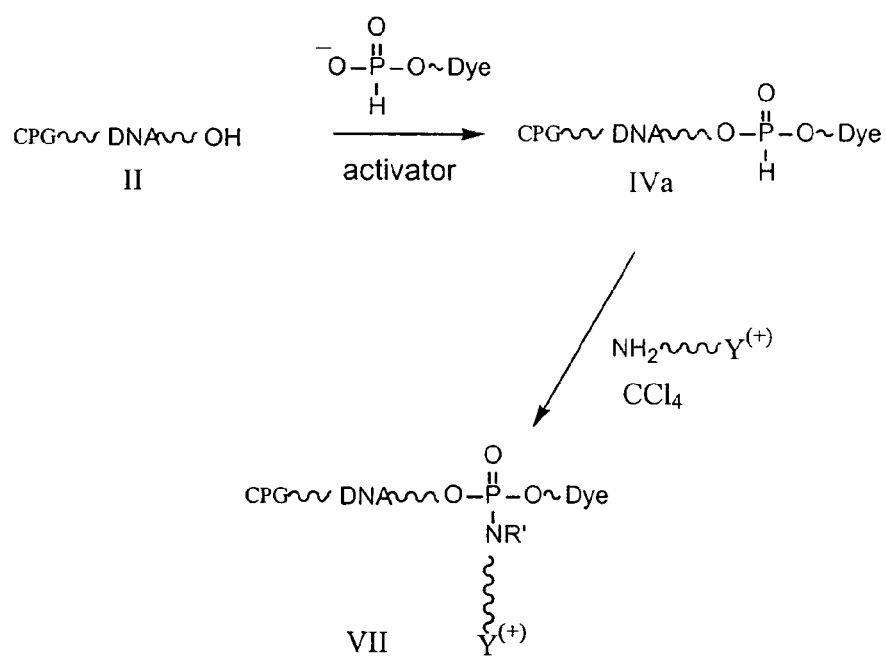
FIG. 9 diagrams the process of introducing a reporter group (e.g., a dye) into a synthesized compound using H-phosphonate chemistry.

It is clear that a large number of possible structural permutations are achieved with the use of only seven different reagents, allowing for the selection of the structural arrangement that will offer a particular desired probe performance (i.e., assay performance and/or the desired electrophoretic mobility of the cleaved positively charged fragments). The same set of reagents can be used in the synthesis of charge balanced probes that do not contain any neutral modifications (e.g., as used for structure modulation) or that contain multiple points at which structure-modulating modification can be added. This further expands the number of possible structures of charge-balanced probes that can be synthesized using a relatively small (seven in the discussed example) number of reagents. It is important to note that reporter groups can be also introduced into CRE probes using H-phosphonate chemistry. FIG. 9 diagrams a process in which an activated H-phosphonate of a reporter molecule (e.g., a dye) reacts with an available hydroxyl group of an oligonucleotide attached to a solid phase, leading to the formation of an intermediate H-phosphonate IVa, which is subsequently converted to a phosphoramidate-derivative using an appropriate primary or secondary amine and the chemical reaction described above.

Figure 10:
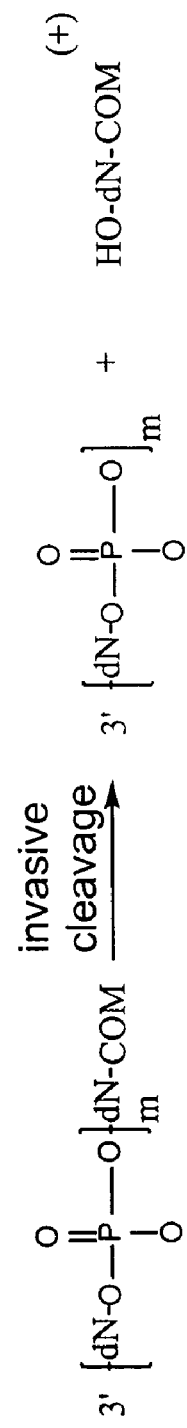
FIG. 10 diagrams the release of a positively-charged tag from an oligonucleotide by cleavage in an INVADER assay.

In all cases, these procedures lead to the attachment of a specific structure of charged organic moiety (described later as COM$^{(+)}$) to a DNA sequence. As a result, a positively charged fragment (positively charged Tag; called later "PCT") cleaved in the enzymatic process, will be composed of one nucleotide and the COM$^{(+)}$, and will have the desired net positive charge (FIG. 10).

Figure 11:
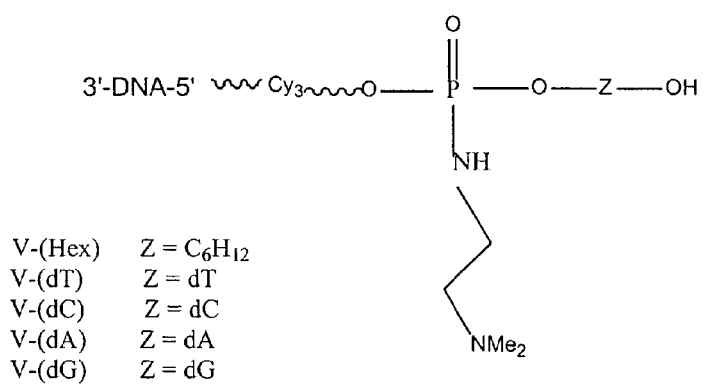
FIG. 11 diagrams five different charge tags, shown as they would be attached to an oligonucleotide.

As an example illustrating the use of H-phosphonate chemistry in the synthesis of the CRE probes, the synthesis of five different charge-balanced CRE probes was performed (FIG. 11). All synthesized charge-balance probes were tested in an INVADER assay. It was found that the cleaved PCTs have different electrophoretic mobility under the conditions of reverse capillary electrophoresis.

Figure 12:
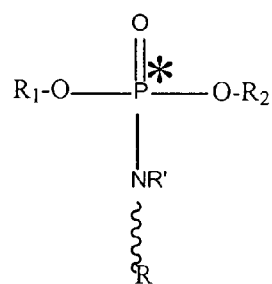
FIG. 12 diagrams a chiral phosphoramidite.

The use of H-phosphonates in the modification of CRE probes is associated with the generation of a new center of chirality at the tetracoordinated phosphoramidate phosphorus atom (FIG. 12). The use of chiral (optically active) and more sterically bulky H-phosphonate monomers (e.g. dT, dA, dC, dG H-phosphonates) can lead to the formation of diastereoisomers, which will have different chromatographic and electrophoretic properties. When relatively small and achiral H-phosphonate monomer was used (e.g., DMT-protected H-phosphonate of 1,6-hexanediol), the formation of the stereoisomers was not detectable under either reverse phase HPLC and capillary electrophoresis conditions. However, diastereoisomeric forms of the larger synthesized materials can be detected as separate peaks in the analytical RP HPLC profiles, and in the CE profiles of both the intact CRE probes and the positively charged products of enzymatic cleavage. The separations between diastereoisomers under those conditions can vary and can depend on the nature of the groups introduced in the modification step. Introduction of multiple points (n) of modification using H-phosphonate reagents leads to the formation of $2^n$ diastereoisomers, which may or may not be separated under the conditions used for the probe purification, analysis or under the conditions of the CRE experiments. The separation of the diastereoisomers can be disadvantageous in situations where probes will be used in a multiplex assay. Formation of the diastereoisomeric forms of the charge balanced CRE probes was observed in all cases in which H-phosphonates of the 5'-DMT protected deoxynucleosides were used.

In one case, (dA H-phosphonate, amine used in the conversion of the intermediate H-phosphonate into the phosphoramidate: $H_2NCH_2CH_2NMe_2$) the separation of the diastereoisomers under reverse phase HPLC conditions (C-18 column) allowed separation of the isomers. Analysis of the isolated fractions by mass spectrometry revealed that the materials had identical molecular weight, corresponding to that of the desired product. Therefore, if a step of purifying the individual diastereoisomers is not intended, or when complete separation is not possible, the use of achiral H-phosphonates as a building block in the synthesis of the CRE probes for such system may be preferred to the use of chiral H-phosphonates. However, in cases when the separation of the diastereoisomers in pure form is possible (e.g., by reverse phase HPLC), the individual diastereoisomers can be used as separable tags in CRE assays, further expanding the diverse library of the H-phosphonate-generated CRE probes.

In some embodiments of the present invention, an H-phosphonate of Cy3 is used to directly introduce a charge-bearing unit into a charge tag. For example, use of an H-phosphonate of Cy3 can provide a charge tag containing the structure:

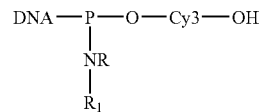

where any desired amine can be readily incorporated into the position NR. This allows, for example, the production of a palette of different charge tags that will provide different mobility in separation assays.

b. A New Class of Phosphoramidite Building Blocks: "Positively Charged Phosphoramidites" (PCP) and "Neutral Phosphoramidites" (NP).

Positively charged phosphoramidites (PCP) and neutral phosphoramidites (NP) represent a new class of phosphoramidite building blocks designed to introduce both positive charge and structure modulation into the synthesized charge-balanced CRE probe.

Figure 13:
FIG. 13 diagrams the conversion of a phosphoramidite group to a phosphodiester linkage, as during oligonucleotide synthesis.
Figure 14:
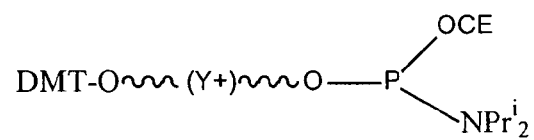
FIG. 14 diagrams the general structures of neutral (A) and positively charged (B) phosphoramidites.
Figure 14:
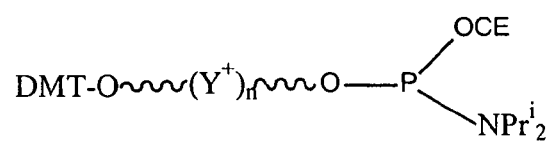

A standard coupling protocol using phosphoramidite reagents is associated with the introduction into the growing molecule, of one negative charge per coupling step, due to the formation of the phosphodiester linkage (FIG. 13). In the synthesis of charge-balanced CRE probes in which a specific ratio of negative and positive charges should be maintained, the introduction of additional negative charges can represent a disadvantage. To eliminate this disadvantage, new types of phosphoramidites were designed to either introduce a net positive charge(s) at each coupling step (positively charged phosphoramidites, PCPs), or to introduce no extra charge (neutral phosphoramidites, NPs) into the synthesized CRE probe. FIG. 14 shows general structures of the PCP and NP phosphoramidites in some embodiments of the present invention.

The positively charged group ($Y^+$) represents any organic group that can exist in a positively charged form, preferably primary, secondary or tertiary amines. Modification with the introduction of quaternary ammonium groups or other organic positively charged groups is also contemplated.

Both PCPs and NPs can be used in combination with other phosphoramidite building blocks (PBBs), which introduce one negative charge per coupling, but which can serve as structure modulating factors. Diversification of the structures of the PCPs and NPs can also serve as factors for the structure modulation of the synthesized CRE probe. This approach allows for the synthesis of a large variety of the charge-balanced CRE probes using a standard phosphoramidite coupling protocol for oligonucleotide synthesis.

For example, FIG. 15 illustrates possible combinations in the synthesis of the charge-balanced CRE probe when the synthesis is performed with the use of one dye phosphoramidite (DP), which introduces zero net charge (e.g., Cy3 phosphoramidite), PBB, which introduces one negative charge, one NP introducing zero net charge, and one PCP, which introduces one net positive charge. As shown in FIG. 15, due to the large number of positional permutations possible in the design of the probe structure, a large variety of charge-balanced structures can be synthesized using only four reagents.

While FIG. 15 illustrates the synthesis of the charge-balanced CRE probes in which the reporter molecule (Cy3) is attached directly to the oligonucleotide sequence, other structural permutations in which the reporter molecule can occupy other positions are also contemplated.

Therefore, this approach creates a unique opportunity to synthesize a large number of the charge-balanced CRE probes using only one reporter molecule. For example, FIG. 13 presents an embodiment in which a dye that does not introduce any net charge (e.g., Cy3 phosphoramidite) was used in probe synthesis. This does not preclude the use other dyes in the synthesis of a different set of charge-balanced CRE probes for use, e.g., in multiplex detection systems using, for example, the INVADER Assay. It is also worth noting that, in contrast to the H-phosphonate approach, the use of the new type of phosphoramidites does not lead to the creation of new centers of chirality.

Figure 16:
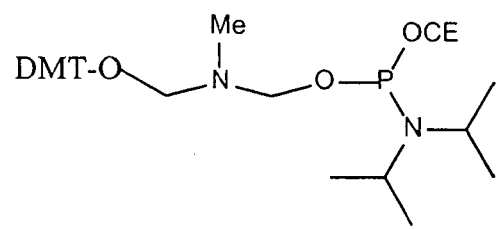
FIG. 16 diagrams examples of synthesized neutral and positively charged phosphoramidites.
Figure 16:
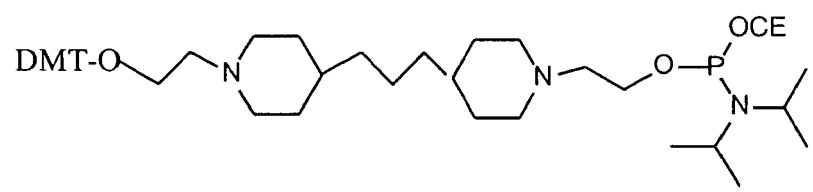
Figure 17:
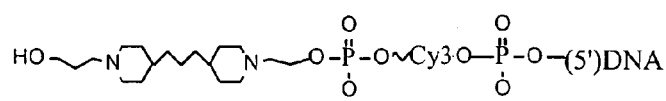
FIG. 17 shows the structures of a group of charge balances oligonucleotide probes made using neutral and positively charged phosphoramidites.
Figure 17:
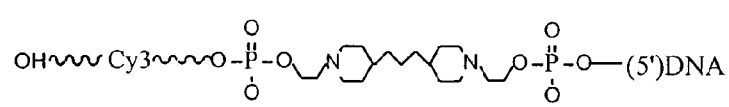
Figure 17:
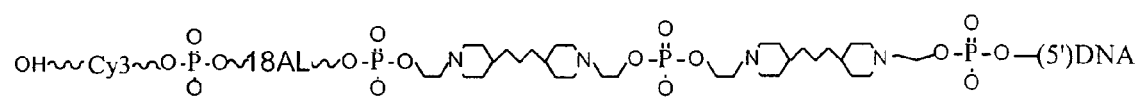
Figure 17:
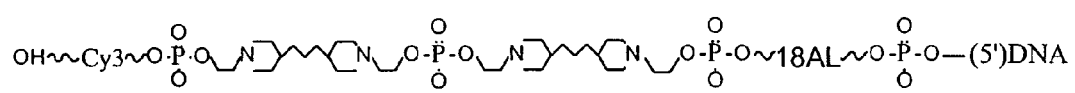
Figure 17:
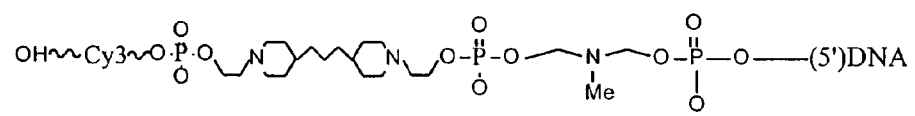
Figure 17:
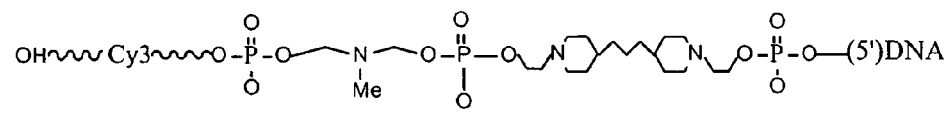

In an additional embodiment, the H-phosphonates and the phosphoramidites of the present invention are used in combination, e.g., in the synthesis of the specifically modified charge-balanced CRE probes. FIG. 16 shows an example of the synthesized neutral phosphoramidite and positively charged phosphoramidite, and FIG. 17 shows the structures of a set of charge-balanced CRE probes that were synthesized utilizing PCPs and NPs.

Commercially available phosphoramidite of the 18-atom linker (polyethylene glycol derivative; Glen Research; Cat.# 10-1918-90) was used as a building block phosphoramidite used for structure modulation, (indicated in FIG. 17 as "18AL").

Linkers of different lengths and of different chemical natures can be used as structure modulating reagents.

The present invention also provides new synthetic methods using phosphoramides to generate charge tags containing a unit with a charge group and a phosphate group. For example, as described above, H-phosphonate chemistry can be used to add a charged unit onto a nucleic acid structure:

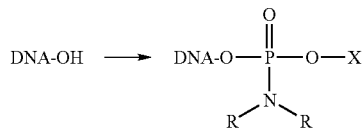

(where X is one or more additional components of the charge tag and the R groups are any other desired chemical groups). The same structure may be generated using phosphoramidite addition by first adding the phosphoramide, then using a Michaelis-Arbuzov reaction in the presence of, for example, an amine:

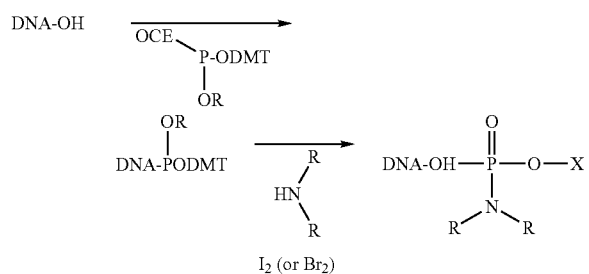

The above methods of generating charge tags allow an extremely wide variety of charge tags to be made. This variety of options allows for multiplex detection methods. For example, in the context of the INVADER assay, a charge tag attached to a probe oligonucleotide could have three components:

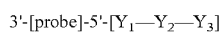

where $Y_1$ is one of any number of dyes, $Y_2$ is one of any number of groups containing a positive charges, and $Y_3$ is one of four nucleotides (e.g., not complementary to the target nucleic acid). If four different dyes and four different charged groups are used, this would introduce 4×4×4, or 64 distinct charge tags that could be individually resolvable using the methods described herein (e.g., microfluidics). By adding additional components or additional choices at each component, hundred to thousands or more distinct charge tags can be made and used in multiplex analyses.

EXAMPLES

The following examples serve to illustrate certain preferred embodiments and aspects of the present invention and are not to be construed as limiting the scope thereof.

In the disclosure which follows, the following abbreviations apply: Afu (*Archaeoglobus fulgidus*); Mth (*Methanobacterium thermoautotrophicum*); Mja (*Methanococcus jannaschii*); Pfu (*Pyrococcus furiosus*); Pwo (*Pyrococcus woesei*); Taq (*Thermus aquaticus*); Taq DNAP, DNAPTaq, and Taq Pol I (*T. aquaticus* DNA polymerase I); DNAPStf (the Stoffel fragment of DNAPTaq); DNAPEc1 (*E. coli* DNA polymerase I); Tth (*Thermus thermophilus*); Ex. (Example); FIG. (Figure); ° C. (degrees Centigrade); g (gravitational field); hr (hour); min (minute); olio (oligonucleotide); rxn (reaction); vol (volume); w/v (weight to volume); v/v (volume to volume); BSA (bovine serum albumin); CTAB (cetyl-trimethylammonium bromide); HPLC (high pressure liquid chromatography); DNA (deoxyribonucleic acid); p (plasmid); μl (microliters); ml (milliliters); μg (micrograms); mg (milligrams); M (molar); mM (milliMolar); μM (microMolar); pmoles (picomoles); amoles (attomoles); zmoles (zeptomoles); nm (nanometers); kdal (kilodaltons); OD (optical density); EDTA (ethylene diamine tetra-acetic acid); FITC (fluorescein isothiocyanate); SDS (sodium dodecyl sulfate); NaPO$_4$ (sodium phosphate); NP-40 (Nonidet P-40); Tris (tris (hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PBS (phosphate buffered saline containing 1 mM PMSF); PAGE (polyacrylamide gel electrophoresis); Tween (polyoxyethylene-sorbitan); ATCC (American Type Culture Collection, Rockville, Md.); Coriell (Coriell Cell Repositories, Camden, N.J.); DSMZ (Deutsche Sammlung von Mikroorganismen und Zellculturen, Braunschweig, Germany); Sigma (Sigma Chemical Company, St. Louis, Mo.); MJ Research (MJ Research, Watertown, Mass.); Novagen (Novagen, Inc., Madison, Wis.); Perkin Elmer (Perkin Elmer Instruments, Norwalk, Conn.); Promega (Promega Corp. Madison, Wis.); Clonetech (Clonetech, Palo Alto, Calif.); Pharmacia (Pharmacia, Piscataway, N.J.); Hitachi (Hitachi Instruments Inc. San Jose, Calif.), Qiagen (Qiagen, Inc. Valencia, Calif.); Bio101 (Bio 101 Inc. Vista, Calif.); Aldrich (Aldrich Chemical Company Inc. Milwaukee, Wis.); VWR (VWR Scientific Products, West Chester, Pa.); Glen Research (Glen Research Corporation, Sterling Va.); PE Biosystems (PE/Applied Biosystems, Foster City, Calif.); Wheaton (Wheaton Science Products, Millville, N.J.); EM Science (EM Science, Gibbstown N.J.); Gelman (Gelman Science, Ann Arbor, Mich.); Becton Dickensen (Becton Dickensen Labware, Bedford, Mass.); Büchi (Büchi Analytical, Switzerland); Chemglass (Chemglass Inc. Vineland, N.J.); Dot Scientific (Dot Scientific Inc. Burton, Mich.); Eppendorf Scientific (Eppendorf Scientific Inc. Westbury, N.Y.); Applied Biosystems (Applied Biosystems, Foster City, Calif.); Invitrogen (Invitrogen Corporation, Carlsbad, Calif.); Ambion (Ambion Inc. Austin, Tex.); Gibco BRL (Life Technologies, Gaithersburg, Md.); USB (US Biochemical, Cleveland, Ohio); Calbiochem (Calbiochem, San Diego, Calif.).

Example 1

Detection of DNA by Charge Reversal

The detection of specific targets is achieved in the INVADER-directed cleavage assay by the cleavage of a probe oligonucleotide. The cleaved probe may be separated from the uncleaved probe using the charge reversal technique described below. This novel separation technique is related to the observation that positively charged adducts can affect the electrophoretic behavior of small oligonucleotides because the charge of the adduct is significant relative to charge of the whole complex. Observations of aberrant mobility due to charged adducts have been reported in the literature, but in all cases found, the applications pursued by other scientists have involved making oligonucleotides larger by enzymatic extension. As the negatively charged nucleotides are added on, the positive influence of the adduct is reduced to insignificance. As a result, the effects of positively charged adducts have been dismissed and have received little notice in the existing literature.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which generally lack a 3' phosphate, and the products of thermal degradation, which generally retain a 3' phosphate (and thus two additional negative charges).

a) Characterization of the Products of Thermal Breakage of DNA Oligonucleotides

Thermal degradation of DNA probes results in high background that can obscure signals generated by specific enzymatic cleavage, decreasing the signal-to-noise ratio. To better understand the nature of DNA thermal degradation products, the 5' tetrachloro-fluorescein (TET)-labeled oligonucleotides 78 (SEQ ID NO:3) and 79 (SEQ ID NO:4) (100 pmole each) were incubated in 50 µl 10 mM $NaCO_3$ (pH 10.6), 50 mM NaCl at 90° C. for 4 hours. To prevent evaporation of the samples, the reaction mixture was overlaid with 50 µl of CHILLOUT liquid wax (MJ Research). The reactions were then divided in two equal aliquots (A and B). Aliquot A was mixed with 25 µl of methyl violet loading buffer and Aliquot B was dephosphorylated by addition of 2.5 µl of 100 mM $MgCl_2$ and 1 µl of 1 unit/µl Calf Intestinal Alkaline Phosphatase (CIAP)(Promega), with incubation at 37° C. for 30 min. after which 25 µl of methyl violet loading buffer was added. One microliter of each sample was resolved by electrophoresis through a 12% polyacrylamide denaturing gel and imaged as described in Example 21; a 585 nm filter was used with the FMBIO Image Analyzer. The resulting imager scan is shown in FIG. 2.

Figure 2:
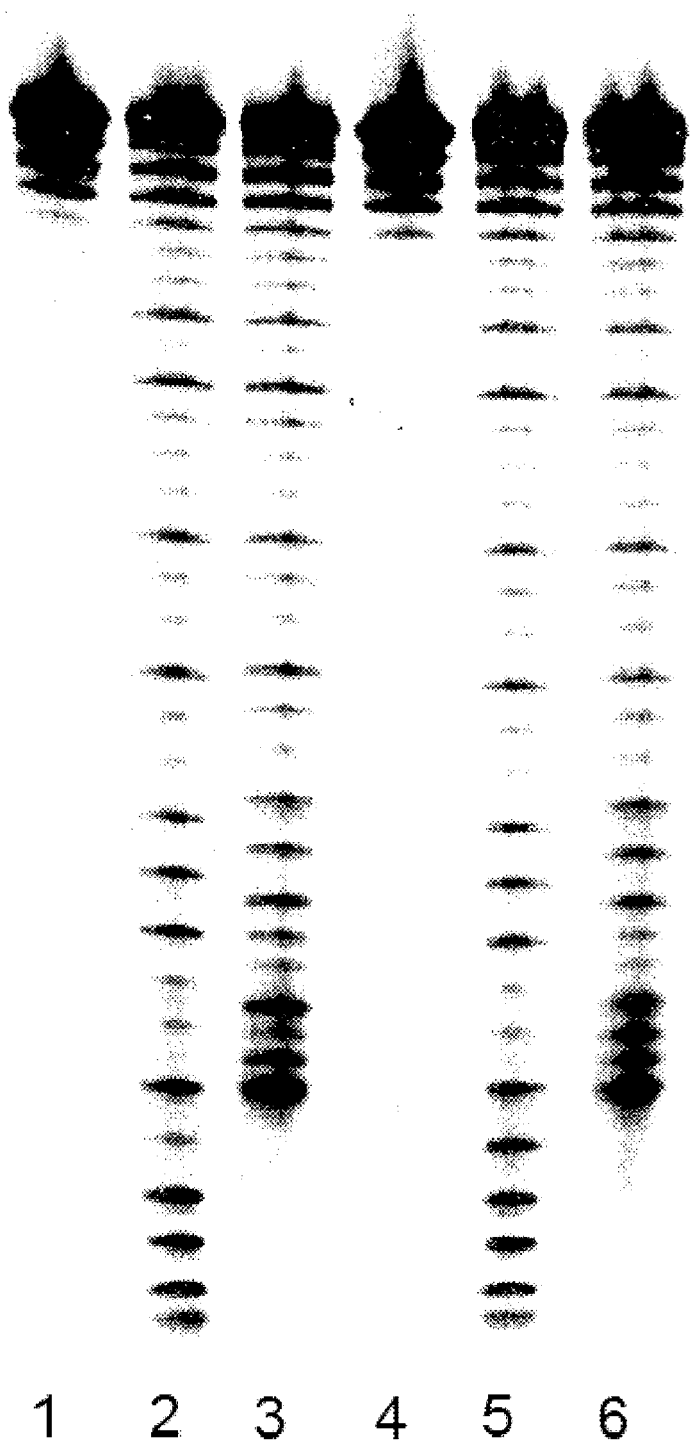
FIG. 2 is the image generated by a fluorescence imager showing thermal degradation of oligonucleotides containing or lacking a 3' phosphate group.

In FIG. 2, lanes 1-3 contain the TET-labeled oligonucleotide 78 and lanes 4-6 contain the TET-labeled oligonucleotide 79. Lanes 1 and 4 contain products of reactions that were not heat treated. Lanes 2 and 5 contain products from reactions that were heat treated and lanes 3 and 6 contain products from reactions that were heat treated, then subjected to phosphatase treatment.

As shown in FIG. 2, heat treatment causes significant breakdown of the 5'-TET-labeled DNA, generating a ladder of degradation products (FIG. 2, lanes 2, 3, 5 and 6). Band intensities correlate with purine and pyrimidine base positioning in the oligonucleotide sequences, indicating that backbone hydrolysis may occur through formation of abasic intermediate products that have faster rates for purines than for pyrimidines (Lindahl and Karlström, Biochem., 12:5151 [1973]).

Dephosphorylation decreases the mobility of all products generated by the thermal degradation process, with the most pronounced effect observed for the shorter products (FIG. 2, lanes 3 and 6). This demonstrates that thermally degraded products possess a 3' end terminal phosphoryl group that can be removed by dephosphorylation with CIAP. Removal of the phosphoryl group decreases the overall negative charge by 2. Therefore, shorter products that have a small number of negative charges are influenced to a greater degree upon the removal of two charges. This leads to a larger mobility shift in the shorter products than that observed for the larger species.

The products generated by the CLEAVASE enzyme do not contain this additional 3' phosphate. Therefore, if an assay is designed such that the desired reaction products contain one or two positive charges, similar thermal breakdown products would be neutral or negative. This allows for easy separation of product from background via the reverse charge methods described below.

b) Dephosphorylation of Short Amino-Modified Oligonucleotides can Reverse the Net Charge of the Labeled Product To demonstrate how oligonucleotides can be transformed from net negative to net positively charged compounds, the four short amino-modified oligonucleotides labeled 70, 74, 75 and 76 and shown in FIGS. 3-4 were synthesized. All four modified oligonucleotides possess Cy3 dyes positioned at the 5'-end, which individually are positively charged under reaction and isolation conditions described in this Example. Compounds 70 and 74 contain two amino modified thymidines that, under reaction conditions, display positively charged R—$NH_3^+$ groups attached at the C5 position through a $C_{10}$ or $C_6$ linker, respectively. Because compounds 70 and 74 are 3'-end phosphorylated, they consist of four negative charges and three positive charges. Compound 75 differs from 74 in that the internal $C_6$ amino modified thymidine phosphate in 74 is replaced by a thymidine methyl phosphonate. The phosphonate backbone is uncharged and so there are a total of three negative charges on compound 75. This gives compound 75 a net negative one charge. Compound 76 differs from 70 in that the internal amino modified thymidine is replaced by an internal cytosine phosphonate. The $pK_a$ of the N3 nitrogen of cytosine can be from 4 to 7. Thus, the net charges of this compound, can be from −1 to 0 depending on the pH of the solution. For the simplicity of analysis, each group is assigned a whole number of charges, although it is realized that, depending on the $pK_a$ of each chemical group and ambient pH, a real charge may differ from the whole number assigned. It is assumed that this difference is not significant over the range of pHs used in the enzymatic reactions studied here.

Dephosphorylation of these compounds, or the removal of the 3' end terminal phosphoryl group, results in elimination of two negative charges and generates products that have a net positive charge of one. In this experiment, the method of isoelectric focusing (IEF) was used to demonstrate a change from one negative to one positive net charge for the described substrates during dephosphorylation.

Substrates 70, 74, 75 and 76 were synthesized by standard phosphoramidite chemistries and deprotected for 24 hours at 22° C. in 14 M aqueous ammonium hydroxide solution, after which the solvent was removed in vacuo. The dried powders were resuspended in 200 µl of $H_2O$ and filtered through 0.2 µm filters. The concentration of the stock solutions was estimated by UV-absorbance at 261 nm of samples diluted 200-fold in $H_2O$ using a spectrophotometer (Spectronic Genesys 2, Milton Roy, Rochester, N.Y.).

Dephosphorylation of compounds 70 and 74, 75 and 76 was accomplished by treating 10 µl of the crude stock solutions (ranging in concentration from approximately 0.5 to 2 mM) with 2 units of CIAP in 100 µl of CIAP buffer (Promega) at 37° C. for 1 hour. The reactions were then heated to 75° C. for 15 min. in order to inactivate the CIAP. For clarity, dephosphorylated compounds are designated 'dp'. For example, after dephosphorylation, substrate 70 becomes 70dp.

To prepare samples for IEF experiments, the concentration of the stock solutions of substrate and dephosphorylated product were adjusted to a uniform absorbance of $8.5 \times 10^{-3}$ at 532 nm by dilution with water. Two microliters of each sample were analyzed by IEF using a PhastSystem electrophoresis unit (Pharmacia) and PhastGel IEF 3-9 media (Pharmacia) according to the manufacturer's protocol. Separation was performed at 15° C. with the following program: pre-run; 2,000 V, 2.5 mA, 3.5 W, 75 Vh; load; 200 V, 2.5 mA, 3.5 W, 15 Vh; run; 2,000 V; 2.5 mA; 3.5 W, 130 Vh. After separation, samples were visualized by using the FMBIO Image Analyzer (Hitachi) fitted with a 585 nm filter. The resulting imager scan is shown in FIG. 18.

Figure 18:
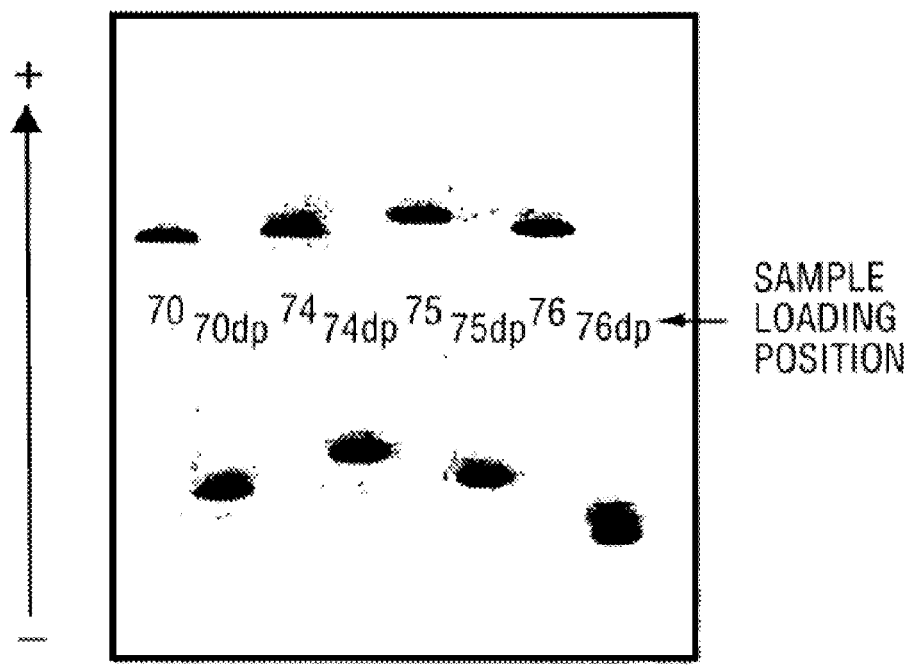
FIG. 18 is the image generated by a fluorescence imager scan of an IEF gel showing the migration of substrates 70, 70dp, 74, 74dp, 75, 75dp, 76 and 76dp.

FIG. 18 shows results of IEF separation of substrates 70, 74, 75 and 76 and their dephosphorylated products. The arrow labeled "Sample Loading Position" indicates a loading line, the '+' sign shows the position of the positive electrode and the '−' sign indicates the position of the negative electrode.

The results shown in FIG. 18 demonstrate that substrates 70, 74, 75 and 76 migrated toward the positive electrode, while the dephosphorylated products 70dp, 74dp, 75dp and 76dp migrated toward negative electrode. The observed difference in mobility direction was in accord with predicted net charge of the substrates (minus one) and the products (plus one). Small perturbations in the mobilities of the phosphorylated compounds indicate that the overall pIs vary. This was also true for the dephosphorylated compounds. The presence of the cytosine in 76dp, for instance, moved this compound further toward the negative electrode, which was indicative of a higher overall pI relative to the other dephosphorylated compounds. It is important to note that additional positive charges can be obtained by using a combination of natural amino modified bases (70dp and 74dp) along with uncharged methylphosphonate bridges (products 75dp and 76dp).

The results shown above demonstrate that the removal of a single phosphate group can flip the net charge of an oligonucleotide to cause reversal in an electric field, allowing easy separation of products, and that the precise base composition of the oligonucleotides affect absolute mobility but not the charge-flipping effect.

Example 2

Detection of Specific Cleavage Products in the Invader-Directed Cleavage Reaction by Charge Reversal In this Example the ability to isolate products generated in the INVADER-directed cleavage assay from all other nucleic acids present in the reaction cocktail using charge reversal is demonstrated.

Enzymes for Cleavage Assays

The CLEAVASE A/G enzyme was prepared as described in U.S. Pat. No. 6,090,606, and PCT application WO 98/23774 (herein incorporated by reference in their entireties); Afu FEN 1 and Pfu FEN1 were isolated as described in WO 98/23774. Two other enzymes used in these studies, CLEAVASE TthAKK enzyme and Ave FEN1 nuclease, were produced as described in the following sections.

Cloning and Expression of Cleavase TthAKK

Initial TthPol Isolation

Genomic DNA was prepared from 1 vial of dried *Thermus thermophilus* strain HB-8 from ATCC (ATCC #27634). The DNA polymerase gene was amplified by PCR using the following primers: 5'-CACGAATTCCGAGGCGATGCTTC-CGCTC-3' (SEQ ID NO:5) and 5'-TCGACGTCGACTAAC-CCTTGGCGGAAAGCC-3' (SEQ ID NO:6). The resulting PCR product was digested with EcoRI and SalI restriction endonucleases and inserted into EcoRI/Sal I digested plasmid vector pTrc99G. The pTrc99G vector was created by modification of the pTrc99A vector (Pharmacia) to remove the G at position 270 of the pTrc99A map. To this end, pTrc99A plasmid DNA was cut with NcoI and the recessive 3' ends were filled-in using the Klenow fragment of *E. coli* polymerase I in the presence of all four dNTPs at 37° C. for 15 min. After inactivation of the Klenow fragment by incubation at 65° C. for 10 min, the plasmid DNA was cut with EcoRI and the ends were again filled-in using the Klenow fragment in the presence of all four dNTPs at 37° C. for 15 min. The Klenow fragment was then inactivated by incubation at 65° C. for 10 min. The plasmid DNA was ethanol precipitated, recircularized by ligation, and used to transform *E. coli* JM109 cells (Promega). The pTrc99G plasmid DNA was isolated from single colonies, and deletion of the G at position 270 (by reference to the pTrc99A map) was confirmed by DNA sequencing. Insertion of the Tth DNA into this vector as described above created the plasmid pTrcTth-1. This Tth polymerase construct is missing a single nucleotide that was inadvertently omitted from the 5' oligonucleotide, resulting in the polymerase gene being out of frame. This mistake was corrected by site specific mutagenesis of pTrcTth-1 using the TRANSFORMER Site Directed Mutagenesis Kit (Clontech) according to the manufacturer's instructions, and the following oligonucleotide:

5'-GCATCGCCTCGGAATTCATGGTC-3' (SEQ ID NO:7), to create the plasmid pTrcTth-2. The protein and the nucleic acid sequence encoding the protein are referred to as TthPol, and are listed as SEQ ID NOS:8 and 9 respectively.

Modified TthPol Gene: Tth DN

The Tth DN construct was created by mutating the Tth-Pol-2 described above. The sequence encoding an aspartic acid at position 787 was changed by site-specific mutagenesis as described above to a sequence encoding asparagine. Mutagenesis of pTrcTth-2 with the following oligonucleotide:

5'-CAGGAGGAGCTCGTTGTGGACCTGGA-3' (SEQ ID NO:10) was performed to create the plasmid pTrcTthDN. The mutant protein, termed Tth DN, and protein coding nucleic acid sequence are SEQ ID NOS:11 and 12, respectively.

Tth DN HT

A six-amino acid histidine tag (his-tags) was added onto the carboxy terminus of Tth DN. The site-directed mutagenesis was performed using the TRANSFORMER Site Directed Mutagenesis Kit (Clontech) according to the manufacturer's instructions. The mutagenic oligonucleotides used on the plasmid pTth DN was sequence 5'-TGCCTGCAG-GTCGACGCTAGCTAGTGGTGGTGGTG-GTGGTGACCCTTGGCG GAAAGCC-3' (SEQ ID NO:13), sequence 136-037-05. The selection primer Trans Oligo AlwNI/SpeI (Clontech, catalog #6488-1) was used for both mutagenesis reactions. The resulting mutant gene was termed Tth DN HT (SEQ ID NO:14, nucleic acid sequence; SEQ ID NO:15, amino acid sequence).

Purification of Tth DN HT

The Tth DN HT protein was expressed in *E. coli* strain JM109 as described above. After ammonium sulfate precipitation and centrifugation, the protein pellet was suspended in 0.5 ml of Q buffer (50 mM Tris-HCl, pH 8.0, 0.1 mM EDTAm 0.1% Tween 20). The protein was further purified by affinity chromatography using His-Bind Resin and Buffer Kit (Novagen) according to the manufacturer's instructions. 1 ml of His-Bind resin was transferred into a column, washed with 3 column volumes of sterile water, charged with 5 volumes of 1× Charge Buffer, and equilibrated with 3 volumes of 1× Binding Buffer. Four ml of 1× Binding Buffer was added to the protein sample and the sample solution was loaded onto the column. After washing with 3 ml of 1× Binding Buffer and 3 ml of 1× Wash Buffer, the bound His-Tag protein was eluted with 1 ml of 1× Elute Buffer. The pure enzyme was then dialyzed in 50% glycerol, 20 mM Tris-HCl, pH 8.0, 50 mM KCl, 0.5% Tween 20, 0.5% Nonidet P40, and 100 µg.ml BSA. Enzyme concentrations were determined by measuring absorption at 279 nm.

Generation of Tth DN RX HT

Mutagenesis was performed to introduce 3 additional, unique restriction sites into the polymerase domain of the Tth DN HT enzyme. Site specific mutagenesis was performed using the Transformer Site-Directed Mutagenesis Kit from (Clontech) according to manufacturer's instructions. One of two different selection primers, Trans Oligo AlwNI/SpeI or Switch Oligo SpeI/AlwNI (Clontech catalog #6488-1 or catalog #6373-1) was used for all mutagenesis reactions described. The selection oligo used in a given reaction is dependent on the selection restriction site present in the vector. All mutagenic primers were synthesized by standard synthetic chemistry. Resultant colonies were expressed in *E. coli* strain JM109.

The Not I site (amino acid position 328) was created using the mutagenic primer 5'-GCCTGCAGGGGCGGCCGCGT-GCACCGGGCA (SEQ ID NO:16) corresponding to the sense strands of the Tth DN HT gene. The BstI (amino acid position 382) and NdeI (amino acid position 443) sites were introduced using sense strand mutagenic primers 5'-CTC-CTGGACCCTTCGAACACCACCCC (SEQ ID NO:17) and 5'-GTCCTGGCCCATATGGAGGCCAC (SEQ ID NO:18), respectively. The mutant plasmid was over-expressed and purified using Qiagen QiaPrep Spin Mini Prep Kit (cat. #27106). The vector was tested for the presence of the restriction sites by DNA sequencing and restriction mapping. The construct is termed Tth DN RX HT (DNA sequence SEQ ID NO:19; amino acid sequence SEQ ID NO:20)

Addition of Point Mutations

Plasmid DNA was purified from 200 ml of JM109 overnight culture using QIAGEN Plasmid Maxi Kit (QIAGEN) according to the manufacturer's protocol to obtain enough starting material for all mutagenesis reactions. All site-specific mutations were introduced using the Transformer Site Directed mutagenesis Kit (Clontech) according to the manufacturer's protocol. One of two different selection primers, Trans Oligo AlwNI/SpeI or Switch Oligo SpeI/AlwNI (Clontech, Palo Alto Calif. catalog #6488-1 or catalog #6373-1) was used for all mutagenesis reactions described. The selection oligo used in a given reaction is dependent on the restriction site present in the vector. All mutagenic primers were synthesized by standard synthetic chemistry. Resultant colonies for both types of reactions were *E. coli* strain JM109. Expression and purification of the mutant protein was done as detailed above.

Construction of Tth DN RX HT H786A

Site specific mutagenesis was performed on pTrc99G Tth DN RX HT DNA using the mutagenic primer 583-001-04: 5'-CAG GAG GAG CTC GTT GGC GAC CTG GAG GAG-3' (SEQ ID NO:21) to generate the H786A mutant enzyme (DNA sequence SEQ ID NO:22; amino acid sequence SEQ ID NO:23).

Construction of Tth DN RX HT (H786A/G506K/Q509K)

Starting with the mutant Tth DN RX HT H786A, generated above, site specific mutagenesis was done using the mutagenic primer 604-022-02: 5'-GGA GCG CTT GCC TGT CTT CTT CGT CTT CTT CAA GGC GGG AGG CCT-3' (SEQ ID NO:24) to generate this variant termed "Cleavase TthAKK", (DNA sequence SEQ ID NO:25; amino acid sequence SEQ ID NO:26).

Large Scale Preparation of Recombinant Proteins

The recombinant proteins were purified by the following technique which is derived from a Taq DNA polymerase preparation protocol (Engelke et al., Anal. Biochem., 191: 396 [1990]) as follows. *E. coli* cells (strain JM109) containing either pTrc99A TaqPol, pTrc99GTthPol were inoculated into 3 ml of LB containing 100 mg/ml ampicillin and grown for 16 hrs at 37° C. The entire overnight culture was inoculated into 200 ml or 350 ml of LB containing 100 mg/ml ampicillin and grown at 37° C. with vigorous shaking to an $A_{600}$ of 0.8. IPTG (1 M stock solution) was added to a final concentration of 1 mM and growth was continued for 16 hrs at 37° C.

The induced cells were pelleted and the cell pellet was weighed. An equal volume of 2×DG buffer (100 mM Tris-HCl, pH 7.6, 0.1 mM EDTA) was added and the pellet was suspended by agitation. Fifty mg/ml lysozyme (Sigma) were added to 1 mg/ml final concentration and the cells incubated at room temperature for 15 min. Deoxycholic acid (10% solution) was added dropwise to a final concentration of 0.2% while vortexing. One volume of $H_2O$ and 1 volume of 2×DG buffer were added, and the resulting mixture was sonicated for 2 minutes on ice to reduce the viscosity of the mixture. After sonication, 3 M $(NH_4)_2SO_4$ was added to a final concentration of 0.2 M, and the lysate was centrifuged at 14000×g for 20 min at 4° C. The supernatant was removed and incubated at 70° C. for 60 min at which time 10% polyethylamine (PEI) was added to 0.25%. After incubation on ice for 30 min., the mixture was centrifuged at 14,000×g for 20 min at 4° C. At this point, the supernatant was removed and the protein precipitated by the addition of $(NH_4)_2SO_4$ as follows.

Two volumes of 3 M $(NH_4)_2SO_4$ were added to precipitate the protein. The mixture was incubated overnight at room temperature for 16 hrs centrifuged at 14,000×g for 20 min at 4° C. The protein pellet was suspended in 0.5 ml of Q buffer (50 mM Tris-HCl, pH 8.0, 0.1 mM EDTA, 0.1% Tween 20). The suspended protein preparations were quantitated by determination of the $A_{279}$ dialyzed and stored in 50% glycerol, 20 mM Tris HCl, pH8.0, 50 mM KCl, 0.5% Tween 20, 0.5% Nonidet P-40, with 100 µg/ml BSA.

Cloning and Expression of AveFEN1 Nuclease

A common method for cloning new members of a gene family is to run PCR reactions using degenerate oligonucleotides complementary to conserved amino acid sequences in that family, and then to clone and sequence the gene-specific PCR fragments. This sequence information can then be used to design sense and anti-sense gene-specific primers which can be used in PCR walking reactions (Nucleic Acids Res. 1995a. 23(6)1087-1088) to obtain the remainder of the gene sequence. The sequences obtained from the sense and anti-sense PCR walks can then be combined to generate the DNA sequence for the entire open reading frame (ORF) of the gene of interest. Once the entire ORF is known, primers specific to both the 5' and the 3' end of the gene can be designed, and PCR reactions can be performed on genomic DNA to amplify the gene in its entirety. This organism-specific, amplified fragment can then be cloned into an expression vector, and via methods know in the art, and detailed below, the protein of interest can be expressed and purified.

A. Degenerate PCR and PCR Walking to Obtain the Sequence of the Ave FEN1 Gene

The protein sequences of the FEN1 genes from *Pyrococcus furiosus* (SEQ ID NO:27) *Methanococcus jannaschii* (SEQ ID NO:28), *Methanobacterium thermoautotrophicum* (SEQ ID NO:29), and *Archaeoglobus fulgidus* (SEQ ID NO:30) were aligned and blocks of conserved amino acids were identified. The conserved sequence blocks VFDG (valine, phenylalanine, aspartic acid, glycine), EGEAQ (glutamic acid, glycine, glutamic acid, alanine, glutamine), SQDYD (serine, glutamine, aspartic acid, tyrosine, aspartic acid), and GTDYN/GTDFN (glycine, threonine, aspartic acid, tyrosine or phenylalanine, asparagine) were chosen as sequences that would likely be present in all Archaeal FEN1 genes. Degenerate oligonucleotides were designed for each of these conserved sequence blocks. In addition to the FEN1 gene specific portion of the oligonucleotides a 15-nucleotide tail was added to the 5' end of the oligonucleotides to enable nested PCR. A different tail sequence was used depending on whether the degenerate oligonucleotide targets the sense or antisense strand of the FEN1 gene.

Forward and/or reverse versions of the oligonucleotides were made and target the sense and antisense strands of the FEN1 gene respectively. The oligonucleotides are VFDG-Fwd (SEQ ID NO:31), EGEAQ-Fwd (SEQ ID NO:32) QDYD-Fwd (SEQ ID NO:33), EGEAQ-Rev (SEQ ID NO:34), SQDYD-Rev1 (SEQ ID NO:35), SQDYD-Rev2 (SEQ ID NO:36), and GTDYN-Rev (SEQ ID NO:37). Two oligonucleotides were made for the SQDYD-Rev sequence because serine is encoded by 6 different codons. For use in PCR, the SQDYD-Rev1 and SQDYD-Rev2 oligonucleotides were mixed in a ratio of 1:2. For the QDYD-Fwd oligonucleotide, the requirement for mixing was avoided by targeting only the last four amino acids of the conserved SQDYD sequence. The GTDYN-Rev oligonucleotide also recognizes the sequence GTDFN since the codons for tyrosine and phenylalanine share 2 of 3 nucleotides.

First, genomic DNA was prepared from 1 vial of the live bacterial strain as described below. All bacterial strains were obtained from the DSMZ (Deutsche Sammlung von Mikroorganismen und Zellkulturen, *Acidianus ambivalens*-DSM #3772). When the cells were lyophilized, they were resuspended in 200 µl of TNE (10 mM Tris HCL, pH 8.0, 1 mM EDTA, 100 mM NaCl). When the cells were in liquid suspension, they were spun down at 20,000×G for 2 minutes and the cell pellets were resuspended in 200 µl of TNE. 20 µl of 20% SDS (sodium dodecylsulfate) and 2 µl of 1 mg/ml proteinase K were added and the suspension was incubated at 65° C. for 30 minutes. The lysed cell suspension was extracted in sequential order with buffered phenol, 1:1 phenol:chloroform, and chloroform. The nucleic acid was precipitated by the addition of on equal volume of cold 100% ethanol. The nucleic acid was pelleted by spinning at 20,000×G for 5 minutes. The nucleic acid pellet was washed with 70% ethanol, air dried and resuspended in 50 µl of TE (10 mM Tris HCL, pH 8.0, 1 mM EDTA). The final DNA pellet was re-suspended in 50 µl of TE (10 mM Tris HCl, pH 8.0, 1 mM EDTA).

Both reactions of the nested PCR were done using the Advantage cDNA PCR kit (Clontech) according to manufacturer's instructions using a final concentration of 1 µM for all oligonucleotides. The first reaction is done in a 20 µl volume with one of the 6 possible combinations of forward and reverse degenerate oligonucleotides, and includes either 1 µl of the genomic DNA preparation described above. The cycling conditions were 20 cycles of 95° C. for 15 seconds, 50° C. or 55° C. for 15 seconds, and 68° C. for 30 seconds. The second reactions utilize primers that have the same sequence as the 5' tail sequence of the degenerate oligonucleotides described above. The two primers are 203-01-01 (SEQ ID NO:38) and 203-01-02 (SEQ ID NO:39). The second reaction is carried out exactly as described for the first reaction, except 30 cycles are done instead of 20 and the reaction volume is 25 µl. Following the second PCR, 5 µl of the reaction were loaded on a 2% or 4% agarose gel and the DNA was visualized by ethidium bromide staining. The expected product sizes based on the previously identified FEN1 sequences for all primer pairs are as follows: VFDG-Fwd and EGEAQ-Rev; 275 base pairs, VFDG-Fwd and SQDYD-Rev; 325 base pairs, VFDG Fwd and GTDYN-Rev; 510 base pairs, EGEAQ-Fwd and SQDYD-Rev; 100 base pairs, EGEAQ-Fwd and GTDYN-Rev; 290 base pairs, QDYD-Fwd and GTDYN-Rev; 230 base pairs. The primer pair, VFDG-Fwd and EGEAQ-Rev was able to generate a correctly sized DNA product for all samples attempted. The primer pair, VFDG-Fwd and GTDYN-Rev was able to generate a correctly sized DNA product for most of the DNA samples attempted.

When a DNA product of the expected size was made by the degenerate PCR, that DNA fragment was isolated and cloned into pGEM-T Easy (Promega) using the pGEM-T Easy ligation kit according to the manufacturer's instructions. The DNA sequence was determined and the sequence was used to generate sense and antisense genome walking oligonucleotides for cloning the remainder of the FEN1 gene. The oligonucleotides were designed according to the parameters of the GenomeWalker kit (Clontech) which was used prepare the various genomic DNA samples for the genome walking PCR reactions.

The genomic DNA was randomly amplified using a random 12-mer oligonucleotide. One hundred-µl PCR reactions were set up with the Advantage cDNA PCR kit (Clontech) and contained 10 µl of genomic DNA and 15 µM random 12-mer oligonucleotide. 50 cycles were carried out with the following parameters: 95° C. for 30 seconds, 50° C. for 30 seconds, 68° C. for 5 minutes. After the PCR reactions were complete, amplified DNA was purified with the High Pure PCR Product Purification kit (Boehringer Mannheim). The purified DNA was eluted into a total of 200 µl of 10 mM Tris HCL, pH 8.5.

The genome walking protocol consists of 3 steps. First, a genomic DNA sample is cut with 5 different blunt-end restriction enzymes in 5 separate reactions. Second, the cut DNA is ligated to an adapter which serves as a tag sequence and also is designed to prevent background amplification. Third, the ligated DNA is amplified with a gene-specific primer and a primer with the same sequence as a portion of the adapter sequence.

50 µl restriction digests contained 30 µl of randomly amplified genomic DNA and the Dra I restriction enzyme. After 4 hours at 37° C., the cut DNA was purified with either GENECLEANII (Bio 101) or QIAEX II (Qiagen) according to manufacturer's instructions. DNA was eluted into 10 µl of 10 mM Tris HCl, pH 8.5 in either case. 5.6 µl of this cut DNA was used in 10 µl ligation reactions containing 6 µM GenomeWalker adapter. Reactions were carried out at room temperature overnight followed by heating at 70° C. for 10 minutes to inactivate the T4 DNA ligase. The ligation reactions were then diluted with 70 µl of TE (10 mM Tris HCl, pH 8.0, 1 mM EDTA).

One µl of the diluted ligation mix was used in 25 µl PCR reactions with 0.2 µM gene-specific primer and 0.2 µM primer AP-1 (Clontech) which has the same sequence as the 5' portion of the GenomeWalker adapter. Ten reactions were done for each DNA sample. Five antisense walk PCR reactions (for the 5 different restriction enzymes used to cut the genomic sample) were done using the sense gene-specific primer and five sense walk PCR reactions were done using the antisense gene-specific primer for each DNA sample. The cycling parameters were as recommended by the Universal Genome Walking kit (Clontech) and were as follows: 7 cycles of 94° C. for 25 seconds and 72° C. for 3 minutes, 32 cycles of 94° C. for 25 seconds and 67° C. for 3 minutes, followed by 67° C. for 7 minutes.

The *Archaeoglobus veneficus* (Ave) genome walks were done as follows. The primary antisense primer was Ave 34AS (SEQ ID NO:40) and the primary sense primer was Ave 65S (SEQ ID NO:41). Nested PCR reactions were done using the nested primer AP-2 and either the nested antisense primer Ave 32AS (SEQ ID NO:42) or the nested sense primer Ave 67S (SEQ ID NO:43). 25-µl nested reactions were done as described above for the primary PCR walk reactions. The primary reactions were diluted 1:50 in $H_2O$ and 0.5 µl of those dilutions were added to the nested PCR reactions. The cycling parameters for the nested PCR reactions were as recommended by the Universal Genome Walking kit (Clontech) and are as follows: 5 cycles of 94° C. for 25 seconds and 72° C. for 3 minutes, 20 cycles of 94° C. for 25 seconds and 67° C. for 3 minutes, followed by 7 minutes at 67° C. The nested antisense PCR reaction on Stu I cut Ave genomic sample generated a 1 kilobase DNA product which was cloned into pGEM-T Easy (Promega) following manufacturer's instructions and sequenced. The nested sense PCR reaction on Eco RV cut Ave genomic sample generated a 1.1 kilobase product which was cloned into pGEM-T Easy (Promega) following manufacturer's instructions and sequenced.

Cloning of Ave FEN-1 Nuclease I into an Expression Vector

PCR reactions were performed using the primers designed above and genomic DNA from the organism of interest. The PCR products were gel purified and then cut with restriction endonucleases corresponding to the sites incorporated in the PCR primers. The cut PCR products were then purified away from the smaller digest fragments and these cut products were cloned into an expression vector. In some cases, this was the final step of the cloning process, prior to transformation and protein expression/purification. In some cases a fifth step was needed. In some cases, a mutagenesis step had to be performed to remove any nucleotides that were incorporated into the ORF as a result of primer sequences required for cloning.

Finally, a bacterial host (e.g., *E. coli* JM109) was transformed with the expression vector containing the cloned FEN-1, and protein expression and purification were done as detailed below.

The cloning of a FEN-1 from *Archaeaglobus veneficus* (Ave) was performed as described above using the DSM #11195 genomic DNA and PCR primers Ave 5'-3' TAAC-GAATTCGGTGCAGACATAGGCGAACTAC (SEQ ID NO:44) and Ave 3'-5' CGGTGTCGACTCAGGAAAAC-CACCTCTCAAGCG (SEQ ID NO:45). The mutagenic oligonucleotide used was Ave ΔR1-5' CACAGGAAACAGAC-CATGGGTGCAGACATAGGCGAAC (SEQ ID NO:46). The open reading frame (ORF) encoding the Ave FEN-1 endonuclease is provided in SEQ ID NO:47; the amino acid sequence encoded by this ORF is provided in SEQ ID NO:48.

Large Scale Preparation of Recombinant Ave FEN-1 Protein

Ave FEN-1 protein was purified by the following technique, which is derived from a Taq DNA polymerase preparation protocol (Engelke et al., Anal. Biochem., 191:396 [1990]) as follows. *E. coli* cells (strain JM109) containing the construct described above were inoculated into 3 ml of LB (Luria Broth) containing 100 µg/ml ampicillin and grown for 16 hrs at 37° C. The entire overnight culture was inoculated into 200 ml or 350 ml of LB containing 100 µg/ml ampicillin and grown at 37° C. with vigorous shaking to an $A_{600}$ of 0.8. IPTG (1 M stock solution) was added to a final concentration of 1 mM and growth was continued for 16 hrs at 37° C.

The induced cells were pelleted and the cell pellet was weighed. An equal volume of 2×DG buffer (100 mM Tris-HCl, pH 7.6, 0.1 mM EDTA) was added and the pellet was resuspended by agitation. Fifty mg/ml lysozyme (Sigma, St. Louis, Mo.) was added to 1 mg/ml final concentration and the cells were incubated at room temperature for 15 min. Deoxycholic acid (10% solution) was added dropwise to a final concentration of 0.2% while vortexing. One volume of $H_2O$ and 1 volume of 2×DG buffer was added and the resulting mixture was sonicated for 2 minutes on ice to reduce the viscosity of the mixture. After sonication, 3 M $(NH_4)_2SO_4$ was added to a final concentration of 0.2 M and the lysate was centrifuged at 14000×g for 20 min at 4° C. The supernatant was removed and incubated at 70° C. for 60 min at which time 10% polyethylamine (PEI) was added to 0.25%. After incubation on ice for 30 min., the mixture was centrifuged at 14,000×g for 20 min at 4° C. At this point, the supernatant was removed and the FEN-1 protein was precipitated by the addition of $(NH_4)_2SO_4$ as follows.

The FEN-1 protein was precipitated by the addition of solid $(NH_4)_2SO_4$ to a final concentration of 3 M (~75% saturated). The mixture was incubated on ice for 30 min and the protein was centrifuged at 14,000×g for 20 min at 4° C. The protein pellet was resuspended in 0.5 ml of Q buffer (50 mM Tris-HCl, pH 8.0, 0.1 mM EDTA, 0.1% Tween 20). The resuspended protein preparations were quantitated by determination of the $A_{279}$.

INVADER Assay Using Charged-balanced Probes

This experiment utilized the following Cy3-labeled oligonucleotide: 5'-Cy3-AminoT-AminoT-CTTTTCACCAGC-GAGACGGG-3' (SEQ ID NO:1; termed "oligo 61"). Oligo 61 was designed to release upon cleavage a net positively charged, labeled product. To test whether or not a net positively charged 5'-end labeled product would be recognized by the CLEAVASE enzymes in the INVADER-directed cleavage assay format, probe oligo 61 (SEQ ID NO:1) and INVADER oligonucleotide 67 (SEQ ID NO:2) were chemically synthesized on a DNA synthesizer (ABI 391) using standard phosphoramidite chemistries and reagents obtained from Glen Research (Sterling, Va.).

Each assay reaction comprised 100 fmoles of M 13 mp 18 single stranded DNA, 10 pmoles each of the probe (SEQ ID NO:1) and INVADER (SEQ ID NO:2) oligonucleotides, and 20 units of CLEAVASE A/G in a 10 μl solution of 10 mM MOPS, pH 7.4 with 100 mM KCl. Samples were overlaid with mineral oil to prevent evaporation. The samples were brought to 50° C., 55° C., 60° C., or 65° C. and cleavage was initiated by the addition of 1 μl of 40 mM $MnCl_2$. Reactions were allowed to proceed for 25 minutes and then were terminated by the addition of 10 μl of 95% formamide containing 20 mM EDTA and 0.02% methyl violet. The negative control experiment lacked the target M13mp18 and was run at 60° C. Five microliters of each reaction were loaded into separate wells of a 20% denaturing polyacrylamide gel (cross-linked 29: 1) with 8 M urea in a buffer containing 45 mM Tris-Borate (pH 8.3) and 1.4 mM EDTA. An electric field of 20 watts was applied for 30 minutes, with the electrodes oriented as indicated in FIG. 19B (i.e., in reverse orientation). The products of these reactions were visualized using the FMBIO fluorescence imager and the resulting imager scan is shown in FIG. 19B.

Figure 19A:
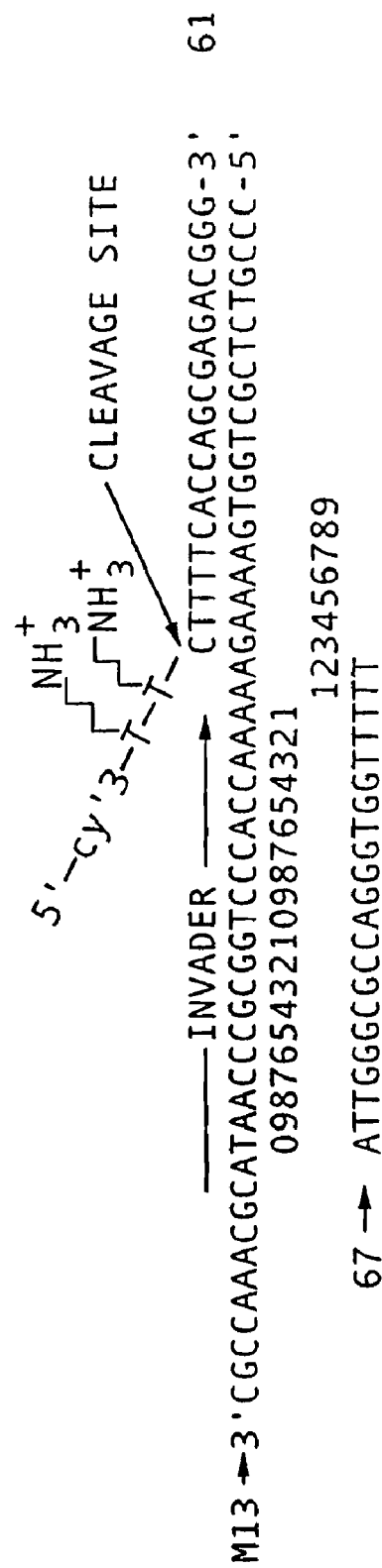
FIG. 19A provides a schematic showing an arrangement of a target-specific INVADER oligonucleotide (SEQ ID NO:2) and a target-specific probe oligonucleotide (SEQ ID NO:11) bearing a 5' Cy3 label along a target nucleic acid (SEQ ID NO:49).
Figure 19:
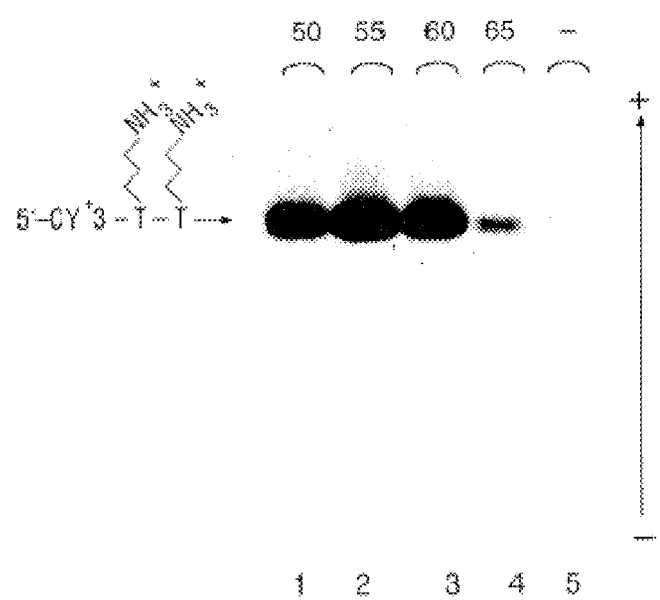
FIG. 19B is the image generated by a fluorescence imager showing the detection of specific cleavage products generated in an invasive cleavage assay using charge reversal (i.e., charge based separation of cleavage products).

FIG. 19A provides a schematic illustration showing an alignment of the INVADER (SEQ ID NO:2) and probe (SEQ ID NO:1) along the target M13mp18 DNA; only 53 bases of the M13mp18 sequence is shown (SEQ ID NO:49). The sequence of the INVADER oligonucleotide is displayed under the M13mp 18 target and an arrow is used above the M13mp18 sequence to indicate the position of the INVADER relative to the probe and target. As shown in FIG. 19A, the INVADER and probe oligonucleotides share a 2 base region of overlap.

In FIG. 19B, lanes 1-4 contain reactions performed at 50° C., 55° C., 60° C., and 65° C., respectively; lane 5 contained the control reaction (lacking target). In FIG. 19B, the products of cleavage are seen as dark bands in the upper half of the panel; the faint lower band seen appears in proportion to the amount of primary product produced and, while not limiting the invention to a particular mechanism, may represent cleavage one nucleotide into the duplex. The uncleaved probe does not enter the gel and is thus not visible. The control lane showed no detectable signal over background (lane 5). As expected in an invasive cleavage reaction, the rate of accumulation of specific cleavage product was temperature-dependent. Using these particular oligonucleotides and target, the fastest rate of accumulation of product was observed at 55° C. (lane 2) and very little product observed at 65° C. (lane 4).

When incubated for extended periods at high temperature, DNA probes can break non-specifically (i.e., suffer thermal degradation) and the resulting fragments contribute an interfering background to the analysis. The products of such thermal breakdown are distributed from single-nucleotides up to the full length probe. In this experiment, the ability of charge based separation of cleavage products (i.e., charge reversal) would allow the sensitive separation of the specific products of target-dependent cleavage from probe fragments generated by thermal degradation was examined.

To test the sensitivity limit of this detection method, the target M13 mp 18 DNA was serially diluted ten fold over than range of 1 fmole to 1 amole. The INVADER and probe oligonucleotides were those described above (i.e., SEQ ID NOS:2 and 1, respectively). The invasive cleavage reactions were run as described above with the following modifications: the reactions were performed at 55° C., 250 mM or 100 mM KGlu was used in place of the 100 mM KCl and only 1 pmole of the INVADER oligonucleotide was added. The reactions were initiated as described above and allowed to progress for 12.5 hours. A negative control reaction that lacked added M13 m18 target DNA was also run. The reactions were terminated by the addition of 10 μl of 95% formamide containing 20 mM EDTA and 0.02% methyl violet, and 5 μl of these mixtures were electrophoresed and visualized as described above. The resulting imager scan is shown in FIG. 20.

Figure 20:
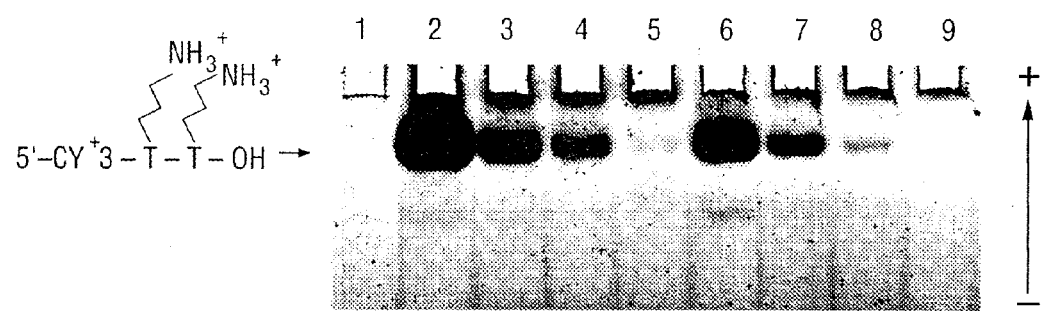
FIG. 20 is the image generated by a fluorescence imager that depicts the sensitivity of detection of specific cleavage products generated in an invasive cleavage assay using charge reversal.

In FIG. 20, lane 1 contains the negative control; lanes 2-5 contain reactions performed using 100 mM KGlu; lanes 6-9 contain reactions performed using 250 mM KGlu. The reactions resolved in lanes 2 and 6 contained 1 fmole of target DNA; those in lanes 3 and 7 contained 100 amole of target; those in lanes 4 and 8 contained 10 amole of target and those in lanes 5 and 9 contained 1 amole of target. The results shown in FIG. 20 demonstrate that the detection limit using charge reversal to detect the production of specific cleavage products in an invasive cleavage reaction is at or below 1 attomole or approximately $6.02 \times 10^5$ target molecules. No detectable signal was observed in the control lane, which indicates that non-specific hydrolysis or other breakdown products do not migrate in the same direction as enzyme-specific cleavage products. The excitation and emission maxima for Cy3 are 554 and 568, respectively, while the FMBIO Imager Analyzer excites at 532 and detects at 585. Therefore, the limit of detection of specific cleavage products can be improved by the use of more closely matched excitation source and detection filters.

Example 3

Examination of the Effects of a 5' Positive Charge on the Rate of Invasive Cleavage Using the CLEAVASE A/G or Pfu FEN-1 Nucleases To investigate whether the positive charges on the 5' ends of probe oligonucleotides containing a positively charged adduct(s) have an effect on the ability of the CLEAVASE A/G or Pfu FEN-1 nucleases to cleave the 5' arm of the probe, the following experiment was performed.

Two probe oligonucleotides having the following sequences were utilized in INVADER reactions: Probe 34-180-1: (N-Cy3)$T_{NH2}T_{NH2}$CCAGAGCCTAATTTGCC AGT(N-fluorescein)A, where N represents a spacer containing either a Cy3 or fluorescein group (SEQ ID NOS:50 or 51, respectively) and Probe 34-180-2: 5'-(N-TET)TTCCA-GAGCC TAATTTGCCAGT-(N-fluorescein)A, where N represents a spacer containing either a TET or fluorescein group (SEQ ID NOS:52 or 53, respectively). Probe 34-180-1 (SEQ ID NO:50) has amino-modifiers on the two 5' end T residues and a Cy3 label on the 5' end, creating extra positive charges on the 5' end. Probe 34-180-2 (SEQ ID NO:52) has a TET label on the 5' end, with no extra positive charges. The fluorescein label on the 3' end of probe 34-180-1 enables the visualization of the 3' cleaved products and uncleaved probes together on an acrylamide gel run in the standard direction (i.e., with the DNA migrating toward the positive electrode). The 5' cleaved product of probe 34-180-1 has a net positive charge and will not migrate in the same direction as the uncleaved probe, and is thus visualized by resolution on a gel run in the opposite direction (i.e.; with this DNA migrating toward the negative electrode).

The cleavage reactions were conducted as follows. All conditions were performed in duplicate. Enzyme mixes for the Pfu FEN-1 and CLEAVASE A/G nucleases were assembled. Each 2 µl of the Pfu FEN-1 mix contained 100 ng of Pfu FEN-1 and 7.5 mM $MgCl_2$. Each 2 µl of the CLEAVASE A/G nuclease mix contained 26.5 ng of CLEAVASE A/G nuclease and 4.0 mM $MnCl_2$. Four master mixes containing buffer, M 13 mp 18, and INVADER oligonucleotides were assembled. Each 7 µl of mix 1 contained 5 fmol M13mp18, 10 pmoles INVADER oligonucleotide 123 (SEQ ID NO:54) in 10 mM HEPES (pH 7.2). Each 7 µl of mix 2 contained 1 fmol M13mp18, 10 pmoles INVADER oligonucleotide 123 in 10 mM HEPES (pH 7.2). Each 7 µl of mix 3 contained 5 fmol M13mp18, 10 pmoles INVADER oligonucleotide 123 in 10 mM HEPES (pH 7.2), 250 mM KGlu. Each 7 µl of mix 4 contained 1 fmol M13mp18, 10 pmoles INVADER oligonucleotide 123 in 10 mM HEPES (pH 7.2), 250 mM KGlu. For every 7 µl of each mix, 10 pmoles of either probe 34-180-1 (SEQ ID NO:50) or probe 34-180-2 (SEQ ID NO:52) were added. The DNA solutions described above were covered with 10 µl of CHILLOUT evaporation barrier and brought to 65° C. The reactions made from mixes 1-2 were started by the addition of 2 µl of the Pfu FEN-1 mix, and the reactions made from mixes 3-4 were started by the addition of 2 µl of the CLEAVASE A/G nuclease mix. After 30 minutes at 65° C., the reactions were terminated by the addition of 8 µl of 95% formamide containing 10 mM EDTA. Samples were heated to 90° C. for 1 minute immediately before electrophoresis through a 20% denaturing acrylamide gel (19:1 cross-linked) with 7 M urea, in a buffer containing 45 mM Tris-Borate (pH 8.3), 1.4 mM EDTA and a 20% native acrylamide gel (29:1 cross-linked) in a buffer containing 45 mM Tris-Borate (pH 8.3), 1.4 mM EDTA.

Figure 21A:
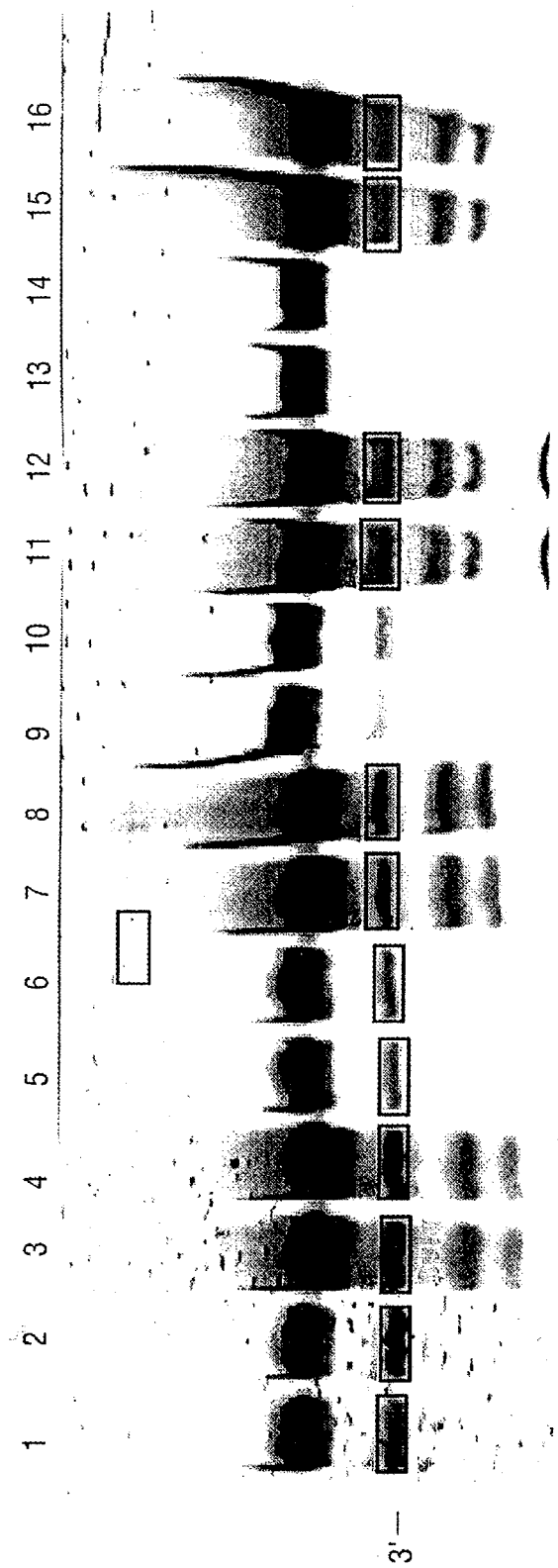
FIGS. 21A and 21B are images generated by a fluorescence imager showing the products produced using the CLEAVASE A/G and Pfu FEN-1 nucleases and probes having or lacking a 5' positive charge; the gel shown in FIG. 21A was run in the standard direction and the gel shown in FIG. 21B was run in the reverse direction.
Figure 21:
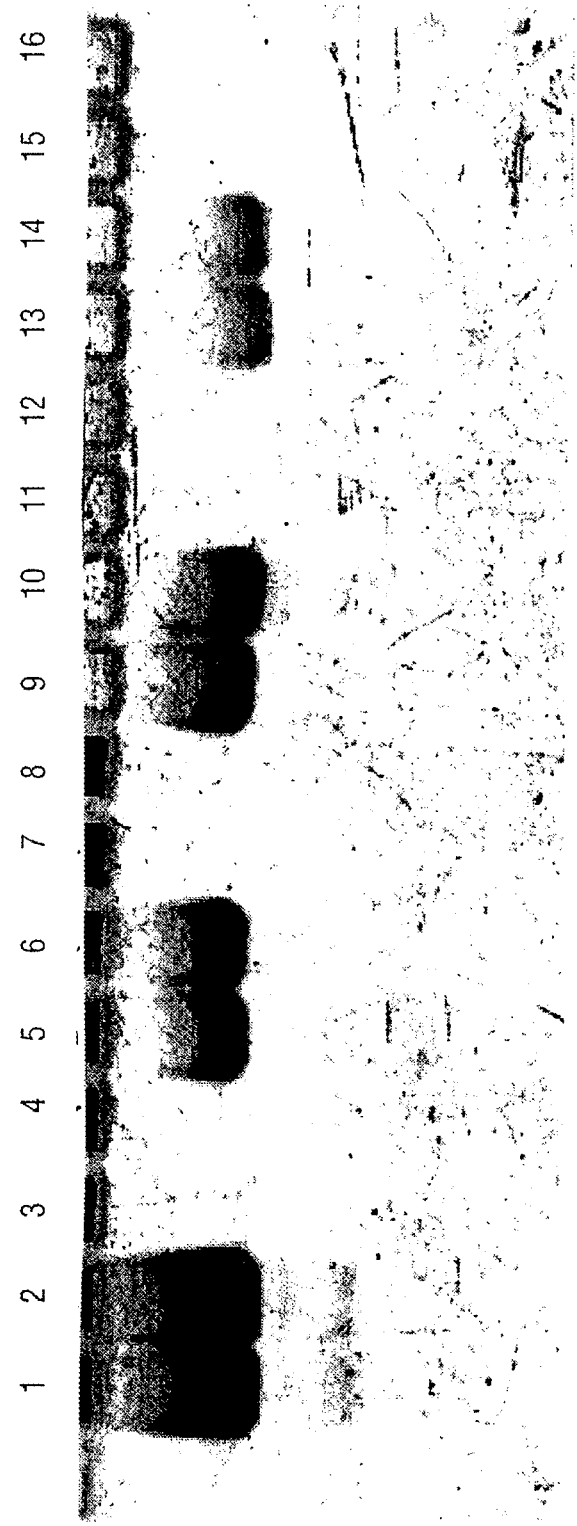

The products of the cleavage reactions were visualized following electrophoresis by the use of a Hitachi FMBIO fluorescence imager. The resulting images are shown in FIG. 21. FIG. 21A shows the denaturing gel, which was run in the standard electrophoresis direction, and FIG. 21B shows the native gel, which was run in the reverse direction. The reaction products produced by Pfu FEN-1 and CLEAVASE A/G nucleases are shown in lanes 1-8 and 9-16, respectively. The products from the 5 fmol M13mp18 and 1 fmol M13mp18 reactions are shown in lanes 1-4, 9-12 (5 fmol) and 5-8, 13-16 (1 fmol). Probe 34-180-1 is in lanes 1-2, 5-6, 9-10, 13-14 and probe 34-180-2 is in lanes 3-4, 7-8, 11-12, 15-16.

The fluorescein-labeled 3' end fragments from all cleavage reactions are shown in FIG. 21A, indicated by a "3'" mark at the left. The 3 nt 5' TET-labeled products are not visible in this Figure, while the 5' Cy3-labeled products are shown in FIG. 21B.

The 3' end bands in FIG. 21A can be used to compare the rates of cleavage by the different enzymes in the presence of the different 5' end labels. It can be seen from this band that regardless of the amount of target nucleic acid present, both the Pfu FEN-1 and the CLEAVASE A/G nucleases show more product from the 5' TET-labeled probe. With the Pfu FEN-1 nuclease this preference is modest, with only an approximately 25 to 40% increase in signal. In the case of the CLEAVASE A/G nuclease, however, there is a strong preference for the 5' TET label. Therefore, although when the charge reversal method is used to resolve the products, a substantial amount of product is observed from the CLEAVASE A/G nuclease-catalyzed reactions, the Pfu FEN-1 nuclease is a preferred enzyme for cleavage of Cy3-labeled probes.

Example 4

Manual Coupling of the 5' Phosphoramidite (Positively Charged Phosphoramidite or Neutral Phosphoramidite) to Solid Support This example demonstrates one means by which a phosphoramidite with a positive or neutral charge can be coupled to an oligonucleotide on a solid support. The coupling method described below is provided by way of example and not by way of limitation; other coupling methods may also prove to be effective.

A ¼ inch plug of Pyrex Brand Fiber Glass Wool (Aldrich, Cat# Z 25, 289-0) was tightly packed into a 2.5 ml gas-tight Hamilton syringe (VWR, Cat. #90168) using first a pasteur piptte or like device to drive the glass wool to the bottom of the syringe, followed by compression with the syringe plunger. The plunger was removed and approximately 40 mg of dry Control Pore Glass (CPG) support, coupled with oligonucleotide sequence SEQ ID NO:55 (still protected with the dimethoxy trityl [DMT] moiety at the 5' end) was added to the syringe, on top of the packed glass wool. The amount of the CPG added varies with the batch of CPG synthesized, and is specifically dependent on the amount of oligonucleotide loaded onto the solid support. The plunger was reinserted and depressed to pack the CPG coupled DNA onto the glass wool. A 5-inch, 18 gauge Luer Lock needle was secured to the syringe, and all reagents were drawn into the reaction vessel (the syringe) via the needle. The plunger remained in the syringe for the rest of the procedure.

Once the plunger was reinserted, the CPG-oligonucleotide complex was washed 3 times with methylene chloride (stored over 3-angstrom pore size, activated, Molecular Sieves [Aldrich, Cat. #20, 858-2]) by drawing 1 ml into the syringe via the needle, inverting 3-5 times and ejecting the wash solution by depressing the plunger.

Reactions were then washed with 1 ml of deblock (dichloroacetic acid [a 15% solution in methylene chloride was special ordered from Glen Research] diluted to 3% in methylene chloride) to remove the DMT as described above. Washes were performed until the orange color generated by the free trityl groups was completely gone, with a maximum incubation time of 1 minute for all 3 washes.

After the final wash, the reactions were neutralized with three 1 ml washes of a 1:1 mixture of acetonitrile:pyridine, stored over calcium hydride. This was followed by 8, 2 ml washed with acetonitrile stored over calcium hydride. 1.5 ml of the appropriate phosphoramidite solution (either 50-100 mM of the positively charged or the neutral phosphoramidite in acetonitrile, stored over calcium hydride) and 1 ml of activator (0.25M 5-ethylthio-1H-tetrazole [Glen Research, Cat. #30-3140) in anhydrous acetonitrile over activated Molecular Sieves) was drawn up into the syringe. The needle was sealed using a silicone stopper (Aldrich, Cat. # Z16608-1) and rocked gently, by hand for 20 minutes at room temperature.

After the 20 minute incubation, the solution was ejected and six 1 ml washes with acetonitrile stored over calcium hydride were done as described above. Two ml of oxidizer (0.02M iodine in tetrahydrofuran/pyridine/water [Glen Research, Cat. #40-4330]) was drawn into the syringe, the needle was again sealed with a silicone stopper and the reaction was rocked gently at room temperature for 3 minutes. This was followed by 4, 1 ml acetonitrile (stored over calcium hydride) washes and 2, 1 ml acetonitrile:pyridine (1:1 mixture, stored over calcium hydride) washes. 1 ml of Cap B solution (10% n-methylimidazole in a solution of 8:1 tetrahydrofuran and pyrimidine [PE Biosystems]) and 1 ml of Cap A (THF/Acetic Anhydride, 9:1, PE Biosystems) were drawn into the syringe, the needle was capped and the reaction was rocked gently for 3 minutes at room temperature. This was followed by six 1 ml washes with acetonitrile:pyridine (1:1 mixture, stored over calcium hydride) and five 1 ml washes with methylene chloride stored over activated, Molecular Sieves.

For subsequent manual couplings, the above procedure can be repeated, starting with the deblock washes. For subsequent automated couplings, the support can be transferred to a synthesis column and attach to synthesizer. If the reaction is complete, the 5' dimethoxy trityl can be removed by washing with deblock, neutralizing with 3 three 1 ml acetonitrile: pyrimidine washes, and eight 2 ml acetonitrile washes, as described above.

Deprotection Protocol:

The dried support (CPG) carrying the newly modified oligonucleotide was transferred to a 4 ml glass vial (Wheaton, 224801) with a TEFLON-lined cap (Wheaton 240408). 1 ml of concentrated ammonium hydroxide (EM Sciences AX 1303-13) was added and the reaction was incubated overnight at room temperature. The mixture was then Filter through a 0.2 μm TEFLON Acrodisc filter (Gelman, 4423T) using a 1 ml disposable syringe (B-D, 309602), and finally dried to completion in a speedvac.

Example 5

Synthesis of Positively Charged Phosphoramidite

1) Preparation of mono-DMT Protected 4,4'-timethylene(bis (1-piperidine ethanol)):

10 grams (33.4 mmol) of 4,4'-timethylene(bis-(1-piperidine ethanol)) [Aldrich, Cat. #12, 122-3] and 1.46 ml (8.4 mmol) of N—N-di-isopropylethylamine [Aldrich, Cat. #38, 764-9] were combined in a 250-ml round-bottom flask (such as ChemGlass, Cat. #CG-1506). A magnetic stir bar was added and stirring was initiated at medium speed. 2.84 grams (8.4 mmol) of 4,4'-dimethoxytrityl chloride (Aldrich, Cat. #10,001-3) was added as a solid, slowly (over the course of about 1 minute) with constant stirring. The flask was covered with a rubber septum and the reaction was incubated at room temperature with continued stirring, until complete, for about 1 hour. The reaction was monitored by thin layer chromatography (EM Science 60F254 silica plates from VWR, Cat. #5715-7) using standard methods known in the art until the starting material, 4,4'-dimethoxytrityl chloride, was no longer detected on the chromatography plate. The reaction products were then filtered and purified by column chromatography using a 4.5 by 25 cm glass chromatography column (with glass frit and TEFLON stopcock) and 70-230 mesh, 60 angstrom silica gel (Aldrich, Cat. #28, 862-4). The running solvent was a solution of 5% methanol, 5% triethylamine and 90% methylene chloride. Chromatography was performed by standard methods known in the art. The product was a yellow oil, with a yield of approximately 4.8 grams (95%) with an Rf value of 0.55 as determined by TLC. TLC was performed using EM Science 60F$_{254}$ silica plates (VWR, Cat. #5715-7), in a running buffer of 5% triethylamine/95% dioxane.

2) Preparation of Phosphoramidite:

1.3 grams (2.2 mmol) of mono-DMT protected 4,4'-timethylene(bis-(1-pipirdine ethanol)) synthesized in the above reaction was co-evaporated in a 250 ml round bottom flask, three times with 20 ml of acetonitrile. A Büchi Rotovapor with dry ice/alcohol condenser, (Büchi, model number R-114) was used for the evaporation, and the mixture was dried to completion for each co-evaporation.

The dry product was then dissolved in 12 ml of methylene chloride followed by an addition of 0.85 ml (2.7 mmol) of 2-cyanoethyl tetraisopropyl phosphorodiamidate (Aldrich, Cat. #30, 599-5). 122 mg (1.7 mmol/4 ml) of tetrazole dissolved in 3 ml dry acetonitrile was added with vigorous swirling, and the reaction vessel was secured in a cork ring, taped to a vortexer and vortexed at medium speed, at room temperature, for 1.5 hours. The reaction was monitored by TLC and was complete when mono-DMT protected 4,4'-timethylene(bis(1-piperidine ethanol)) was no longer visible by TLC.

25 ml of methylene chloride were added to increase the volume, and the entire reaction was transferred to a 100 ml separatory funnel. An equal volume (approximately 40 ml) of a 5% sodium bicarbonate: 1% triethylamine solution was added, the mixture was shaken for 15 seconds and allowed to equilibrate. The lower, organic phase was drained from the funnel and retained. The upper aqueous phase was discarded, the organic phase was transferred back to the separatory funnel and the wash was repeated for a total of three sodium bicarbonate/triethylamine washes.

The organic phase was transferred to an Erlenmeyer flask and solid magnesium sulfate (approximately 20 g) was slowly added, with swirling, until no clumping of the solids was detected. The magnesium sulfate was filtered via a Büchner filter funnel with ground glass adaptor (Chemglass, Cat. # CG-1406) and the solution was concentrated and co-evaporated twice with 20 ml of acetonitrile on a Büchi Rotovapor in a tared, round-bottom flask. The amount of dry product was determined by mass, and then re-dissolved in acetonitrile to a final concentration of approximately 150-200 mg/ml. Several granules of calcium hydride were added. The dissolved product was then dispensed (2 ml/bottle) into amber glass vials (Wheaton, Cat. #224754) and dried, first via a water aspirator until the product appears as an extremely viscous oil, and then overnight under vacuum in a glass dessicator (VWR) containing phosphorous pentoxide (Aldrich, Cat. #29822-0) and DRIERITE (VWR, Cat. #22891-040). The yield was approximately 1.6 grams (92.1%) with an Rf value of 0.7 as determined by TLC. TLC was performed using pre-run EM Science 60F$_{254}$ silica plates (VWR, Cat. #5715-7), in a running buffer of 5% triethylamine/95% dioxane.

Example 6

Synthesis of Neutral Phosphoramidite

1) Synthesis of mono-DMT Protected N-methyldiethanolamine:

8.3 grams (70.0 mmol) of N-methyldiethanolamine, 2.2 ml (12.6 mmol) of di-isopropyl ethylamine and 100 ml of acetonitrile were combined in a 250-ml round-bottom flask (such as ChemGlass, Cat. # CG-1506). A magnetic stir bar was added and stirring was initiated at medium speed. 4 grams (11.8 mmol) 4,4'-dimethoxytrityl chloride (Aldrich, Cat.# 10,001-3) was added as a solid, slowly (over the course of about 1 minute) with constant stirring. The flask was covered and the reaction was incubated at room temperature with continued stirring, until complete, for about 1 hour. The reaction was monitored by thin layer chromatography (EM Science 60F$_{254}$ silica plates from VWR, Cat.# 5715-7) using standard methods known in the art. The reaction is complete when the starting material, N-methyldiethanolamine is no longer detected on the chromatography plate.

After the 1 hour incubation, the reaction products were concentrated using the Büchi Rotovapor, and then dissolved in 50 ml of methylene chloride. The dissolved product was transferred to a 250 ml glass separatory funnel and washed 3 times with 50 ml of 5% sodium bicarbonate and once with saturated sodium chloride, as described above.

The reaction products were then filtered and purified by column chromatography using a 4.5×25 cm glass chromatography column (with glass frit and TEFLON stopcock) and 70-230 mesh, 60 angstrom silica gel (Aldrich, Cat.# 28, 862-4). The running solvent was a solution of 5% methanol, 5% triethylamine and 90% methylene chloride. Chromatography was performed by standard methods known in the art. The product was a yellow oil, with a yield of approximately 4.8 grams (95%), with an $R_f$ value of 0.55 as determined by TLC. TLC was performed using pre-run EM Science 60F$_{254}$ silica plates (VWR, Cat.# 5715-7), in a running buffer of 5% triethylamine/95% dioxane.

2) Preparation of Phosphoramidite:

1.3 grams (3.2 mmol) of mono-DMT protected N-methyldiethanolamine, synthesized in the above reaction, was co-evaporated in a 250 ml round bottom flask, three times with 20 ml of acetonitrile (ACN). A dry ice/alcohol, Büchi Rotovapor, (Büchi, model number R-114) was used for the evaporation, and the mixture was dried to completion for each co-evaporation.

The dry product was then dissolved in 12.6 ml of methylene chloride followed by and addition of 1.2 ml (3.8 mmol) of 2-cyanoethyl tetraisopropyl phosphorodiamitide (Aldrich, Cat.# 30, 599-5). 173 mg (2.5 mmol/4 ml) of tetrazole/acetonitrile was added with vigorous swirling, and the reaction vessel was secured in a cork ring, taped to a vortex and vortexed at medium speed, room temperature, for 3 hours. 25 ml of methylene chloride were added to increase the volume, and the entire reaction was transferred to a 100 ml separatory funnel. An equal volume (approximately 40 ml) of a 5% sodium bicarbonate: 1% triethylamine solution was added, the mixture was shaken for 3-5 seconds and allowed to equilibrate, and the lower, organic phase was drained from the funnel and saved. The upper aqueous phase was discarded, the organic phase was transferred back to the separatory funnel and the wash was repeated, for a total of three sodium bicarbonate/triethylamine washes. The organic phase was transferred to an Erlenmeyer flask and solid magnesium sulfate (approximately 20 g) was slowly added, with swirling, until no clumping of the solids was detected. The magnesium sulfate was filtered out via a Büchner filter funnel with ground glass adaptor (Chemglass, Cat.# CG-1406), and the solution was concentrated and co-evaporated twice with 20 ml of acetonitrile in a Büchi Rotovapor in a tared, round-bottom flask. The amount of dry product was determined by mass, and as then re-dissolved in acetonitrile (and several granules of calcium hydride) to a final concentration of approximately 150-200 mg/ml. The dissolved product was then aliquoted (2 ml/bottle) into amber glass bottles (Wheaton) and dried, first via a water aspirator until the product appears as an extremely viscous oil, then overnight under vacuum in a glass dessicator (VWR) containing phosphorous pentoxide (Aldrich) and DRIERITE (VWR). The yield was approximately 1.9 grams (97.0%) with an Rf value of 0.8 as determined by TLC. TLC was performed using pre-run EM Science 60F$_{254}$ silica plates (VWR, Cat.# 5715-7), in a running buffer of 5% triethylamine/95% dioxane.

Example 7

Synthesis of the 1,6 Hexanediol H-Phosphonate

1) Synthesis of the DMT Protected 1,6-Hexanediol

Three grams (25 mmol) of 1,6-hexanediol (Aldrich, Cat.24,011-7) was dissolved in 120 mL of anhydrous tetrahydrofuran (THF) (Aldrich, Cat.# 18, 656-2). 1.5 mL (1.1 g, 88 mmol) of di-isopropylethylamine (Aldrich, Cat.# 38, 764-9) were added, and the resulting mixture (protected from moisture) was stirred at room temperature for 15 minutes. Three grams (9 mmol) of Dimethoxytrityl Chloride (DMTCl) was then added, and the solution was incubated, with stirring for two hours at room temperature. The resulting mixture was concentrated under reduced pressure via a Büchi Rotovapor (Büchi, model R-114), and the concentrated material was filtered and purified via column chromatography using silica gel column (70-230 mesh)/Hexane:Ethyl Acetate 1:1 by standard methods known in the art. Fractions containing isolated material (as determined by TLC; $R_f$=0.3) were combined and concentrated. The yield was 77% (2.9 g; 7 mmol).

2) Synthesis of the DMT-1,6-Hexanediol H-phosphonate

All reactions described below were performed under nitrogen in a system protected from moisture.

a) Synthesis of the Phosphorus Triimidazolide (PIm$_3$)

4.3 mL (5.9 g; 43 mmol) of Phosphorus trichloride (PCl$_3$, Aldrich, Cat.#31,011-5) was dissolved in 100 mL of anhydrous THF at 0° C. with gentle stirring. The temperature was held at 0° C., and stirring was continued while, over a period of 10 minutes, 18.8 mL (18 g, 129 mmol) of Trimethylsilyl-chloride (Me$_3$Si—Cl, Aldrich, Cat.#C7,285-4) dissolved in 40 mL of anhydrous THF was added to the reaction. After the addition of Me$_3$Si—Cl, the reaction mixture was incubated at 0° C. for 30 minutes with continued stirring, and then at room temperature for 30 minutes with continued stirring. Finally, the reaction mixture was concentrated under reduced pressure, protected from moisture, to 75% of its original volume.

b) Synthesis of H-Phosphonate 5.9 g (14 mmol) of the DMT-protected 1,6-hexanediol synthesized above was dissolved in 10 mL of anhydrous acetonitrile, and was then added slowly (over a period of about 5 minutes, with constant stirring) at room temperature, to the phosphorus triimidazolide (PIm$_3$) solution. The reaction was incubated at room temperature with stirring for 4 hours, and then transferred to a separatory funnel containing 100 ml of water, 50 g of ice, 20 ml of Triethylamine and 50 ml of methylene chloride. The organic and aqueous phases were allowed to separate, and the organic (lower) fraction was isolated. The extraction was repeated until no DMT-containing material was present in the organic fraction as determined by TLC, described previously. Combined organic fractions were dried over magnesium sulfate for 1 hr, followed by concentration under reduced pressure. The concentrated product was purified by column chromatography using Silica gel 70-230 mesh, methylene chloride/methanol 10%/Triethylamine 5% ($R_f$=0.5).

Product containing fractions were combined and concentrated. Yield: 5.8 g (61%). The final concentrated product was then co-evaporated 5 times with 50 ml of anhydrous Acetonitrile, dried under high vacuum for 18 hours and dissolved in 18 mL of Pyridine/Acetonitrile 1:1. Activated Molecular sieves (3 angstrom) were added.

Example 8

Manual Introduction of Modifications into CRE Probes Using H-phosphonate Chemistry A 2.5 ml gas-tight Hamilton syringe (VWR, Cat.#90168) was loaded (as detailed in Example 4) with 1 μmol CPG support (DMT on) coupled with a DNA CRE probe (for example, SEQ ID NO:55).

To remove the DMT, the CPG/oligonucleotide complex was washed twice (as described in Example 4) with 1 ml of methylene dichloride, then washed for 1 minute with 5 ml of 3% dichloroacetic acid in methylene dichloride. The reaction was then washed 10 times with 1 ml of anhydrous acetonitrile/pyridine 1:1. After the final wash, one of 5 different H-phosphonate moieties (the 1,6 hexanediol H-phosphonate synthesized in Example 7; dA-H-Phosphonate, dC-H-Phosphonate, dG-H-Phosphonate, or dT-H-Phosphonate [Glen Research, Cat.# 10-1200-05, 10-1210-05, 10-1220-05, 10-1230-05]) was added as follows. 1 ml of H-phosphonate solution (concentration: 50-150 μmol/mL) and 1 mL of the trimethylacetyl chloride solution in anhydrous acetonitrile/pyridine 1:1 (concentration: 100-250 μmol/mL) were drawn into the syringe, the needle was sealed and the reaction was incubated at room temperature with gentle shaking for 5-10 minutes. The syringe contents were expelled, and 6, 1 ml acetonitrile/pyridine 1:1 washes were done. After the last wash, 0.1-0.2 g of a primary or secondary amine (for example N,N-dimethylethylenediamine, Aldrich, Cat.#D15, 780-5) in 1 mL of anhydrous pyridine, followed by 0.5 mL of anhydrous carbon tetrachloride were drawn into the syringe and incubated at room temperature, with gentle shaking for 5-15 minutes. The syringe contents were expelled, and six 1 ml anhydrous acetonitrile/pyridine 1:1 washes were done. This was followed by six 1 ml methylene chloride washes; a 1 minute wash with 5 ml 3% dichloroacetic acid/methylene dichloride; ten 1 ml washes with anhydrous acetonitrile/pyridine 1:1 and six 1 ml washes with methylene chloride.

The dried support (CPG) was transferred to a 4 ml glass vial (Wheaton, 224801) with a TEFLON-lined cap (Wheaton 240408). 1 ml of concentrated ammonium hydroxide (EM Sciences AX 1303-13) was added and the reaction was incubated for 12 hours at 55° C. After the cleavage and deprotection was completed, the product containing ammonia solution was concentrated under reduced pressure and subjected to ion exchange HPLC or reverse phase HPLC purification.

For all HPLC purifications, the Hitachi HPLC (Interface model# D-7000; pump model# 7100; diode array detector model# L-7455) system, and standard methods known in the art were used. The specific conditions used for the Reverse Phase HPLC purification were: C-18 Dionex analytical column (4.6×250 mm) with a flow rate of 1 ml/min, starting with 100% buffer A (0.1M TEAA) and 0% buffer B (acetonitrile), and transitioning to buffer B at a rate of 1% buffer B per minute. Fractions were collected and analyzed via mass spectrometry by methods known in the art, to identify the complete product.

The specific conditions used for the ion exchange HPLC purification were: Amersham Pharmacia Biotech HR 10/10 15Q IE column (10×100 mm) with a flow rate of 5 ml/min. Buffer A (20 mM sodium perchlorate, 20 mM sodium acetate, 10% acetonitrile, pH 7.35) and Buffer B (600 mM sodium perchlorate, 600 mM sodium acetate, 10% acetonitrile, pH 7.35) were used in a gradient beginning and ending at 5% A/95% B, with a gradient increase of approximately 65% B per minute. Fractions were collected and analyzed by mass spectrometry by methods known in the art, to identify the desired product.

Example 9

Effect of Tag Modifications on the Invader Assay Reaction

In this example, oligonucleotide probes containing positively charged tags at their 5' ends were tested in INVADER assay reactions, and the reaction turnover rates using two, differently modified probe oligonucleotides were compared. Here, turnover rate is defined as the number of cleavage events per target per unit time. The turnover rates were determined as described in (Lyamichev, et al., Biochemistry 39:9523 [2000]).

The first oligonucleotide probe, 5'-Cy3-AminoT-AminoT-ACG CCA CCA GCT-3' (SEQ ID NO:56, termed 203-85-5), utilized AminoT modifications such as those described in Example 2.

The second oligonucleotide probe, 5'-V—(Hex)-Cy3-CGC TGT CTC GCT-3' (SEQ ID NO:57, termed 490-52), was synthesized using the H-phosphonate modification V-(Hex), depicted in FIG. 11. The INVADER-directed cleavage of probes 203-85-5 and 490-52 was designed to release net positively charged Cy3-labeled products 5'-Cy3-AminoT-AminoT-3' and 5'-V—(Hex)-C-3', respectively. The first product is generated by enzymatic cleavage after AminoT, whereas the second product is produced by the cleavage after a natural base C.

The INVADER oligonucleotide 5'-GCTCAAGGCACTCTTGCC C-3' (SEQ ID NO:58, termed 203-85-4) and the target oligonucleotide 5'-ATG ACT GAA TAT AAA CTT GTG GTA GTT GGA GCT GGT GGC GTA GGC AAG AGT GCC TTG ACG ATA-3' (SEQ ID NO:59, termed 203-85-3) used with the probe 203-85-5 were synthesized using phosphoramidite reagents obtained from Glen Research and standard phosphoramidite chemistries known in the art. The underlined nucleotides denote 2'-O-methyl modifications. The INVADER and target oligonucleotides used with the probe 490-52 were combined into the single molecule 5'-biotin-TTT TTT TTT AAT TAG GCT CTG GAA AGA CGC TCG TGA AAC GAG CGT-3' (SEQ ID NO:60, termed IT5). All oligonucleotides were gel purified and quantitated as described (Lyamichev, et al., supra).

The INVADER assay reactions utilizing the AminoT-modified probe 203-85-5 were performed as follows: 10 μl reactions were prepared and contained (final concentrations): 2 μM amino modified probe (203-85-5), 1 μM INVADER oligonucleotide 203-85-4 (SEQ ID NO: 58), 1 nM target oligonucleotide 203-85-3 (SEQ ID NO:59), 32 nM AfuFEN1 CLEAVASE enzyme, 10 mM MOPS, pH 7.5, and 4 mM MgCl$_2$.

The INVADER reactions utilizing probe 490-52 (2 μM) were prepared as above, except 1 nM of the IT5 oligonucleotide (SEQ ID NO:60) was used, and served as both the INVADER oligonucleotide and the target oligonucleotide.

The reactions were assembled on ice in 200 μl thin wall PCR tubes (Dot Scientific, Cat.#620-PCR), overlaid with 10 μl of Chill-out liquid wax (MJ Research) and transferred to a Mastercycler heating block (Eppendorf, Cat.# 5331 000.045). The reactions were incubated for 60 minutes at 55.3, 57.7, 60.5, 63.4, 66.2, and 68.7° C. using a temperature gradient of 62±10° C. (controlled by the heating block). The reactions were stopped after 1 hour with the addition of 10 μL of 95% formamide containing 20 mM EDTA and 0.02% methyl violet.

One microliter aliquots of each reaction were loaded onto each of two 200×200×1 mm slabs of 15% denaturing polyacrylamide gel (crosslinked 19:1) with 7 M urea in a buffer containing 45 mM Tris borate, pH 8.3 and 1 mM EDTA. An electric field of 20 watts was applied for 30 minutes with the positive electrode connected either to the top buffer reservoir (reverse orientation) or bottom reservoir (normal orientation). The net positively charged products generated in the course of the INVADER reactions were detected by gel electrophoresis in the reverse orientation and the uncleaved probes of the same samples were analyzed by separation in the normal orientation. The intensities of bands corresponding to the products and uncleaved probes were measured using FMBIO-100 fluorescence imager (Hitachi, Alameda, Calif.) equipped with 532-nm laser and 585-nm filter at 10% sensitivity level.

Figure 22:
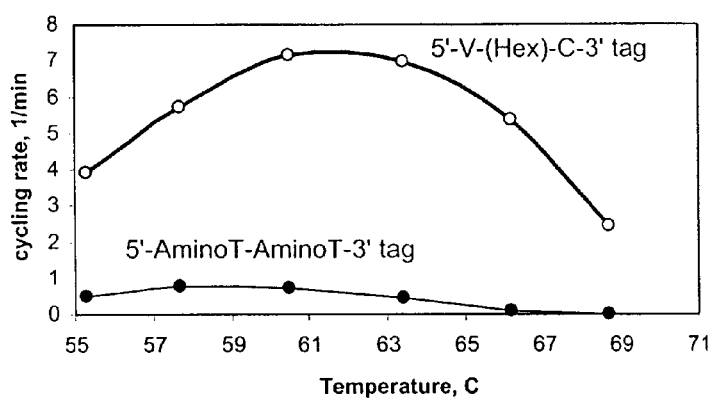
FIG. 22 shows a graph comparing rates of cleavage of charge-modified probes.

The measured turnover rates for probes 203-85-5 (SEQ ID NO:56) and 490-52, (SEQ ID NO:57) as a function of temperature are shown in FIG. 22. The probe 490-52 which was synthesized using H-phosphonate chemistry to introduce the modification V-(Hex), has approximately 10-fold greater turnover rate than the AminoT modified probe 203-85-5.

Example 10

Detection of Specific Cleavage Products by Charge Reversal

This example demonstrates that a CLEAVASE enzyme that recognizes cleavage structures containing RNA targets (CLEAVASE TthAKK) also recognizes and cleaves structures containing RNA targets and the above-described positively charged probe oligonucleotides. In this example, 5 different, modified probe oligonucleotides were used in an INVADER reaction to detect human MCP1 in vitro transcripts. Each probe oligonucleotide was designed to release a labeled product with a net positive charge such that the cleavage products could be detected using charge reversal methods.

Figure 23:
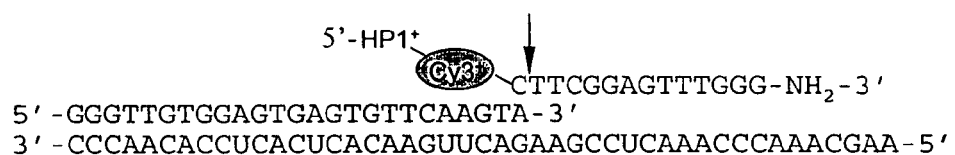
FIG. 23A shows a schematic diagram of an H-phosphonate (HP)-charge modified probe in an invasive cleavage.
FIG. 23B diagrams the structures of the charge-modified nucleoside (dN) and hexanol (HEX) tags.
Figure 23:
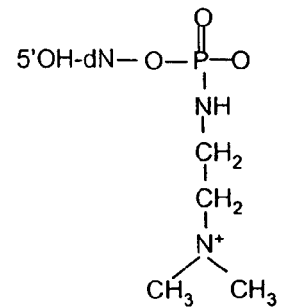
Figure 23:
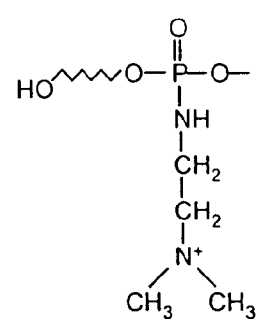

The five different, 5'-end modified, Cy3-labeled probe oligonucleotides tested were: 5'-V—(HEX)—Cy3-CTTCG-GAGTTTGGG-NH$_2$-3' (SEQ ID NO:61; termed "oligo P1"), 5'-V-(dA)-Cy3-CTTCGGAGTTTGGG-NH$_2$-3' (SEQ ID NO:62; termed "oligo P2"), 5'-V-(dC)—Cy3-CTTCG-GAGTTTGGG-NH$_2$-3' (SEQ ID NO:63; termed "oligo P3"), 5'-V-(dG)-Cy3-CTTCGGAGTTTGGG-NH$_2$-3' (SEQ ID NO:64; termed "oligo P4"), and 5'-V-(dT)-Cy3-CTTCG-GAGTTTGGG-NH$_2$-3' (SEQ ID NO:65; termed "oligo P5") (FIG. 23). The 5' modifications were synthesized as described previously, and all 5 of the above oligonucleotides and the INVADER oligonucleotide, Inv1 5'-GGGTTGTGGAGT-GAGTGTTCAAGTA-3'(SEQ ID NO:66) were chemically synthesized on a DNA synthesizer (ABI 391) using standard phosphoramidite chemistries and reagents obtained from Glen Research (Sterling, Va.).

All probe oligonucleotides were purified by Anion exchange HPLC. There was one major and one or more minor peaks observed with this purification method. The material from the major (first) peak was used in all experiments described below.

In vitro transcripts were synthesized as follows. The human Ubiquitin cDNA was isolated from a first-strand human liver cDNA library (Clontech Cat #7407-1) by PCR using a universal 5' primer (API, 5' CCATCCTAATAC-GACTCACTATAGGGC-3', SEQ ID NO:67) provided with the library and a Ubiquitin-specific 3' primer (5'-CTCATA-CAGTTACTTGTCTTC-3', SEQ ID NO:68). PCR reactions were performed with an error-correcting polymerase mixture from Clontech (Cat #8417-1) according to manufacturer's instructions. The expected size of the PCR products was 500 bases. PCR products were gel purified on 1% agarose gel run in 0.5×TBE. The gel was Stained in 100 g/ml ethidium bromide, visualized under UV light, the appropriately sized band was excised and the DNA recovered with a QIAquick Gel Extraction Kit (Qiagen Cat #28706). The gel-purified fragment was then cloned into the pCR2.1—TOPO cloning vector (Invitrogen, Cat. # K4500-01) by methods known in the art. Positive clones were selected and insert identity was confirmed by DNA sequencing. The positive plasmids were transformed into TOP10 cells (Invitrogen). Cells were grown and plasmid isolated by methods well known in the art of molecular biology. The same 5' and 3' primers used above were then used in PCR reactions to generate templates for use in in vitro transcription reactions. In vitro transcriptions were done performed using the Ambion T7 MEGAshortscript RNA Transcription Kit (Ambion, Cat.# 1354) according to the manufacturer's instructions. The resulting human ubiquitin transcript is SEQ ID NO:69. Note that the use of the AP15' primer includes the T7 RNA polymerase promoter, which is necessary for the generation of in vitro transcripts. All transcripts used in the following reactions contained tRNA (Sigma) at 20 ng/μl as carrier.

HMCP1 in vitro transcripts were synthesized as follows. The human Monocyte Chemoattractant Protein-I (hMCP-1) cDNA was obtained from 10 ug/ml Con-A (concanavalin-A) and PHA (phytohemagglutinin) stimulated human PMBC's (Peripheral Blood Mononuclear Cells) total RNA. Total RNA was isolated from 1×10$^7$ cells with TRIzol®Reagent (Gibco BRL Cat #15596) according to the manufacturing protocol. 500 ng of total RNA was used for reverse transcription using the GeneAmp RNA PCR kit (Perkin Elmer cat #N808-0017) for the generation of the cDNA. This RT-PCR was performed using a gene specific 5' primer that also contained the T7 RNA polymerase promoter site (5'-GGAATACGACTCACTAT-AGGGAAAGTCTCTGCCGCCCTTCTGTGCCTGCTGC-3', SEQ ID NO:70) and a 3' hMCP-specific primer (5'-AAT-AGTTACAAAATATTCATTTCCACAATAA-3', SEQ ID NO:71). The 665 base fragment was re-amplified using the same PCR primers and Taq DNA Polymerase (Perkin Elmer Cat. #N808-0152). The fragment was column purified using the Wizard® PCR Preps DNA Purification System (Promega Cat # A7170) and quantitated by O.D.$_{260}$ measurement. In vitro transcription was performed using 600 ng of the purified PCR product in the Ambion T7 MEGAshortscript RNA Transcription Kit (Ambion Cat #1354) according to the manufacturer's protocol. The hMCP in vitro transcript generated (SEQ ID NO:72) was 647 nt long.

The solution of the in vitro transcript was mixed with an equal volume of loading dye (95% Formamide, 10 mM EDTA, Methyl violet dye), heat denatured at 90° C. for 3 minutes and then loaded on a 6% denaturing (19:1 crosslinked) with 7 M urea acrylamide gel run in 0.5×TBE. After the electrophoresis, one of the glass plates was removed and the gel was covered with plastic wrap. The gel then was placed wrap-side-down on the TLC (DC Fertigplatten Kieselgel 40 F$_{254}$ Merck, Art 5634) plate and the other glass plate was removed. The RNA bands were visualized in the dark room by shining a hand-held UV light source (254 nM; short wave) on the surface of the gel. The nucleic acid will appear as dark bands while the TLC plate will appear green. The bands corresponding to the RNA were excised with a razor blade and eluted in TE (10 mM Tris, 0.1 mM EDTA) containing 0.3 M sodium acetate at 37° C. for 4 hours. The in vitro transcript was ethanol precipitated at −20° C. over night (alternatively, precipitation at −70° C. for 1 hour is also sufficient) and pelleted at 14,000 rpm for 30 min at 4° C. The pelleted nucleic acid was then washed with 70% ethanol and spun again for 5 minutes. After the ethanol was discarded, the pelleted nucleic acid was dried under vacuum and resuspended in RNase-free $H_2O$ (USB Cat # US70783). The concentration of the in vitro transcript was determined by OD260. All dilutions of the in vitro transcript used in the reactions were prepared in 20 ng/µl of yeast tRNA (Sigma Cat # RS636).

Five sets of reactions were done, one for each different probe oligonucleotide. A negative (no-target) control containing 100 ng of yeast tRNA was performed for each reaction set. Each 10 µl reaction was prepared at room temperature as follows. Five different master mixes were prepared, one for each probe. Each mix comprised (final concentration): 10 mM MOPS, pH 7.5, 100 mM KCl, 0.05% Tween, and 0.05% Nonidet NP40, 12.5 mM $MgSO_4$, 5 pmoles of INVADER oligonucleotide (SEQ ID NO:66) and 20 ng of CLEAVASE TthAKK enzyme. Finally, 10 pmoles of one of the probes (SEQ ID NOS:61, 62, 63, 64 or 65) were added for a final volume of 10 µl per reaction/per master mix. The master mixes were vortexed briefly and 5 µl of each was transferred to the appropriate reaction vessel (200 µl thin wall PCR tubes, Dot Scientific, Cat. #620-PCR), followed by the addition of 5 µl (containing 0, 0.1, 1 or 10 fmoles) of human MCP1 in vitro transcript. 100 ng of yeast tRNA (Sigma) was used as a negative control. Samples were pipetted up and down 3 times to mix. The samples were then overlaid with 10 µl colored Chill out 14 liquid wax (MJ Research) to prevent evaporation and incubated at 63° C. for 60 min. Reactions were terminated by the addition of 50 µl of 95% formamide containing 10 mM EDTA.

Figure 24:
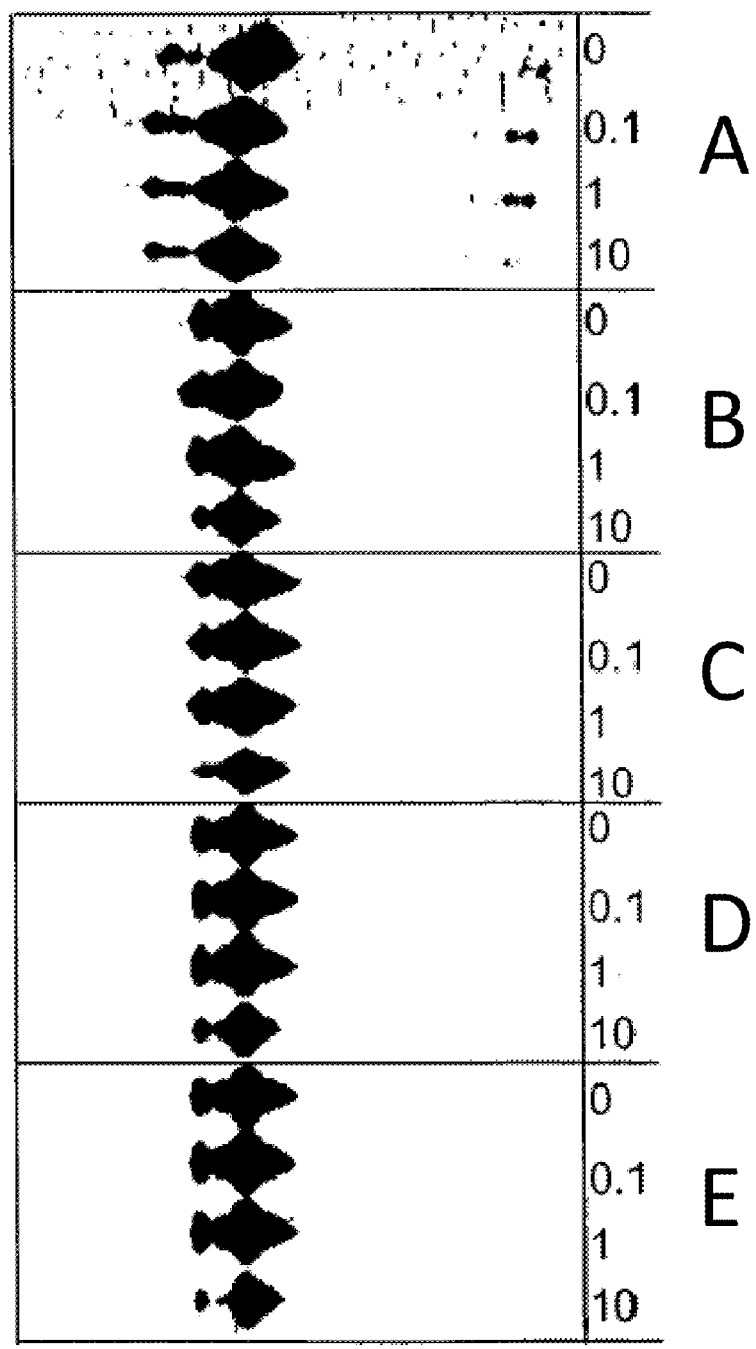
FIG. 24A is an image generated by a fluorescence imager showing the products of cleavage of 5 different charge-balanced probes, resolved by gel electrophoresis run in the standard direction.
FIG. 24B is an image generated by a fluorescence imager showing the products of cleavage of 5 different charge-balanced probes, resolved by gel electrophoresis run in the reverse direction.
Figure 24:
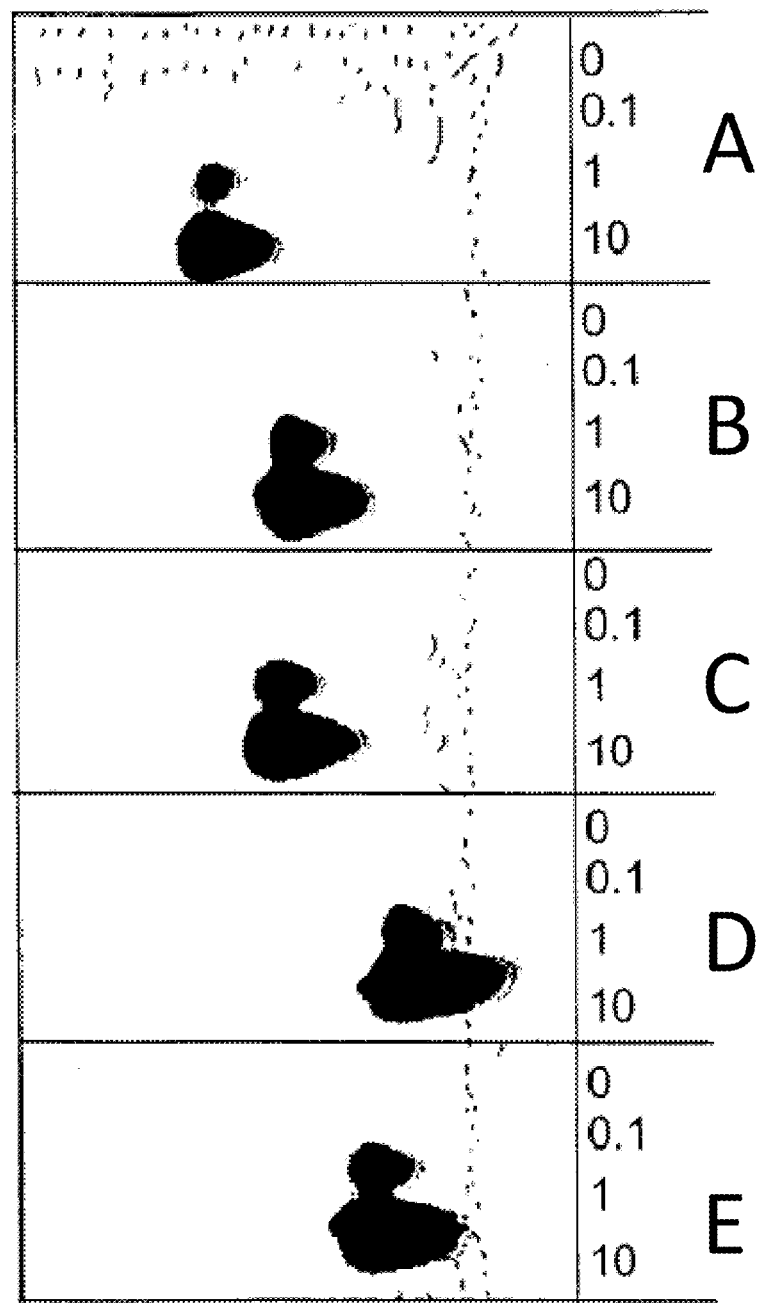

Samples were run on a 15% denaturing acrylamide gel (19:1 cross-linked) with 7 M urea, in a buffer containing 45 mM Tris-Borate (pH 8.3), 1 mM EDTA. The gel was pre-run, with the electrodes in the normal orientation prior to loading. The samples were heated to 90° C. for 1 minute immediately before loading, and 2 µl were loaded per well. An electric field of 20 watts was applied for 30 minutes with the electrodes in the normal orientation. The products were visualized following electrophoresis with a Hitachi FMBIO fluorescence imager with 585-nM filter at 20% sensitivity. The gel was then replaced on the running apparatus, and fresh buffer was added to the reservoirs. The electrodes were then placed in the reverse orientation, the gel was pre-run and loaded as above. The gel was run for 1 hour in the reverse orientation, and products were visualized as above. The resulting images are shown in FIG. 24. FIG. 24A shows the denaturing gel, which was run in the standard electrophoresis direction, and FIG. 24B shows the denaturing gel, which was run in the reverse direction. Probe V-(HEX) panel A; probe V-(dA) panel B; probe V-(dC) panel C; probe V-(dG) panel D; and probe V-(dT) panel E.

Example 11

Effects of a 5' Positive Charge on Cleavage Rate using CLEAVASE TthAKK Enzyme

The previous example demonstrated the ability of the CLEAVASE TthAKK enzyme to recognize and cleave a cleavage structure containing an RNA target and a positively charged probe oligonucleotide. This example tests the effect of the positively charged probes on cleavage rates.

All 5 of the positively charged probe oligonucleotides described in Example 10 were tested against a 5' fluorescein labeled "control" probe oligonucleotide (SEQ ID NO:73; 5' fluorescein phosphoramidite from Glen Research). Both the positively charged and the control probe were designed to detect the same sequence, so are identical in the analyte specific region. The difference between the fluorescein labeled and the CRE-V labeled probes include the charge difference at the 5' end, and the length of the cleaved products, or 5' flap. The 5' flap of the positively charged probes is 1 base, while the control probe yields a 3 base, 5' flap.

Reactions were performed as described in Example 10, using the hMCP1 in vitro transcripts as target. Only one target level was used to test the cleavage rate for each probe oligonucleotide. Each reaction received either 1 fmole of the hMCP1 in vitro transcript with 100 ng of yeast tRNA as carrier; 100 ng of yeast tRNA also served as a negative control. Reactions containing target were done in quadruplicate, while the tRNA control reactions were done singly.

Figure 25:
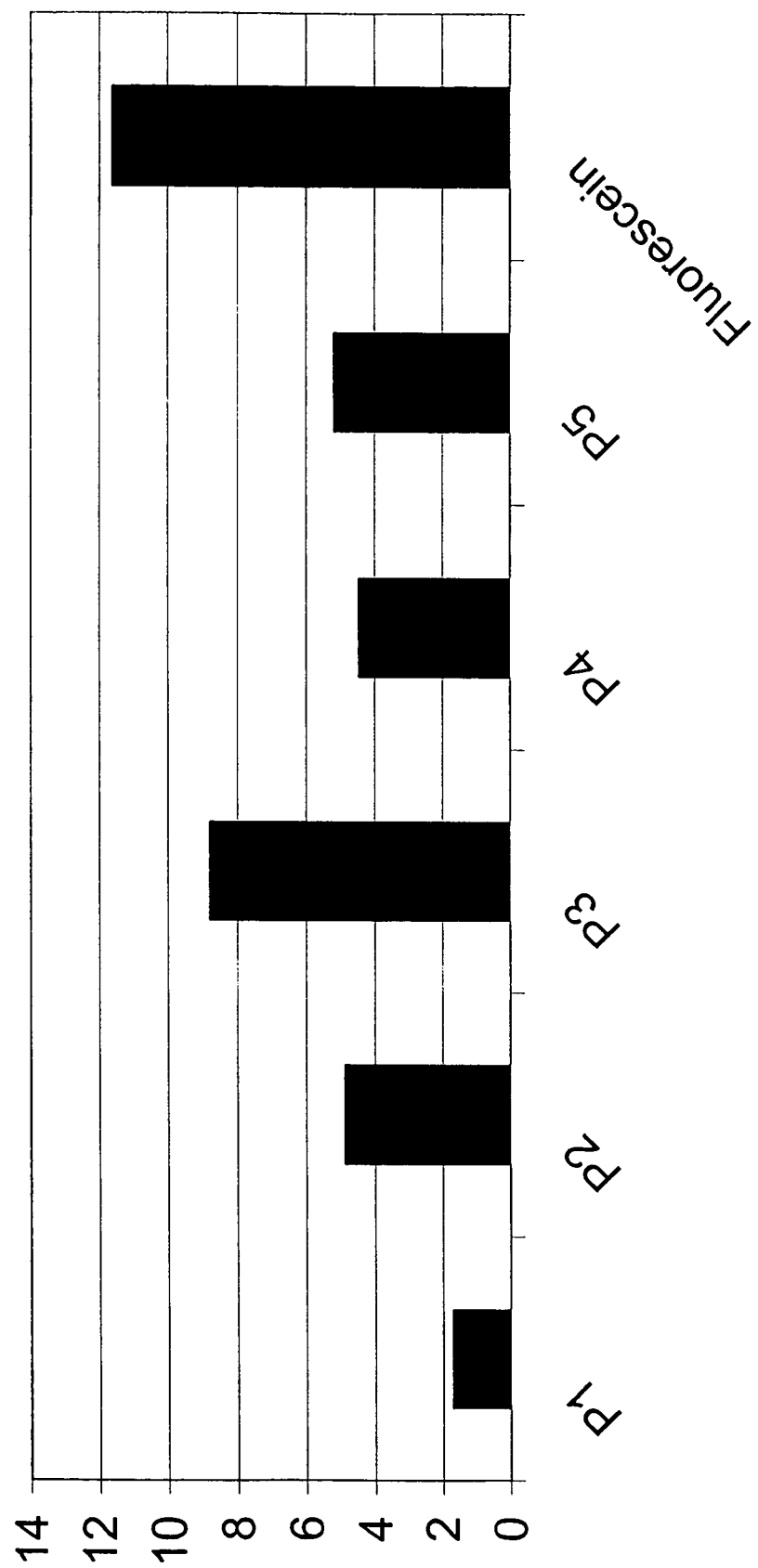
FIG. 25 shows a graph comparing the rates of cleavage of five charge balanced probes and one fluorescein-labeled control probe.

Turnover rates were determined as described in Lyamichev, et al., supra, and are shown graphically in FIG. 25. The rates ranged from 2- to 9 cleavage events/target/minute with P3 (SEQ ID NO:63) showing the highest rate among the positively charged probes. The average cleavage rate of the fluorescein labeled probe was 12 cleavage events/target/minute.

Example 12

Examination of the Rate of Background Accumulation with 5' Positively Charged Probe Oligonucleotides A key advantage to using positively charged probe oligonucleotides is the ability to completely separate signal (e.g., the single base flap carrying the positively charged signal molecule) from any other aberrant reaction products or uncleaved probes using simple, reverse polarity gel electrophoresis, as described and detailed in the above examples. This experiment confirms that background cleavage products (aberrant cleavage, or thermodegradation products) will not migrate in the reverse polarity gel, even if the reaction is incubated with large amounts of target for an extended period of time, allowing for greater certainty and simplicity in data interpretation.

Figure 26B:
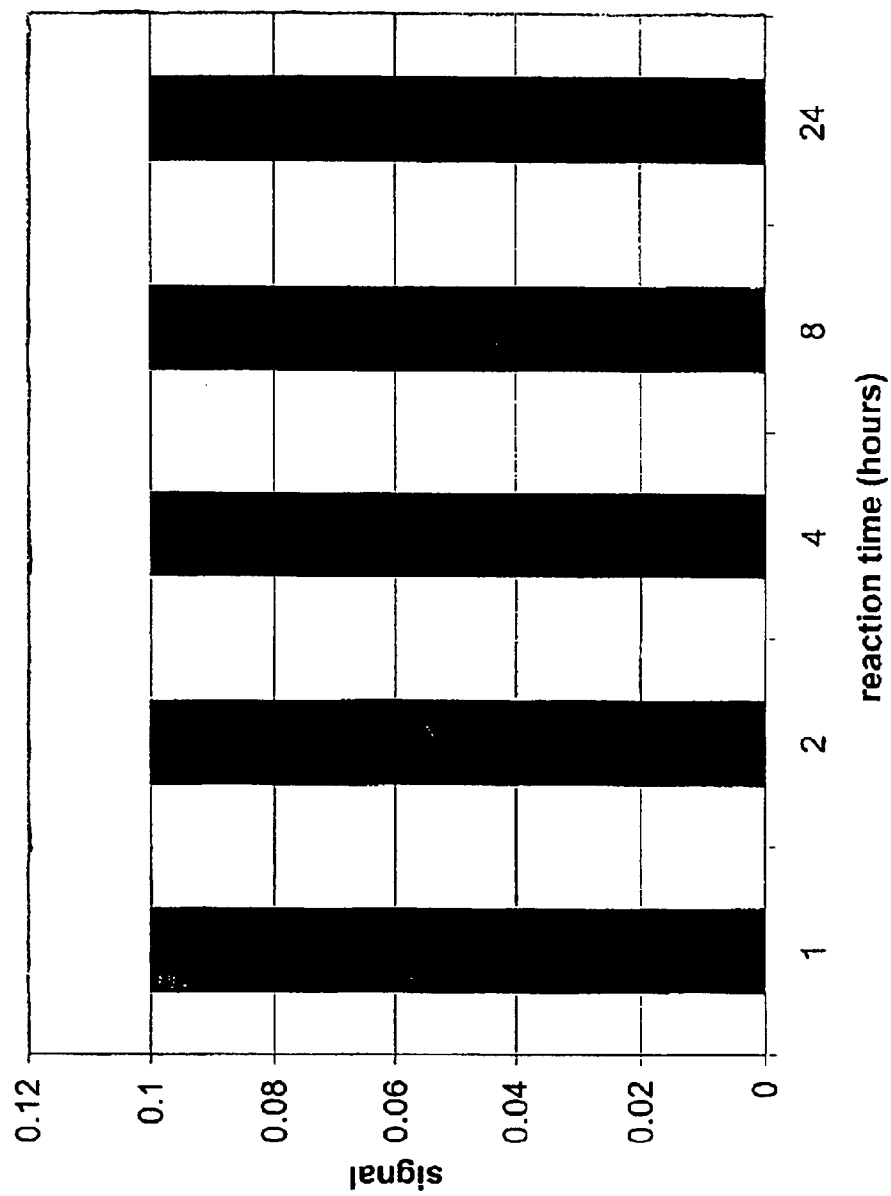
FIG. 26B shows a graph comparing the amounts of background signal detected in reactions performed for different times, ranging from one to twenty four hours.

The probe oligonucleotide used was P2 (described in Experimental Example 10, SEQ ID NO:62) and the INVADER oligonucleotide used was Inv1 (SEQ ID NO:66), also described in Example 10. The reaction conditions and gel based separation method were performed as described in 10. Reactions were performed with 0 (100 ng/5 µl of tRNA as a negative control; background estimate), 0.01, 0.1 and 1 fmole of hMCP1 in vitro transcript in a 10 µl reaction volume. Reactions were assembled as described in Example 10, and incubated for 1, 2, 4, 8 and 24 hours at 63° C. Reaction products were separated in normal or reverse polarity gels, as described in Example 10, and were analyzed based on the intensities from the Hitachi FMBIO scanner images and software, also described in Example 10. The results are shown graphically in FIG. 26. FIG. 26A represents the results of the denaturing gel, which was run in the standard electrophoresis direction, and FIG. 26B represents the results of the denaturing gel, which was run in the reverse direction.

Example 13

Detection of an RNA Target using Multiple, Positively Charged Probes

The previous experiments have demonstrated that the positively charged probes cleaved in a structure specific manner by the CLEAVASE enzyme, can be used to detect RNA targets, and, in certain detection platforms, can be analyzed such that the signal to background ratio is superior to "normal," negatively charged probe oligonucleotides.

The present experiment demonstrates that the cleavage products of different, 5' positively charged probes can be distinguished (based on the different mass to charge ratios), even when used in the same reaction.

The oligonucleotides used in this experiment, the reaction conditions, gel-based separation and the analysis were conducted as described in Example 10, except that 2 pmoles of each of 4 different probes [P1, P2, P4, and P5] were used, and the target levels were 0 (100 ng of tRNA only), 0.1, 1 and 10 fmoles of hMCP1 in vitro transcript. Two µl of each reaction was loaded on the gel in reverse polarity and separated as described.

Figure 27:
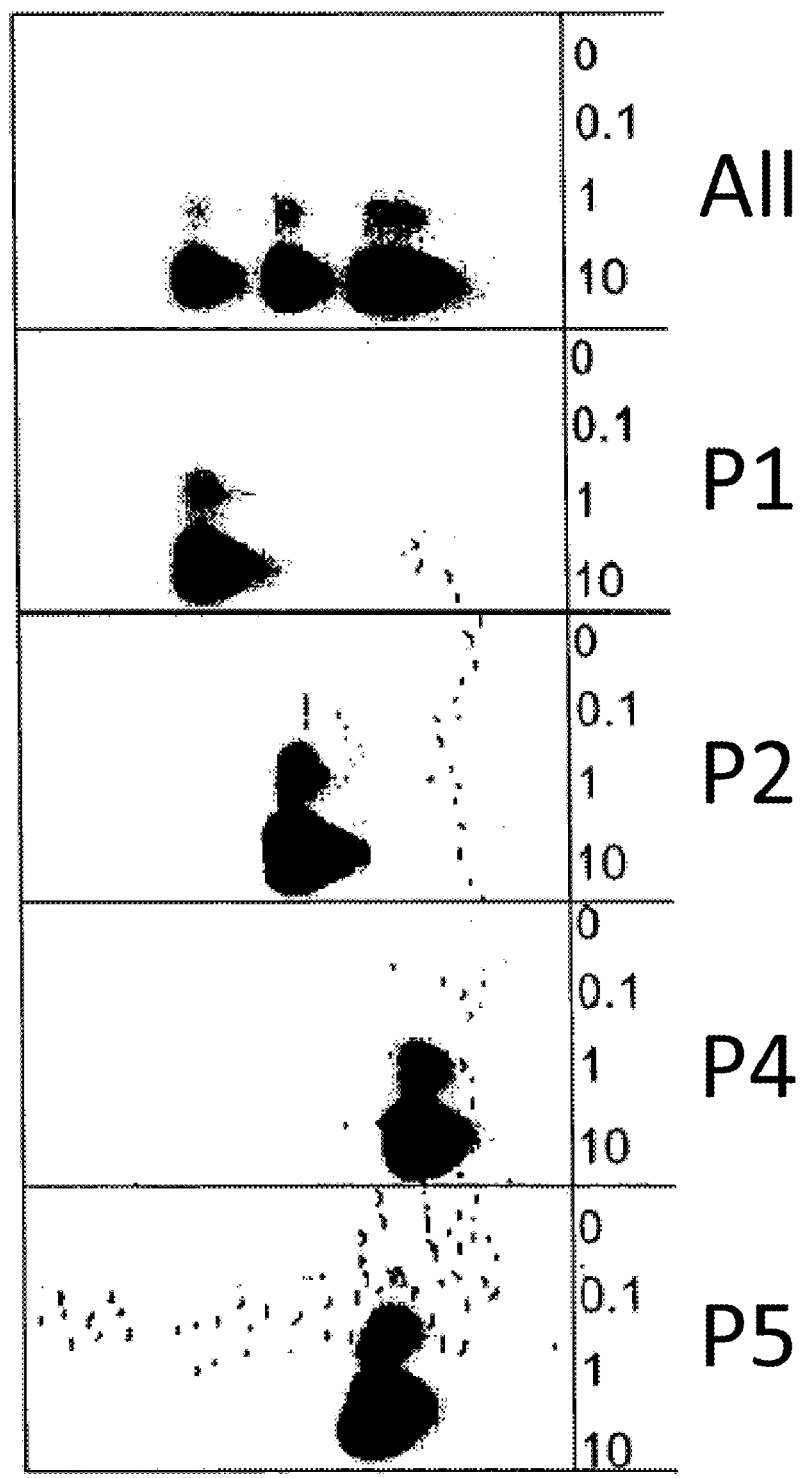
FIG. 27 is an image generated by a fluorescence imager showing the products of cleavage of four different charge-balanced probes, either alone or combined in a single lane, resolved by gel electrophoresis run in the reverse direction.

The resulting image is shown in FIG. 27. All cleavage products have a net positive charge. The mobility of the cleaved products from probe oligonucleotides P1, P2 and P4 were easily separated on the gel due to the differences in size (molecular weight) between them. In contrast, the cleaved products from the P5 probe oligonucleotide were barely distinguishable from the P4 products; the size and charge of these products are very similar. This demonstrates that a preferred, multiplex embodiment utilizes probes whose cleaved products can be easily distinguished in the detection system of choice.

Example 14

Figure 28A:
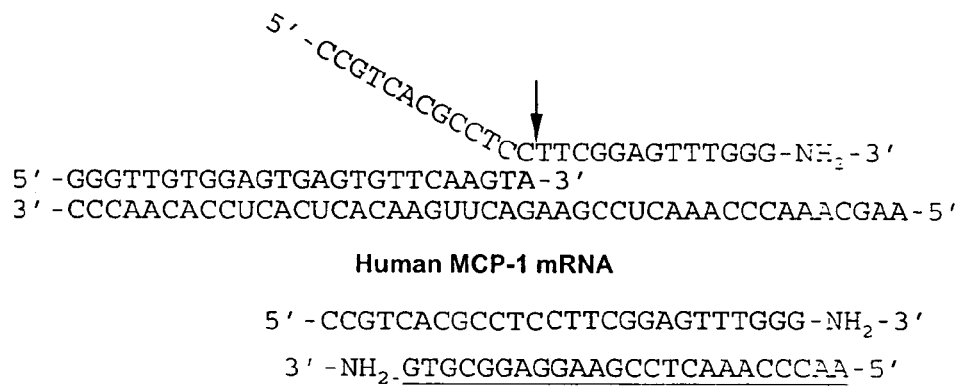
FIG. 28A shows a schematic diagram of oligonucleotides used for the detection of human MCP-1 RNA in a cascading cleavage reaction releasing a charge tag for detection.
Figure 28A:
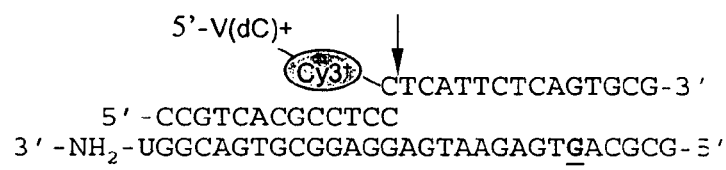

Human MCP1 and Human Ubiquitin In vitro Transcript Detection in a Cascade Reaction with Positively Charged Tags In this example, a two-step, sequential invasive cleavage reaction is used to detect both hMCP1 and hubiquitin in vitro transcripts, in a true, multiplex reaction (both targets are detected in the same reaction). The positively charged probes (termed reporter oligonucleotides, or reporter-labeled oligonucleotides in this example) are used in the second step of the sequential invasive cleavage reaction, as shown in FIGS. 28A and B. The added amplification provided by the cascading INVADER scheme yields greater sensitivity and lower limits of detection, important if target levels are limiting.

The mechanism of the sequential invasive cleavage reaction is as follows. The primary INVADER and probe oligonucleotides (those which hybridize to the target) are unlabeled and, when hybridized to the appropriate target sequence, form the overlapping structure recognized by the CLEAVASE enzyme (FIG. 28A). The enzyme cuts the structure and frees the 5' flap. The flap then acts as an INVADER oligo for the secondary reaction. The secondary reaction comprises 3 different oligonucleotides: 1) a flap-reporter bridging oligonucleotide that has adjacent regions complementary to both the 5' flap and the reporter-labeled, secondary probe oligonucleotide; 2) a reporter-labeled, secondary oligonucleotide, complementary to a portion of the bridging oligonucleotide, and 3) the INVADER oligonucleotide, which is the 5' flap from the primary reaction, and which is complementary to a portion of the bridging oligonucleotide. When the overlapping structure forms in the secondary reaction, the enzyme cleaves the 5' flap from the reporter-labeled oligonucleotide, generating detectable signal with a positive charge.

In the secondary reaction, the 5'-flaps of the uncleaved probe molecules can compete with the released 5'-flaps for hybridization to the flap-reporter bridging oligo, thus decreasing signal generation in the secondary reaction. To avoid this competition, the uncleaved probe is sequestered after the primary incubation by the addition of a complementary oligonucleotide called an "ARRESTOR oligonucleotide." The ARRESTOR oligonucleotide is fully complementary to the target-specific region of the probe, and partially extends into the 5'-flap region; thus, it does not interfere with the binding of the 5'-flap to the flap-reporter bridging oligonucleotide. ARRESTOR oligonucleotides thus promote more effective signal generation in the secondary reaction by preventing interactions between uncleaved probes and flap-reporter binding oligonucleotides. All of the bases of the ARRESTOR oligonucleotide are 2' O-methyl-modified, making the ARRESTOR oligonucleotide resistant to cleavage by the CLEAVASE enzyme.

Figure 28B:
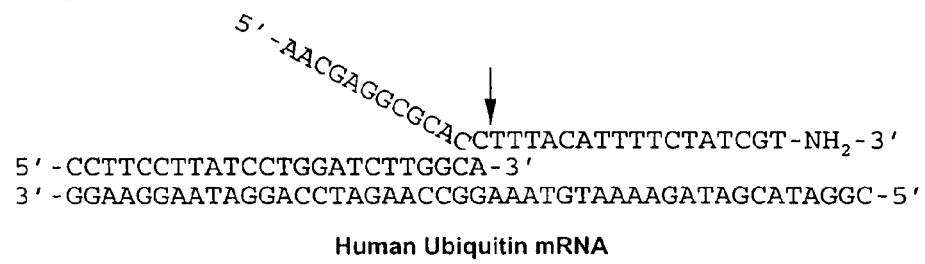
FIG. 28B shows a schematic diagram of oligonucleotides used for the detection of human Ubiquitin RNA in a cascading cleavage reaction releasing a charge tag for detection.
Figure 28B:
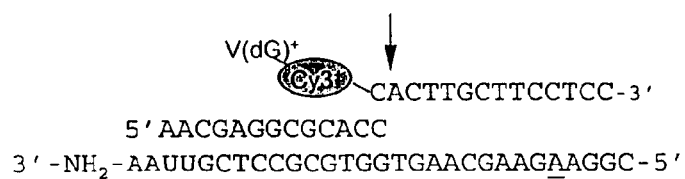

The tag used for the hMCP1 secondary, reporter probe oligonucleotide was 5' V(dC)-Cy3 (FIG. 28A), while the hubiquitin secondary, reporter probe oligonucleotide incorporated the 5' V(dG)-Cy3 tag (FIG. 28B). These tags were chosen since, as demonstrated in Example 10 and shown in FIG. 24 they are easily separated and identified due to the difference in mass-to-charge ratio between them. The oligonucleotides used for the detection of Human MCP1 in vitro transcripts were: the primary probe oligonucleotide 5'-CCGTCACGCCTCCTTCGGAGTTTGGG-NH$_2$-3' (SEQ ID NO:74), the primary INVADER oligonucleotide Inv1 (SEQ ID NO:66), the arrestor oligonucleotide 5' <u>AACCCAAACTCCGAAGGAGGCGTG</u>—NH$_2$-3' (SEQ ID NO:75), the flap-reporter bridging oligonucleotide 5' GCG-CAGTGAGAATGAGGAGGCGTGACGGT-NH$_2$-3' (SEQ ID NO:76), and the reporter-labeled secondary probe oligonucleotide 5'-V(dC)—Cy3 CTCATTCTCAGTGCG-3' (SEQ ID NO:77). The underlined bases denote 2'-O-methyl modifications. The oligonucleotides used for the detection of Human Ubiquitin in vitro transcripts were: the primary probe oligonucleotide 5'-AACGAGGCGCACCTTTACATTTTC-TATCGT-NH$_2$-3' (SEQ ID NO:78), the primary INVADER oligonucleotide 5'-CCTTCCTTATCCTGGATCTTGGCA-3' (SEQ ID NO: 79, the ARRESTOR oligonucleotide 5' <u>ACGATAGAAAATGTAAAGGTGCGC</u> NH$_2$-3' (SEQ ID NO:80), the flap-reporter bridging oligonucleotide 5'-CG-GAAGAAGCAAGTGGTGCGCCT <u>CGTTAA</u>—NH$_2$-3' (SEQ ID NO:81, and the secondary reporter-labeled probe oligonucleotide 5'-V(dG)-Cy3 CACTTGCTTCCTCC-3' (SEQ ID NO:82). Three control reaction sets were included in this experiment: 1) control reaction using a non-cascading reaction (basic INVADER, described in Example 10) to detect hMCP1 transcripts, using the 5' V(dC) probe (P3, SEQ ID NO:63) and the INVADER oligonucleotide Inv1 (SEQ ID NO:66) also used in Example 10; 2) a control reaction set designed to demonstrate the lack of cross reactivity between the oligonucleotides used for the detection of one target and the signal generating mechanism of the other target; and 3) a control set in which all primary and secondary components were present as for the multiplex reaction, but only one secondary reporter oligonucleotide was present: either for the detection of hMCP1 or hUbiquitin.

The primary reaction volumes were 10 μl and secondary reaction volumes were 15 μl. Each assay reaction comprised of 0, 1, 10 100 or 1000 amoles human ubiquitin and/or MCP1 in vitro transcript (SEQ ID NOS: 69 or 72, respectively) for the single and multiplex reactions, 10 pmoles each of the primary probe oligonucleotides (SEQ ID NOS:71 and 75) 5 pmoles of each primary INVADER (SEQ ID NO:66 and 79) oligonucleotides, and 20 ng of CLEAVASE TthAKK enzyme in a 10 μl solution of 10 mM MOPS, pH 7.5, 100 mM KCl., 0.05% Tween, 0.05% Nonidet NP40, 12.5 mM $MgSO_4$. Reactions were performed by dispensing 5 μl of the appropriate primary reaction mix (buffer, enzyme, $MgSO_4$, primary probe oligo and primary INVADER oligonucleotide) into the reaction vessel (low profile MJ Research, Inc. Cat.#MLL9601) and then adding 5 μl of target, or tRNA as the negative control. Samples were overlaid with colored Chill-out 14 liquid wax (MJ Research) to prevent evaporation and incubated at 60° C. for 60 minutes.

After the primary reactions were completed, 5 μl of the appropriate secondary reaction mixture (2.5 pmoles of appropriate flap-reporter bridging oligonucleotide [SEQ ID NOS: 76 and/or 81] 40 pmoles of ARRESTOR oligonucleotide [SEQ ID NOS:75 and/or 80] and 10 pmoles of each secondary reporter-labeled oligonucleotide [SEQ ID NOS: 77 and 82] such that the final concentration of the secondary reaction was 10 mM MOPS, pH 7.5, 0.05% Tween, 0.05% Nonidet NP40, 20 mM $MgSO_4$) were added to each reaction and incubated at 60° C. for 1 hour.

The reactions were stopped by addition of 50 μl of stop buffer containing 95% formamide and 10 mM EDTA. Two μl of each reaction were analyzed by both normal and reverse polarity gel electrophoresis. Samples were heated to 90° C. for 1 minute immediately before electrophoresis through a 15% denaturing acrylamide gel (19:1 cross-linked) with 7 M urea, in a buffer containing 45 mM Tris-Borate (pH 8.3), 1.4 mM EDTA. An electric field of 20 watts was applied for 1 hour in reverse orientation. The gel was scanned on the Hitachi FMBIO-100 fluorescence imager with 585-nM filter at 20% sensitivity.

Figure 29:
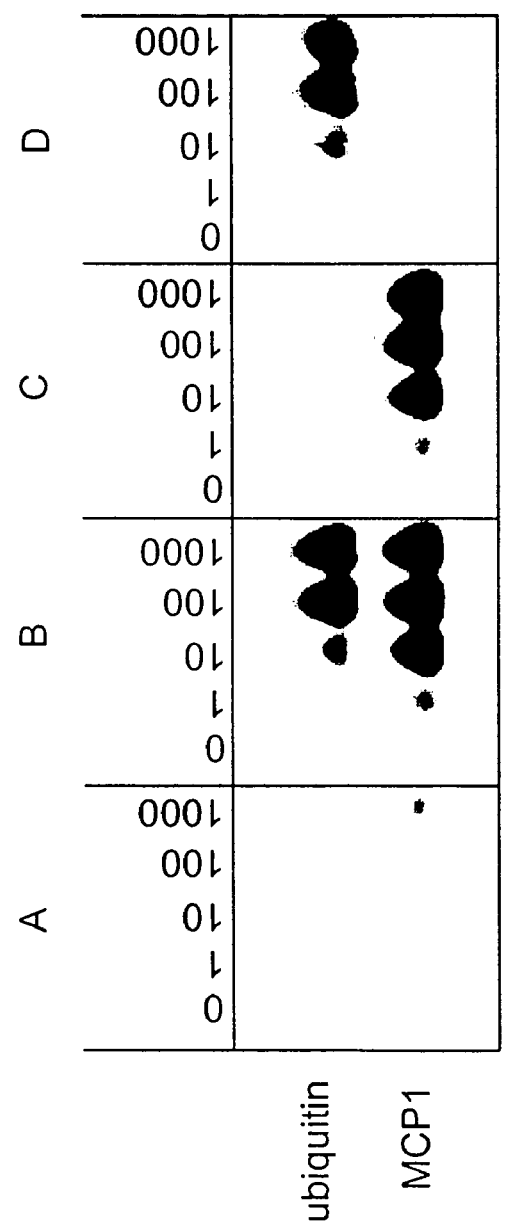
FIG. 29 is an image generated by a fluorescence imager showing the products of INVADER assays for the detection of human MCP-1 and ubiquitin mRNAs alone or combined in the same reaction. Products were resolved by gel electrophoresis run in the reverse direction.

Images of the reverse polarity gel are shown in FIG. 29, panel A: basic non-cascading reaction; panel B: multiplex, cascading reaction; panel C: cascading reaction with MPC1 reporter oligo; and panel D: cascading reaction with Ubiquitin reporter oligo.

Example 15

Detection of Human MCP1 and Ubiquitin Transcripts from Cell Lysates with a Multiplex CRE Format The previous experiment demonstrated that the positively charged probe oligonucleotides can be used to detect in vitro transcripts in a cascading, invasive cleavage reaction, and that they function well in a true, multiplex reaction format. The present experiment demonstrates that the assay format described in Example 14 can be used to detect both the hMCP1 and hubiquitin transcripts from cell lysates, and from preparations of total cellular RNA.

Cell lysates and total RNA were prepared from MG 63 cells (ATCC # CRL-1427). The cells were grown according to instructions supplied by ATCC, and by standard methods known in the art. Cells used for the lysate preparation were grown in 96 well flat bottom tissue culture plates, while cells used for the total RNA preparation were grown in 10 cm tissue culture dishes. Prior to either procedure, cells were stimulated with both human tumor necrosis factor-α (TNF-α [Calbiochem, Cat. #654205]) and human interleukin-1β (IL-1β [Calbiochem, Cat. #407615]). The final concentration in the induction medium was 10 ng/ml for both TNF-α and for IL-1β.

Cell lysates were prepared as follows: Prior to lysis, cells were washed 2× with 200 μl of phosphate buffered saline (PBS). Cells were then lysed by adding 30 μL of cell lysis buffer (20 mM Tris pH 7.5, 5 mM $MgCL_2$, 20 ng/μl tRNA, 0.5% Nonidet NP-40) and incubating at room temperature for 5 minutes. 20 μl of each lysate was transferred into a 96-well microplate (MJ Research). The plate was covered to prevent volume loss due to evaporation, and cellular nucleases were inactivated by heating the microplate at 80° C. for 15 minutes prior to the INVADER reaction.

Total RNA was isolated with Trizol reagent (Gibco BRL, Cat.# 15596) from stimulated and unstimulated cells following the manufacturer's protocol. Cells were grown in 10 cm plates to approximately 6–7×$10^6$ cells/plate and treated for 2 hours with TNF-α and IL-1β, both at 10 ng/ml. The RNA was then suspended in RNAse free distilled water (USB Cat # US70783) and stored at −70° C.

In the following experiment 3 different INVADER assay formats were used. The multiplex, cascading reaction format was used to detect each analyte; the non-multiplex, (single) cascading reaction format was also used to detect each analyte; and a basic INVADER (non-cascading) reaction format was used for hMCP1 detection only. All of the formats used the positively charged, labeled probes of the present invention as the detection moiety. Detection of each analyte was performed using total RNA, cell lysates and in vitro transcripts.

Target levels for the single and multiplex cascade reactions, as well as for the basic, non-cascading INVADER reaction were: either 0 or 1 fmole of in vitro transcript in 5 μl; 5 μl of cell lysate (approximately 2000 cells); or 50 ng of total RNA in 5 μl.

The multiplex, cascading reaction were prepared as described in Example 14 and included all the oligonucleotides required to detect both targets. The cascading reactions performed to detect only one target were prepared as described in Example 14, except the oligonucleotides required for the detection of only one of the targets (either hubiquitin or hMCP1) were added, not both. The basic, non-cascading INVADER reactions were prepared as described in Example 10.

The products of the INVADER reaction were separated on reverse polarity gel electrophoresis (positively charged cleavage products) or normal polarity gel electrophoresis (full length probes) and the gels were scanned on the Hitachi FMBIO-100 fluorescence imager with 585-nM filter at 20% sensitivity.

Figure 30:
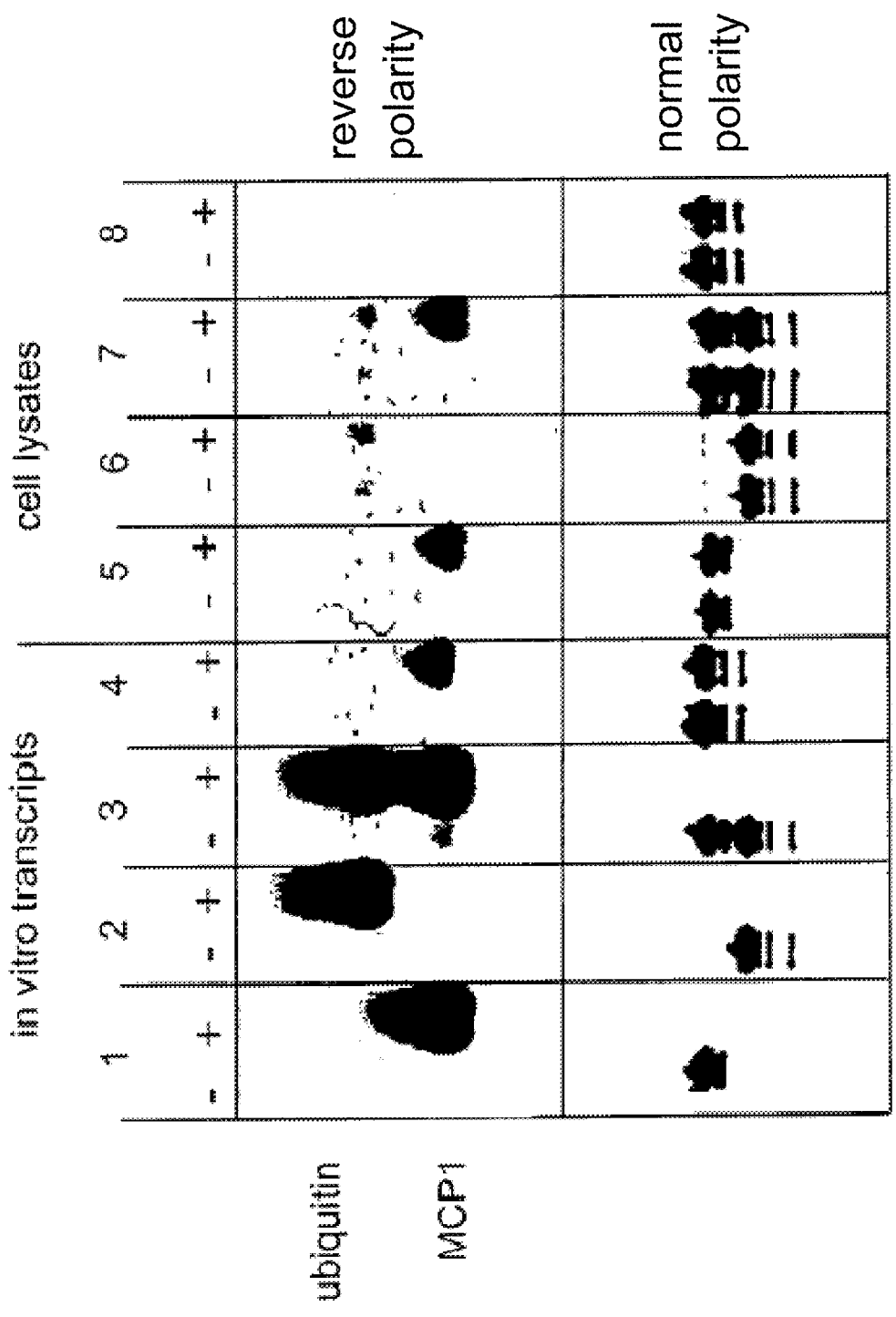
FIG. 30A shows images generated by a fluorescence imager, comparing the products of INVADER assays for the detection of human MCP-1 and ubiquitin RNAs either alone or combined in the same reaction, and resolved by gel electrophoresis run in either the reverse or normal polarity.
FIG. 30B shows images generated by a fluorescence imager, comparing the products of INVADER assays for the detection of human MCP-1 and ubiquitin RNAs either alone or combined in the same reaction, and resolved by gel electrophoresis run in either the reverse or normal polarity.
Figure 30:
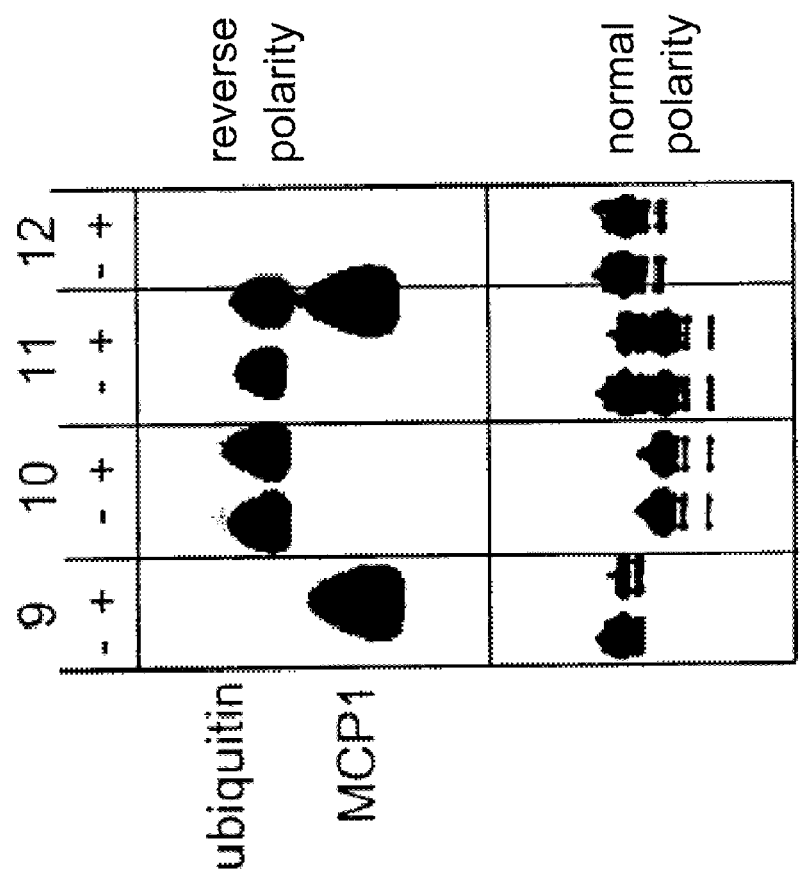

Images of the normal and reverse polarity gels are shown in FIGS. 30A and B. The normal polarity images are shown as panels below the reverse polarity panels, with the lanes showing the products of the same reactions aligned vertically. Lanes 1-4 show results with either 0 (noted by the − symbol) or 1 fmole (noted by the + symbol) of in vitro transcript; lanes 5-8 show results using cell lysates (approximately 2000 cells per reaction) with either no cellular stimulation (noted by the − symbol) or 4 hours of cellular stimulation (noted by the + symbol) prior to the lysate preparation; lanes 9-12 show results using approximately 50 ng per reaction total RNA with either no cellular stimulation (noted by the − symbol) or with 4 hours of cellular stimulation (noted by the + symbol) prior to the total RNA preparation. Lanes 1-3, 5-7 and 9-11 show the results of the cascading reaction; lanes 4, 8 and 12 show the results of the basic, non-cascading reaction.

Example 16

Detection of Positively Charged, Labeled Oligonucleotide Tags by Capillary Electrophoresis Capillary electrophoresis (CE) is an extremely useful tool that can be used for fast and effective separation of a wide variety of molecules, including DNA oligonucleotides (Baker, D. R. (1995) Capillary Electrophoresis, Wiley Interscience Publications, New York, USA), herein incorporated by reference in its entirety. CE offers the advantages of high sensitivity, ease of use, and low cost. It provides a fast and effective method for the detection of dye-labeled tags, using, for example laser induced fluorescence. Most of the commercially available CE instruments are also capable of charge reversal electrophoresis (CRE). Therefore, it was decided to employ CRE as a method to detect the positively-charged tags generated by the invasive cleavage reactions, described and demonstrated above.

An interesting feature of the different, positively charged tags (e.g., products of an INVADER assay reaction using CRE probes) is their low charge-to-mass ratio. The oligonucleotide-positive charge tags used in this study have a net charge of +1 and a mass slightly higher than that of a DNA nucleotide base. Thus, it would be extremely difficult to use the conventional CE-based DNA separation methods (such as gel-filled capillaries) because the injection times required for appropriate sample delivery would result in line broadening and poor sensitivity.

Therefore, other CE techniques, such as hydrodynamic injection and sample stacking using charged zone electrophoresis (CZE), and micellar electrokinetic capillary electrophoresis (MECC or MEKCC) (Weinberger, R. (1993) Practical capillary electrophoresis, Academic Press, San Diego, U.S.A, herein incorporated by reference in its entirety) were employed to achieve the sensitivity and resolution required for separation of the positively charged, tagged oligonucleotides.

The following examples demonstrate optimization of experimental conditions for MECC-CE based separation of the positively charged tagged oligonucleotides generated by INVADER reactions.

Optimizations of CRE Conditions: Detection of Positively Charged Oligonucleotide Tags In order to determine the optimal conditions for running CRE experiments using capillary electrophoresis employing sample stacking and micellar electrokinetic capillary electrophoresis (MECC), a number of variables were tested. The variables were determined to have the greatest effect on the resolution and sensitivity of detection of INVADER-cleaved tag products. The CRE probes were synthesized as described in Examples 4-6. The tags are depicted top to bottom in FIG. 17, and are called Tag 6, Tag 3, Tag 5, Tag 4, Tag 1 and Tag 2, respectively. The INVADER assay reactions used in these to release these tags were conducted using the oligonucleotides, target DNAs, probes and conditions described in Example 18.

Unless otherwise indicated, all experiments described below were performed on a Beckman-Coulter P/ACE MDQ capillary electrophoresis system equipped with a YAG 532 nm laser (JDS Uniphase) and a 580±10 nm emission filter (Andover Corporation, Cat.#580FS10-12.5). 100 micron eCAP (Beckman-Coulter) capillary (10 cm to window) was run at 25° C. with a constant separation voltage of 25 kV, using a separation buffer of 50 mM Bis-Tris borate pH 6.5. The capillary was pre-filled with 50 mM Bis-Tris borate pH 6.5 and 2% octylglucaside. The injected sample consisted of 10 nM final concentration mixture of the 6 tags in 10 mM MOPS, 0.05% NP40, 0.05% Tween 20, 7.5 mM $MgCl_2$, and 10 ng/μL tRNA, and was hydrodynamically injected into the capillary using a vacuum injection of 0.5 psi from the positive electrode side of the capillary. The sample was run from the positive electrode capillary end to the negative electrode capillary end, for a distance of 10 cm to the capillary window. Data is represented as stacked traces of the raw CE chromatographs without any calculations or manipulations.

Figure 31:
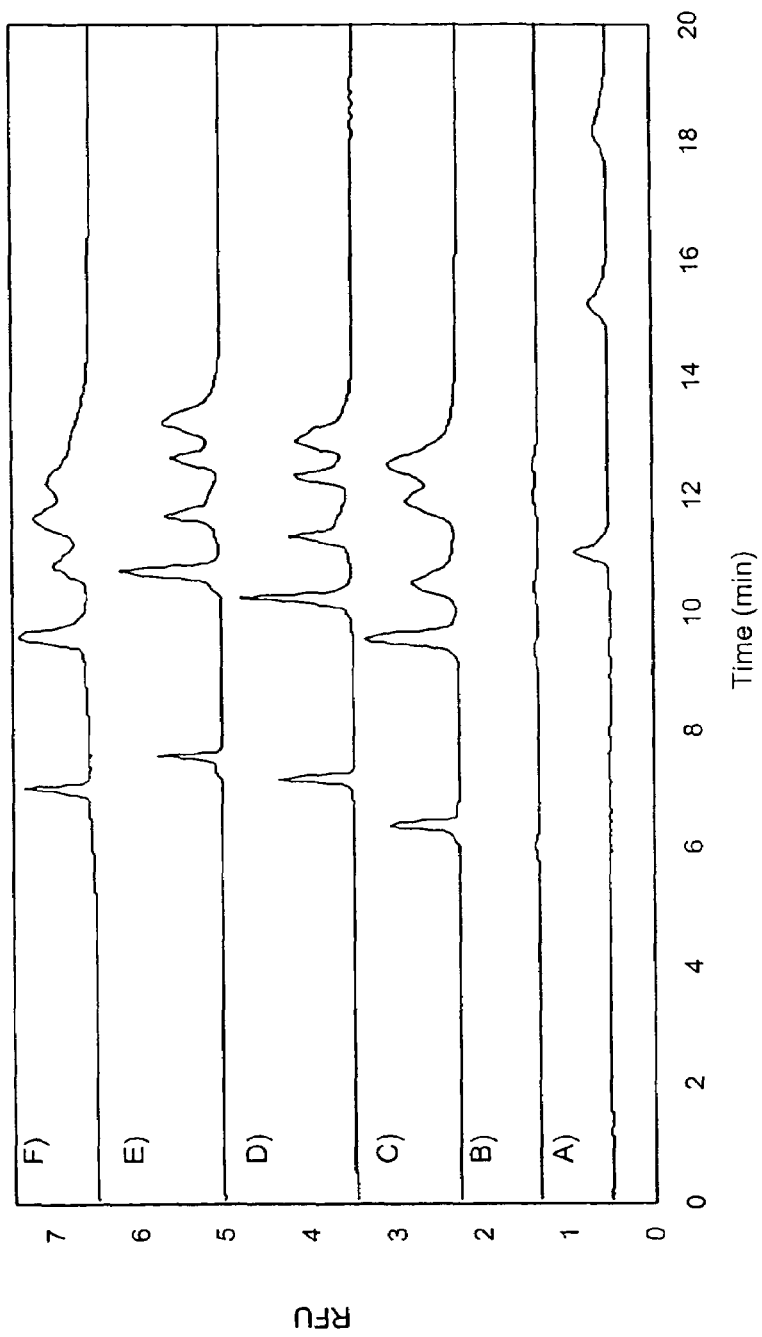
FIG. 31 shows micellar electrokinetic chromatography (MECC) profiles showing the effects of sample buffer components on CE resolution.

1) Effect of Sample Buffer Components on CE Resolution:

Since sample stacking relies on the conductivity and ionic strength differences between the sample buffer and the separation buffer, the effect of INVADER reaction buffer components on the efficiency of stacking was initially tested. To do this, 10 nM concentrations of each of the 6 tags were mixed in buffers containing water (A), 10 mM MOPS (B), 10 mM MOPS, 0.05% NP40, and 0.05% Tween 20 (C), 10 mM MOPS, 0.05% NP40, 0.05% Tween 20, and 7.5 mM $MgCl_2$ (D), 10 mM MOPS, 0.05% NP40, 0.05% Tween 20, 7.5 mM $MgCl_2$, and 10 ng/μL tRNA (E), and 10 mM MOPS, 0.05% NP40, 0.05% Tween 20, 7.5 mM $MgCl_2$, 10 ng/μL tRNA, and 10 ng/μL Afu FEN1 nuclease (F). Results are shown in FIG. 31.

It can be seen that the suggested minimal sample buffer components for optimal stacking and sensitivity are the presence of detergents (0.05% NP40 and Tween 20) along with 10 mM MOPS. Sample in water or 50 mM MOPS did not achieve any detection suggesting that the presence of detergent is important to the method. It can also be seen that sample buffer F still allows for good resolution and detection sensitivity. Since the INVADER reactions are carried out in sample buffer F, no sample treatment (i.e. desalting or concentrating) is required prior to running CRE.

2) Injection Time Effects:

Effective sample stacking is highly dependent on the volume injected into the capillary (Weinberger, R. Practical capillary electrophoresis, Academic Press, San Diego, U.S.A [1993]). In this experiment, the optimal (maximum) injection volume of sample was determined. The injected sample volume that gave the best resolution was then used in subsequent experiments.

Figure 32:
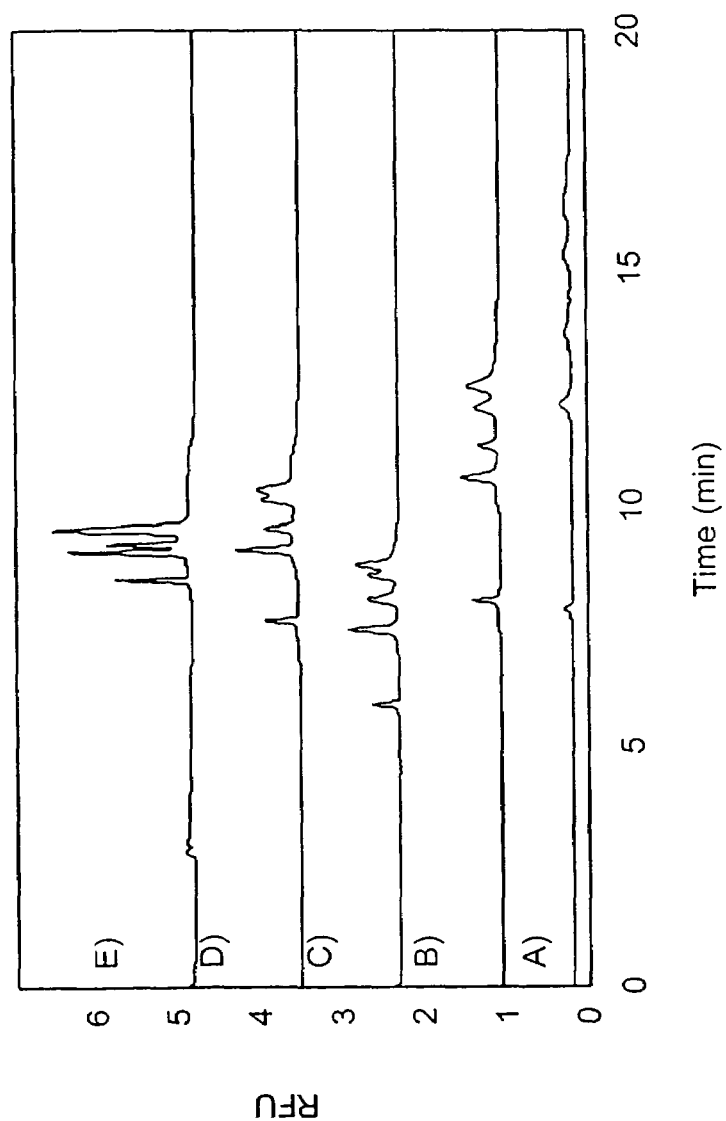
FIG. 32 shows MECC profiles showing the effects of injection time on CE resolution.

Samples were injected using a 0.5 psi vacuum for periods of 10, 20, 30, 40, and 60 seconds. Results are shown in FIGS. 32 (A, B, C, D, and E, respectively). Results show that 10 to 40 seconds injection resulted in an increase in sensitivity. However, somewhere between 40 and 60 seconds a loss in resolution is apparent, suggesting that stacking is no longer optimal. Therefore a 40 second injection time was used for all subsequent experiments.

Figure 33:
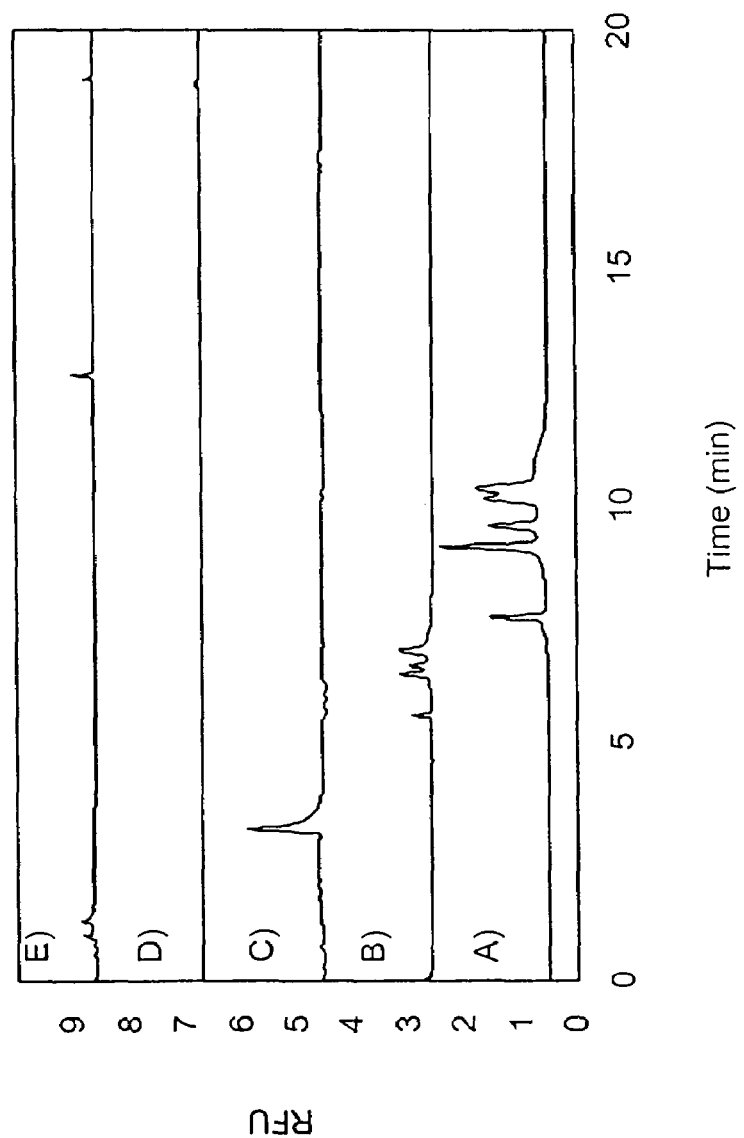
FIG. 33 shows MECC profiles showing the effects of capillary type on CE resolution.

3) Effect of Capillary Type:

The electroendosmotic flow (EOF) of CE is very dependent on the type of capillary coating used (Weinberger, (supra)). Commonly used bare-fused silica capillaries have an EOF that may cause problems for certain CE applications (Baker, D. R. Capillary Electrophoresis, Wiley Interscience Publications, New York, USA [1995]). Coated capillaries are usually used as a solution to the EOF problem. There are two different types of coatings, dynamic and static. Dynamic coating is usually achieved by adding a surfactant to the capillary filling buffer. This surfactant interacts with the silanol groups of the capillary wall, minimizing the EOF. Static coating, on the other hand, is achieved by pre-treating the bare-silica capillary with a chemical that reacts with the hydroxyls of the silanol groups coating the capillary wall, thus making it neutral and eliminating the EOF. In order to determine the best coating material for optimal CRE performance several statically coated capillaries were tested. Capillaries tested were: A) 100µ eCAP DNA polyacrylamide coated capillary (Beckman-Coulter); B) 75µ CEP coated capillary (Agilent Technologies); C) 75µ µSIL-Wax coated capillary (J&W Scientific); D) 75µ 5% T, 5% G pre-filled µPAGE capillary (J&W Scientific); E) 75µ bare fused silica (Beckman-Coulter) (FIG. 33). Results show that capillaries with hydrophilic coatings (i.e. polyacrylamide 100µ eCAP and 75µ CEP) yield the best separation and sensitivity. This suggests that with the appropriate coating material (dynamic or static), bare-silica can be efficiently used to resolve CRE-based INVADER assays.

4) Separation (Electrode) and Capillary Filling Buffer Effects on CRE

Figure 34:
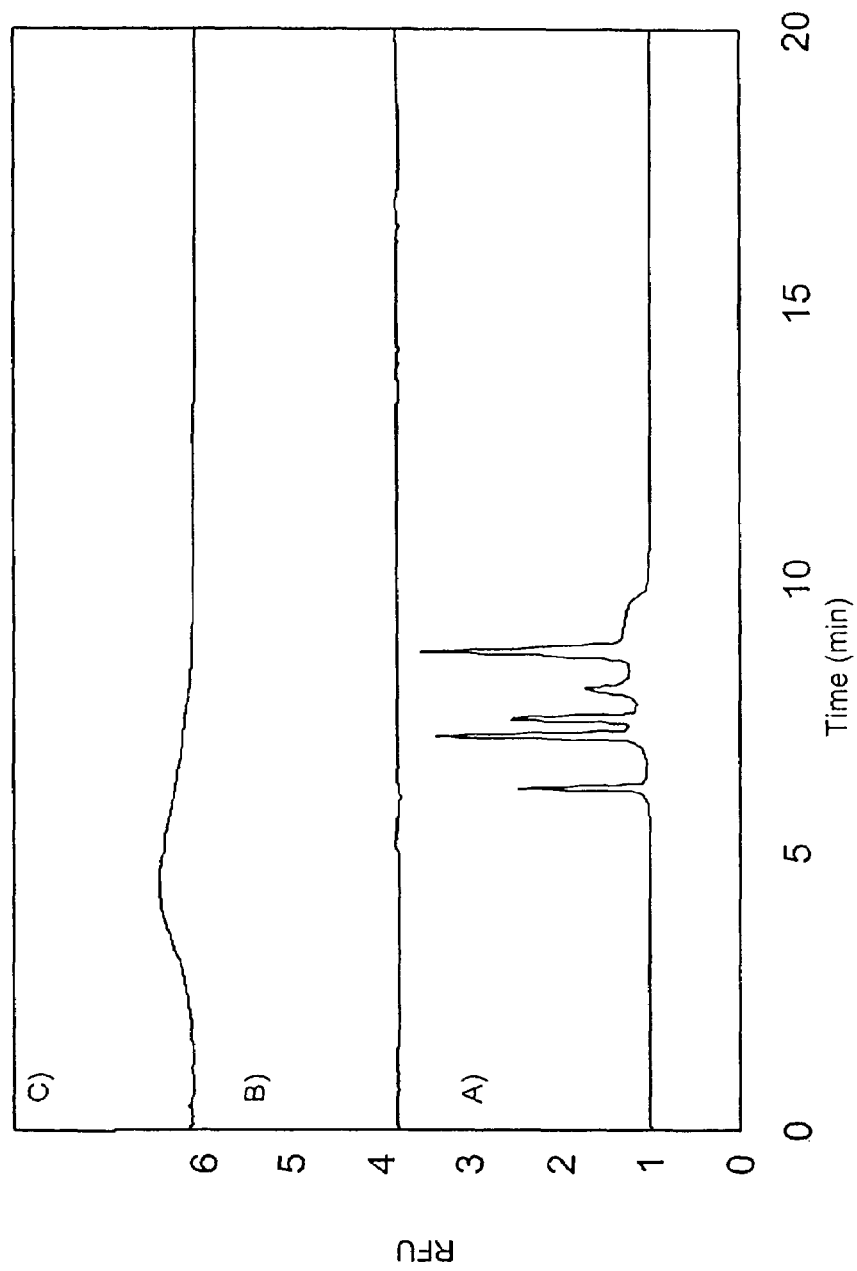
FIG. 34 shows MECC profiles showing the effects of ionic strength of the separation buffer on CE resolution.
Figure 35:
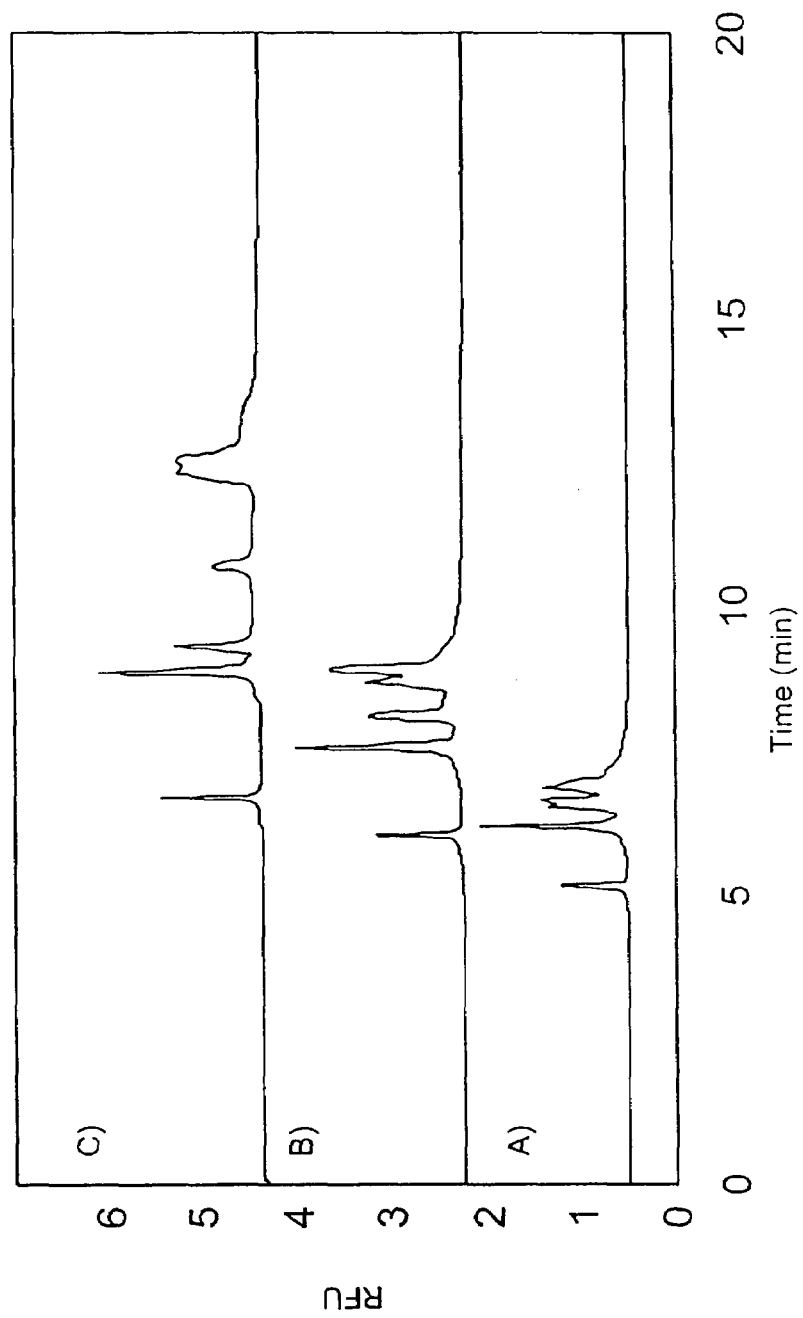
FIG. 35 shows MECC profiles showing the effects of the pH of the separation buffer on CE resolution.

To determine the ionic strength of the separation buffer that will yield maximum sample stacking, CRE was performed on INVADER assay tag products using 50 mM concentrations, pH 7.2 of: (A) Bis-Tris.borate, (B) Tris-borate, and (C) MOPS. For these experiments, the capillary was filled with the same buffer as the separation buffer, with the addition of 2% octylglucoside to achieve MECC conditions. FIG. 34 shows the results of the different buffers used. Optimal stacking is obtained for the buffer containing 50 mM Bis-Tris borate, pH 7.2. Next, the pH of this buffer was optimized for use in subsequent CE experiments. The buffer pHs tested were: 50 mM Bis-Tris borate buffers of (A) pH 6.0, (B) 6.5, and (C) 7.2. Results are shown in FIG. 35. Optimal sample stacking and separation of INVADER-generated positive tags are obtained at pH 6.5.

Figure 36:
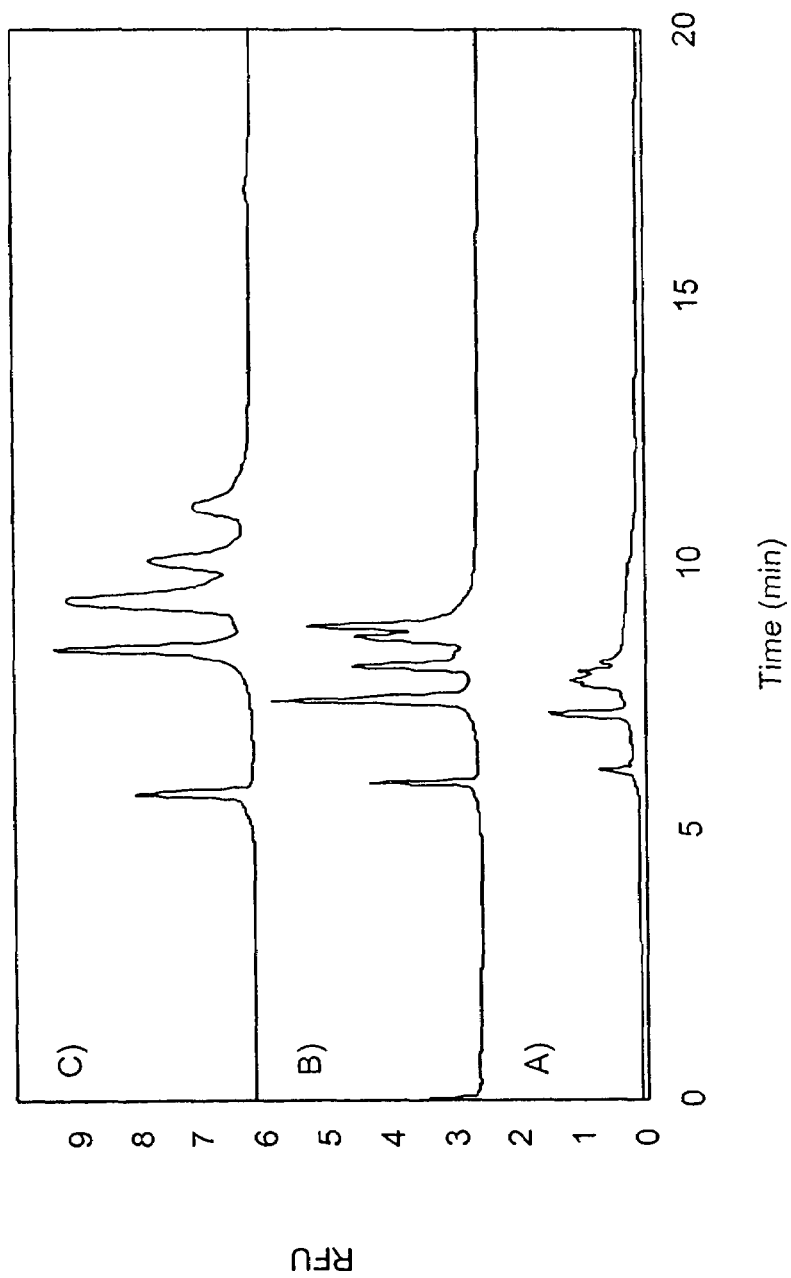
FIG. 36 shows MECC profiles showing the effects of the concentration of Bis-Tris borate buffer on CE resolution.

Finally, to determine the optimal concentration of Bis-Tris.borate buffer to be used, concentrations of 25 mM (A), 50 mM (B), and 100 mM (C)—all at pH 6.5—were tested (FIG. 36). Results indicate that the optimal concentration of Bis-Tris borate is 50 mM. The use of non-borate based buffers such as TAE, phosphate, and citrate, for example, are also contemplated.

5) Effect of Detergent on the Efficiency of MECC Separation of INVADER Assay-generated Positive Tags MECC takes advantage of interactions between the sample to be separated by CE and the hydrophilic charged ends of micelles commonly formed by detergent (Weinberger, supra). To determine which micelle-forming detergent would give optimal results, a number of different detergents were tested. CRT was performed using capillaries filled with 50 mM Bis-Tris borate, pH 6.5 buffer (A) without any detergent additions; (B) with 2% octylglucoside; (C) 2% NP-40; (D) 2% Tween-20; (E) 2% Triton X100; (F) 2% MEGA-9; (G) 2% Brij 35; and (H) 30 mM Sodium Cholate.

Figure 37:
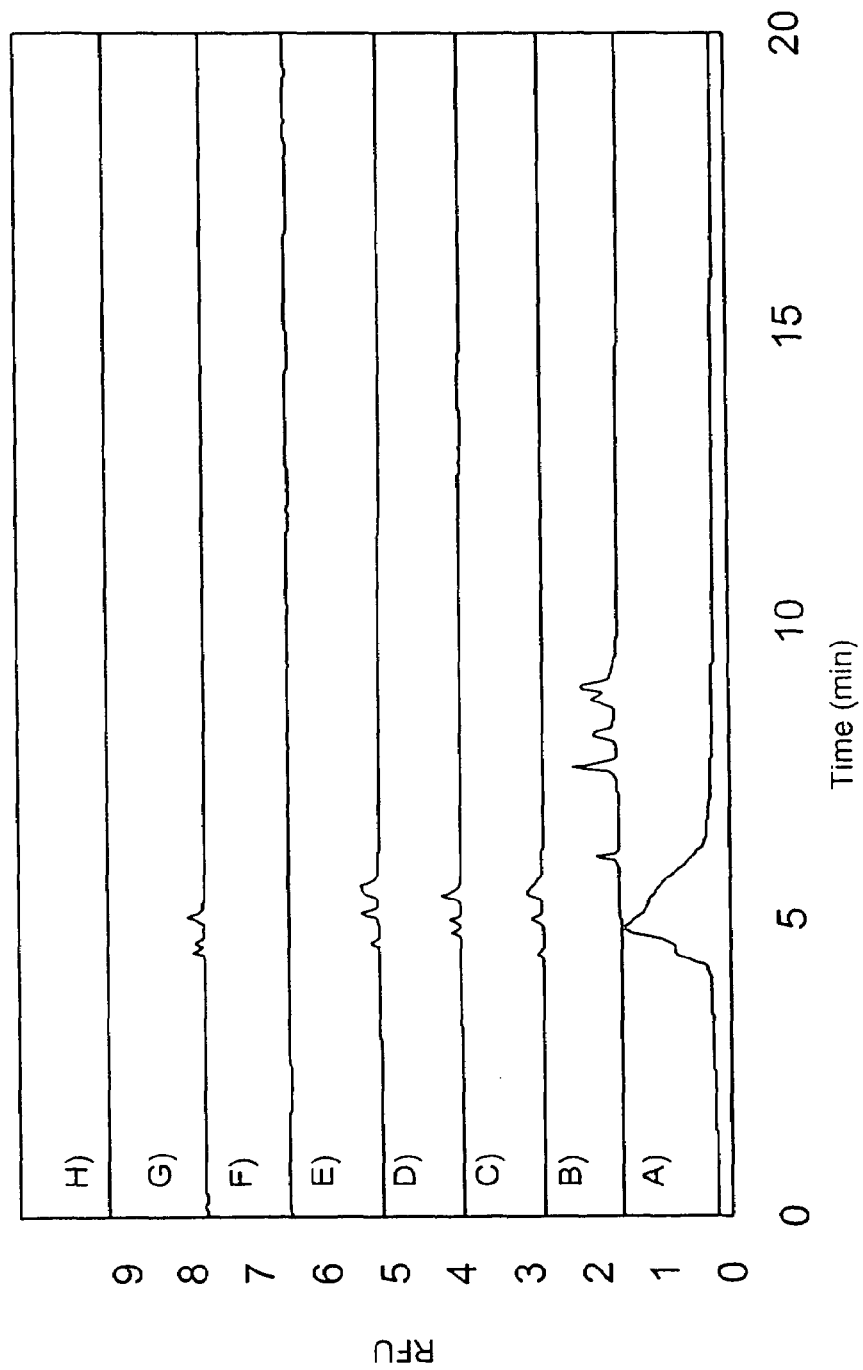
FIG. 37 shows MECC profiles showing the effects of the detergent of the efficiency of CE resolution.

Results are shown in FIG. 37. It can be seen that optimal MECC resolution is obtained in the presence of 2% octylglucoside and that the use of NP-40, Tween-20, Triton X100, and Brij 35 result in lower resolution. The use of MEGA-9 and sodium cholate resulted in no sample detection. It is also worth noting that the presence of no detergent produced a single peak of poor resolution suggesting that sample stacking was still successful.

Example 17

Analysis of H-phosphonate Modifications by Using Capillary Electrophoresis

In this example, the products of the INVADER reactions using H-phosphonate tags described above (e.g., in Example 10) were analyzed by capillary electrophoresis (CE). Compared with gel electrophoresis, capillary electrophoresis offers higher sensitivity and resolution, faster separation time, automation capabilities and the ability to use conditions that cannot be applied to a gel format, such as MECC.

Four net positively charged tags 5'-V-(Hex)-Cy3-C-3', 5'-V-(dA)-Cy3-C-3', 5'-V-(dG)-Cy3-C-3', and 5'-V-(dT)-Cy3-C-3' were generated by the invasive cleavage of the corresponding probes, as described in Example 10 (SEQ ID NOS:61-65, respectively). Briefly, 10 pmole of each probe oligo (P1, P2, P4 and P5) were cleaved in the presence of 10 fmole of human MCP1 in vitro transcripts for 3 hours to ensure nearly complete conversion of the probes to the cleaved products. The cleaved tags were diluted to 10 nM concentration using a solution containing 10 mM MOPS, pH 7.5, 7.5 mM $MgCl_2$, 10 ng/µL tRNA (Sigma), 0.05% Tween 20, and 0.05% Nonidet P40 to mimic the buffer conditions of INVADER reaction. The samples were separated in 60 cm eCAP DNA 100 µm diameter capillary (Beckman) under conditions of micellar electrokinetic chromatography (MECC) using a PageMDQ CE instrument (Beckman) equipped with a 532-nm laser and 580±20 nm emission filter. The capillary-filling buffer contained 50 mM bis-Tris-borate, pH 6.5 and 2% octylglucoside (Sigma) and the electrode buffers contained 50 mM bis-Tris borate, pH 6.5. The samples were injected by applying 0.5 psi vacuum to the outlet end of the capillary for 20 seconds. The tags were separated by applying 16 kV electric field, with the positive electrode connected to the inlet buffer. The separation distance from the inlet end of the capillary to the detector window was 10 cm.

Figure 38:
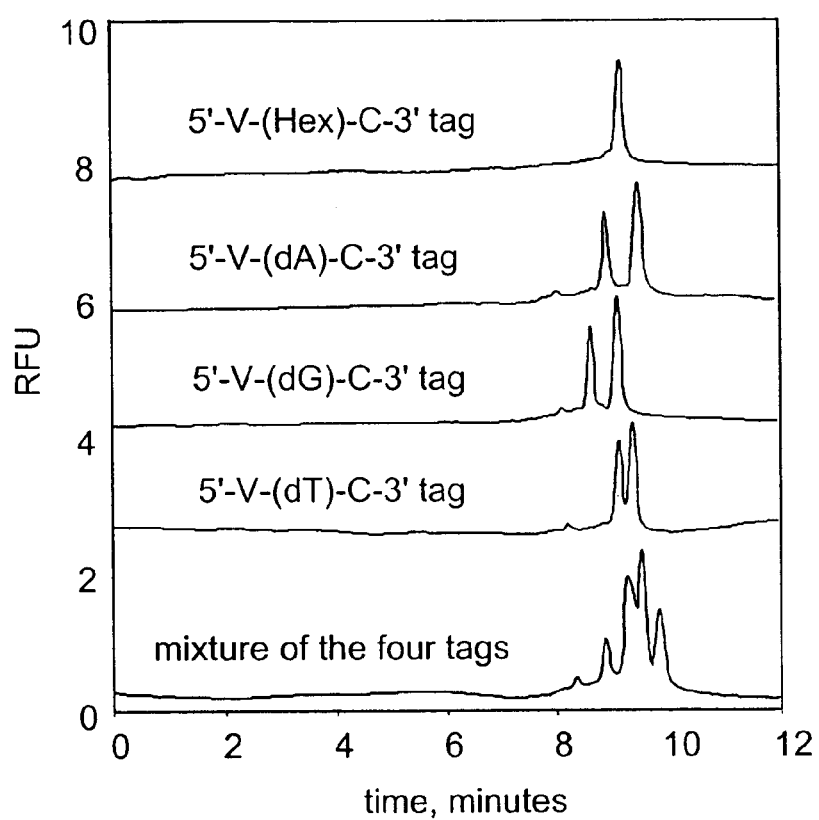
FIG. 38 shows MECC profiles for the four net positively charged tags, 5'-V-Cy3-C-3', 5'-V-(dA)-Cy3-C-3', 5'-V-(dG)-Cy3-C-3', and 5'-V-(dT)-Cy3-C-3', separated individually and as an equimolar mixture of all four molecules.

FIG. 38 shows MECC profiles for the four net positively charged tags 5'-V-(HEX)-Cy3-C-3', 5'-V-(dA)-Cy3-C-3', 5'-V-(dG)-Cy3-C-3', and 5'-V-(dT)-Cy3-C-3' separated individually and as an equimolar mixture of all four molecules. Tag 5'-V-(Hex)-Cy3-C-3' produced a single band, whereas each of the tags 5'-V-(dA)-Cy3-C-3', 5'-V-(dG)-Cy3-C-3', and 5'-V-(dT)-Cy3-C-3' demonstrated two major peaks. The double-peak profiles can be explained by the presence of diastereoisomers formed during the synthesis of each of the studied tags. The stereoisomers formed by tag 5'-V-(Hex)-Cy3-C-3' are not separated under these experimental conditions. The separation of a mixture of all four tags shows only four peaks rather than expected seven peaks, suggesting that some tags or diastereoisomers have similar mobilities in these conditions.

Figure 39:
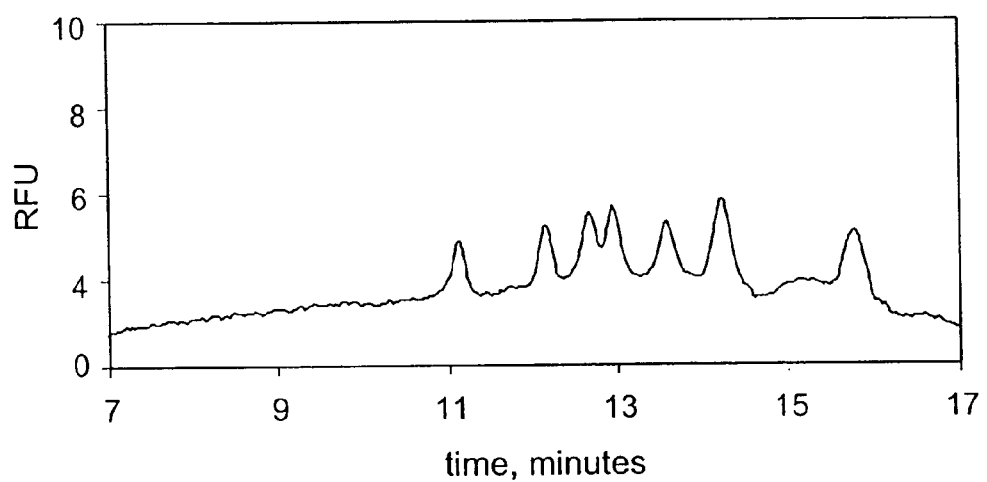
FIG. 39 shows MECC profiles demonstrating the effect of the use of a fresh capillary on the separation of the tag mixture shown in FIG. 38.

It was observed that resolution of eCAP DNA capillaries gradually decreases after 10-20 runs, which could affect the separation of tags mixture shown in FIG. 38. When a fresh capillary was used to analyze the same mixture of the four tags, all seven peaks were observed under the same conditions (FIG. 39).

Example 18

Separation of Net Positively Charged Tags Synthesized using Phosphoramidite Chemistry Synthesis of charge-balanced oligonucleotides can be performed using a phosphoramidite chemistry as described in Examples 4-6. In comparison with H-phosphonate chemistry used for the tags described in Examples 7 and 8, the phosphoramidite chemistry offers the advantage of using commercially available synthesizers and avoiding the introduction of centers of chirality at the phosphoramidate phosphorus atom during the synthesis. Six oligonucleotides with a general structure 5'-TagN-GCT CCC GCA GAC AC-3' (SEQ ID NO:83), where TagN denotes one of the six net positively charged modifications described in Examples 4-6, (shown top to bottom in FIG. 17, and called Tag 6, Tag 3, Tag 5, Tag 4, Tag 1 and Tag 2, respectively). Each probe was cleaved in an invasive cleavage reaction with the INVADER oligonucleotide 5'-CAA AGA AAA GCT GCG TGA TGA TGA AAT CGC-3' (SEQ ID NO:84, termed 509-54-3) and the target oligonucleotide 5'-GAA GGT GTC TGC GGG AGC CGA TTT CAT CAT CAC GCA GCT TTT CTT TGA GG-3' (SEQ ID NO:85, termed 509-54-1) to generate net positively charged tags 5'-TagN-G-3'.

Each INVADER assay reaction was performed with 2 µM of one of the six probes, 0.1 µM INVADER oligonucleotide 509-54-3, 10 nM target oligonucleotide 509-54-1, and 100 ng of Ave FEN1 CLEAVASE enzyme (at 10 ng/µl) in a 10 µL solution containing 10 mM MOPS, pH 7.5, 7.5 mM $MgCl_2$. The reactions were incubated at 63° C. for 3 hours. Under these conditions, nearly all the probe molecules were cleaved generating approximately 2 µM of each positively charged tag. The cleaved products were diluted to 10 nM concentration in a solution containing 10 mM MOPS, pH 7.5, 7.5 mM $MgCl_2$, 10 ng/µL tRNA (Sigma), 0.05% Tween 20, and 0.05% Nonidet P40 and analyzed by MECC as described in Examples 16 and 17.

Figure 40:
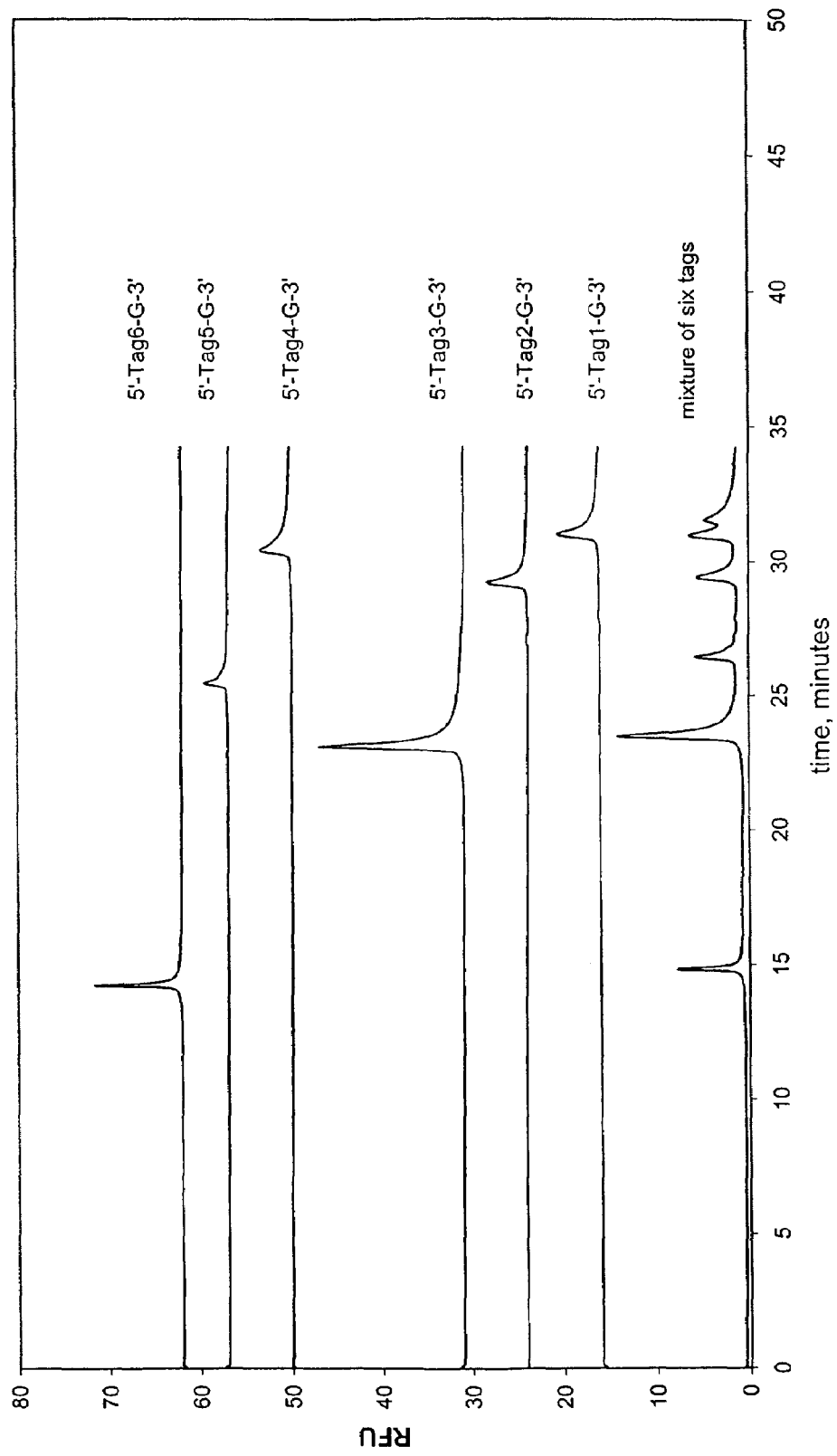
FIG. 40 shows MECC profiles for each of six net positively charged tags separated individually or as an equimolar mixture of all six molecules.

FIG. 40 shows MECC profiles for each of the six net positively charged tags separated individually or as an equimolar mixture of all six molecules. Each of the tags produced a single peak, confirming the absence of chirality centers from the modifications. The MECC separation of the mixture of all six tags shows six peaks, indicating that the CE conditions described here are able to detect the differences in chemical structure of all six tags bearing net positively charged modifications. Separation demonstrating the power of the MECC assay is emphasized by the fact that modifications in two pairs of tags, Tag1/Tag2 and Tag4/Tag5, are composed of identical chemical building blocks differing only in the order of attachment, and therefore have an identical chemical composition. Nonetheless, they were easily resolved, demonstrating that the order of addition can be used as an additional variable, further extending the library of tags that can be configured from a collection of simple building blocks.

Figure 41:
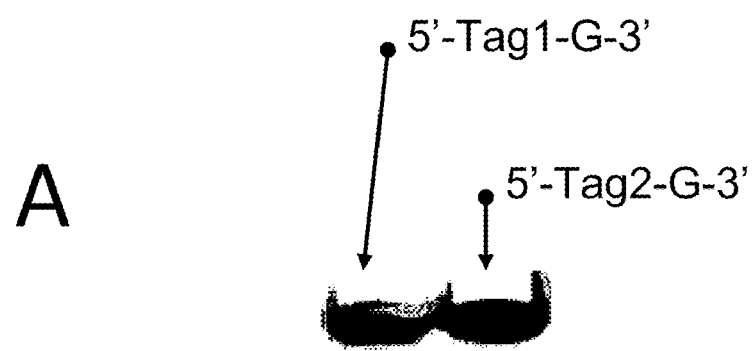
FIG. 41 shows images generated by a fluorescence imager comparing the mobility of 5'-Tag1-G-3' or 5'-Tag2-G-3' under the conditions of a denaturing gel (A) to the mobility under conditions of a native gel (B).
Figure 41:
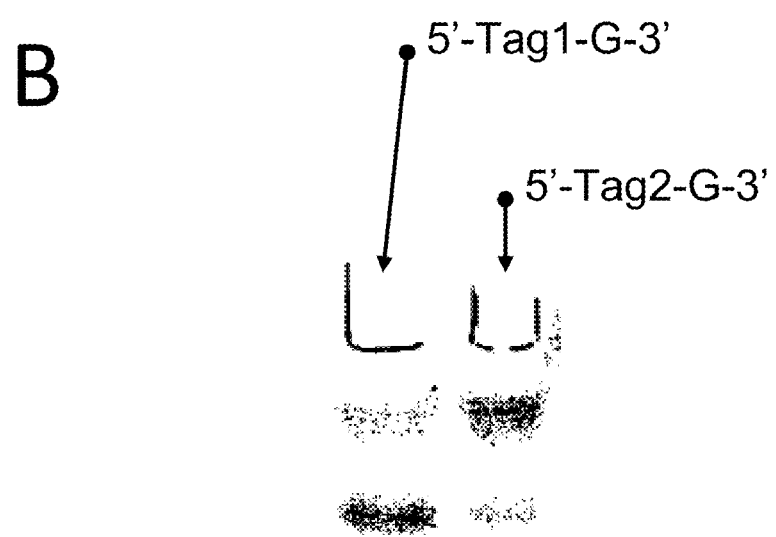

Superior resolution of MECC assay compared with gel electrophoresis is demonstrated in FIG. 41. Samples containing 0.2 pmol of 5'-Tag1-G-3' or 5'-Tag2-G-3' in 2 µL of 95% formamide, 20 mM EDTA and 0.02% methyl violet were loaded on a 100×100×2 mm slab of 20% denaturing polyacrylamide gel (crosslinked 19:1) with 7 M urea in a buffer containing 45 mM Tris-borate, pH 8.3 and 1 mM EDTA FIG. 41A) or on a 100×100×2 mm slab of 10% native polyacrylamide gel (crosslinked 19:1) in a buffer containing 50 mM bis-Tris-borate, pH 6.5 (FIG. 41B). The samples were separated by applying an electric field of 5 watts power for 30 minutes with the positive electrode connected to the top buffer reservoir (reverse orientation). The tags were visualized using FMBIO-100 fluorescence imager as described in Example 9. FIG. 41A shows that 5'-Tag1-G-3' or 5'-Tag2-G-3' have very low mobility under the conditions of the denaturing gel, precluding their identification based on this characteristic. Under the native conditions (FIG. 41B), each of the net positively charged tags was separated as two bands. There was no significant difference in the electrophoretic mobility between the two tags to distinguish them from each other.

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of separating oligonucleotides, comprising the steps of:
   a) treating a charge-balanced oligonucleotide containing a charge tag under conditions such that a charge-unbalanced oligonucleotide containing said charge tag is produced, wherein said charge-unbalanced oligonucleotide is contained in a reaction mixture; and
   b) separating said charge-unbalanced oligonucleotide from said reaction mixture.

2. The method of claim 1, wherein said conditions comprise treating said charge-balanced oligonucleotide with a reactant, wherein said reactant is selected from the group consisting of an enzyme, a chemical and a device.

3. The method of claim 1, wherein said charge tag is attached to a terminal end of said oligonucleotide, said charge tag attached to a terminal end comprising a phosphate group and a positively charged moiety.

4. The method of claim 1, wherein said charge tag comprises a dye.

5. The method of claim 4, wherein said dye is positioned between said oligonucleotide and said positively charged moiety.

6. The method of claim 4, wherein said positively charged moiety is positioned between said oligonucleotide and said dye.

7. The method of claim 3, wherein said charge tag further comprises a second positively charged moiety.

8. The method of claim 1, wherein said charge tag comprises one or more nucleotides.

9. The method of claim 8, wherein said oligonucleotide comprises a sequence complementary to a target nucleic acid, wherein said one or more nucleotides of said charge tag are not complementary to said target nucleic acid.

10. The method of claim 3, wherein said oligonucleotide comprises a first portion complementary to a target nucleic acid and a second portion that is not complementary to said target nucleic acid, wherein said second portion comprises said terminal end.

11. The method of claim 1, wherein said charge-balanced oligonucleotide has a net neutral charge and wherein said charge-unbalanced oligonucleotide has a net positive charge.

12. The method of claim 1, wherein said charge-balanced oligonucleotide has a net negative charge and wherein said charge-unbalanced oligonucleotide has a net positive charge.

13. The method of claim 1, wherein said charge tag contains a primary amine.

14. The method of claim 1, wherein said charge tag contains a secondary amine.

15. The method of claim 1, wherein said charge tag contains a tertiary amine.

16. The method of claim 1, wherein said charge tag contains an ammonium group.

17. The method of claim 1, wherein said charge tag comprises a a positively charged moiety added by coupling of a positively charged phosphoramidite.

18. The method of claim 1, wherein said charge tag comprises a a neutral moiety added by coupling of a neutral phosphoramidite.

19. The method of claim 1, wherein said separating comprises capillary electrophoretic separation.

20. The method of claim 1, wherein said separating comprises capillary zone electrophoretic separation.

21. The method of claim 1, wherein said separating occurs in a microchannel.

* * * * *